US007829114B2

(12) United States Patent
Thompson et al.

(10) Patent No.: US 7,829,114 B2
(45) Date of Patent: Nov. 9, 2010

(54) CAPSULES CONTAINING AQUEOUS FILL COMPOSITIONS STABILIZED WITH DERIVATIZED CYCLODEXTRIN

(75) Inventors: Diane O. Thompson, Overland Park, KS (US); James D. Pipkin, Lawrence, KS (US); Rupert O. Zimmerer, Lawrence, KS (US)

(73) Assignee: CyDex Pharmaceuticals, Inc., Lenexa, KS (US)

(*) Notice: Subject to any disclaimer, the term of this patent is extended or adjusted under 35 U.S.C. 154(b) by 973 days.

(21) Appl. No.: 11/076,072

(22) Filed: Mar. 9, 2005

(65) Prior Publication Data

US 2005/0186267 A1 Aug. 25, 2005

Related U.S. Application Data

(63) Continuation of application No. PCT/US03/30960, filed on Sep. 12, 2003.

(60) Provisional application No. 60/410,850, filed on Sep. 13, 2002.

(51) Int. Cl.
*A61K 9/48* (2006.01)
*A61K 9/66* (2006.01)

(52) U.S. Cl. ........................ 424/451; 424/452; 424/455

(58) Field of Classification Search ....................... None
See application file for complete search history.

(56) References Cited

U.S. PATENT DOCUMENTS

| | | | | |
|---|---|---|---|---|
| 5,376,645 | A * | 12/1994 | Stella et al. | 514/58 |
| 5,506,216 | A * | 4/1996 | Schmidt et al. | 514/58 |
| 6,383,471 | B1 * | 5/2002 | Chen et al. | 424/45 |
| 2005/0112189 | A1 | 5/2005 | Motoune et al. | |

* cited by examiner

*Primary Examiner*—Humera N Sheikh
(74) *Attorney, Agent, or Firm*—Sterne, Kessler, Goldstein & Fox P.L.L.C.

(57) ABSTRACT

A capsule containing an aqueous fill composition that comprises water, a derivatized cyclodextrin, such as sulfoalkyl ether cyclodextrin (SAE-CD) or hydroxypropyl cyclodextrin (HPCD), optionally one or more active agents and optionally one or more excipients is stabilized from degradation, erosion, swelling or dissolution of its shell during storage. The derivatized cyclodextrin is present in an amount sufficient to reduce, eliminate or inhibit degradation, erosion, swelling and/or dissolution of the shell by water present in the fill composition. Alternatively, the derivatized cyclodextrin and another shell-stabilizing material together stabilize the shell from degradation, erosion, swelling and/or dissolution by water present in the fill composition. The derivatized cyclodextrin can reduce the water activity of the fill composition.

19 Claims, 21 Drawing Sheets

HFC

Shionogi HPMC (hard capsule)

CAPSULES CONTAINING AQUEOUS FILL COMPOSITIONS STABILIZED WITH DERIVATIZED CYCLODEXTRIN

CROSS REFERENCE TO EARLIER FILED APPLICATIONS

The present application claims the benefit of priority of and is a CONTINUATION of PCT International Patent Application Serial Number PCT/US03/030960 filed Sep. 12, 2003, and claims the benefit of priority of U.S. Provisional Application for Patent Ser. No. 60/410,850 filed 13 Sep. 2002, the entire disclosures of which are hereby incorporated by reference.

FIELD OF THE INVENTION

The present invention relates to a capsule containing a derivatized cyclodextrin in an aqueous fill, wherein the cyclodextrin is present in an amount sufficient to stabilize the shell of the capsule from erosion, dissolution, swelling or degradation by water in the fill.

BACKGROUND OF THE INVENTION

Liquid, or semi-solid filled capsules are widely known. These fill compositions are generally preferred over solid filled capsules, since it is easier to obtain a higher content uniformity for liquid or semi-solid filled capsules than it is for solid filled capsules.

Capsule fill compositions can be aqueous or non-aqueous. Materials generally used for capsule fill compositions include: 1) water-immiscible, volatile and nonvolatile liquids, 2) water miscible, volatile and nonvolatile liquids, and 3) miscellaneous carriers such as glycerin, propylene glycol, water, and low-molecular weight alcohols, ketones, acids, amines, and esters. Suspensions of the active are often included in vegetable or mineral oils, triglycerides, glycols such as polyethylene glycols and propylene glycol, surfactants such as polysorbates, or combinations of these.

The shell-forming material of the capsule is chosen so as to maximize the stability of the shell toward the fill composition, while at the same time maintaining the desired release profile for the active agent. Non-aqueous fill compositions are used widely because the shell of a capsule must be water soluble, erodible or degradable in order to be useful for use in an aqueous environment, e.g., for oral administration to a subject. Quite often, however, it is desirable to include water in the fill composition in order to obtain the desired active agent release profile, increase dissolution of active agent in the fill composition and/or maximize stability of the ingredients in the fill composition. When an aqueous fill composition is used, the shell of the capsule is generally made of material that is more resistant to water dissolution, erosion or degradation.

A number of different relatively water stable shell compositions are known. Those shell compositions generally include materials or are made by processes that reduce the instability of the shell toward water in the fill composition. For example, Banner PHARMACAPS and Cardinal Health provide capsules that are somewhat stabilized for a lipophilic fill and other for a hydrophilic fill. However, using such a shell results in altered performance of the capsule formulation. Accordingly, the pharmaceutical scientist must carefully balance the amount of water included in the fill composition against the aqueous stability properties of the shell. Moreover, the known aqueous fill compositions are limited in the amounts of water and the combination of active agents and excipients that can be included therein. In other words, known shells containing fill compositions with high amounts of water still degrade, dissolve, swell or erode during storage.

A number of references disclose capsule dosage forms filled with an aqueous liquid or semi-solid vehicle, an active agent, and another component added to reduce or stop dissolution, erosion or degradation of the shell by the fill composition.

Kuentz et al. (*International J. Pharmaceutics* (2002), 236 (1-2), 145-152) disclose capsules filled with a liquid composition comprising water, PEG and poly(vinyl pyrrolidone) or comprising water, glycerides (LABRASOL®) and colloidal silicon dioxide (AEROSIL®). The components were added to determine which combination thereof would be able to reduce or stop dissolution, erosion or degradation of the shell by the fill composition. KUENTZ et al. do not disclose the use of cyclodextrins.

Bowtle (Presentation entitled "Liquid-encapsulation technology for oral delivery") discloses the use of hydrogenated glucose syrup as a material suitable for use in liquid-filled capsules. Bowtle does not disclose the use of cyclodextrins to reduce or stop dissolution, erosion or degradation of the shell by the fill composition.

Japanese Patent No. JP 61207329 to Mochizuki et al. discloses a soft gelatin capsule filled with an aqueous liquid vehicle, a sugar and an active agent. The sugar is present in amounts of 2 55% wt. with respect to the fill composition. Sugars such as sucrose, glucose, fructose, and maltose are disclosed. The sugar is present in an amount sufficient to reduce or stop dissolution, erosion or degradation of the shell by the fill composition. Mochizuki et AL. do not disclose the use of cyclodextrins to reduce or stop dissolution, erosion or degradation of the shell by the fill composition.

German Patent No. DE 19545043 to Lucks et al. discloses a liquid-filled soft gelatin capsule. The liquid is present in a single phase. The fill composition comprises 1-20% wt. polyol (such as glycerol, propanediol or PEG) or benzyl alcohol, 1-20% wt. surfactant, 79-98% WT. co-surfactant (such as glycerides), <5% wt. ethanol and <10% wt. water. Lucks et al. do not disclose cyclodextrins. Water is present in an amount low enough to minimize dissolution, erosion or degradation of the shell by the fill composition. Lucks et al. do not disclose the use of cyclodextrins to reduce or stop dissolution, erosion or degradation of the shell by the fill composition.

U.S. Pat. No. 5,037,698 to Brunel discloses a solid or semi-solid filled capsule wherein the fill composition comprises water (0.1-10% wt. ), a thickening agent (235% wt.), a hygroscopic or deliquescent agent (0.1-50% wt. ) and optionally an equilibrium protecting agent (0.1-15% wt. ). The water is present at or near stoichiometric amounts with respect to the hygroscopic or deliquescent agent so that a hydrate can form but degradation of the shell by water is minimized. The thickening agent is a thermosoftening solid or semi-solid excipient. The equilibrium protecting agent includes compounds such as aliphatic or aromatic hydroxy compounds including for example demulcents (glycerin) and oils. Brunel does not disclose the use of cyclodextrins.

U.S. Pat. No. 5,707,648 to Yiv discloses a biphasic liquid-filled capsule containing an oil phase and an aqueous phase. The aqueous phase includes water (2-30% wt.) and PEG (60-95% wt.), wherein the ratio of PEG to water is $\geqq$2:1 or 2:1-99:1. The formulation also requires a surfactant and an active agent. The PEG is present in an amount sufficient to reduce or stop dissolution, erosion or degradation of the shell by the fill composition. Yiv does not disclose the use of cyclodextrins.

U.S. patent Pregrant Publication No. 2003/0133974 to Curatolo et al. discloses an encapsulated dosage form containing sertraline; however, that dosage form comprises a water immiscible carrier medium.

Cyclodextrins and their derivatives are widely used in liquid formulations to enhance the aqueous solubility of hydrophobic compounds. Cyclodextrins are cyclic carbohydrates derived from starch. The unmodified cyclodextrins differ by the number of glucopyranose units joined together in the cylindrical structure. The parent cyclodextrins contain 6,7, or 8 glucopyranose units and are referred to as α-, β-, and γ-cyclodextrin respectively. Each cyclodextrin subunit has secondary hydroxyl groups at the 2 and 3-positions and a primary hydroxyl group at the 6-position. The cyclodextrins may be pictured as hollow truncated cones with hydrophilic exterior surfaces and hydrophobic interior cavities. In aqueous solutions, these hydrophobic cavities provide a haven for hydrophobic organic compounds, which can fit all, or part of their structure into these cavities. This process, known as inclusion complexation, may result in increased apparent aqueous solubility and stability for the complexed drug. The complex is stabilized by hydrophobic interactions and does not involve the formation of any covalent bonds.

Chemical modification of the parent cyclodextrins (usually at the hydroxyl moieties) has resulted in derivatives with sometimes improved safety while retaining or improving the complexation ability of the cyclodextrin. A number of different cyclodextrin derivatives are currently available including sulfobutyl ether derivatives such as SBE1-β-CD and SBE4-β-CD (degree of substitution-4), SBE7-β-CD (degree of substitution ~7; CAPTISOL cyclodextrin); hydroxypropyl derivatives such as ENCAPSIN™ (degree of substitution-4 ; HP4-β-CD) and MOLECUSOL™ (degree of substitution ~8; HP8-β-CD); carboxylated derivatives; sulfated derivatives; alkylated derivatives; hydroxyalkylated derivatives; methylated derivatives; and carboxy-β-cyclodextrins, e. g. succinyl-β-cyclodextrin, $6^A$-amino-$6^A$-deoxy-N-(3-carboxypropyl)-β-cyclodextrin.

The SAE-CDs are a class of negatively charged cyclodextrins, which vary in the nature of the alkyl spacer, the salt form, the degree of substitution and the starting parent cyclodextrin. The sodium salt of the sulfobutyl ether derivative of beta-cyclodextrin, with an average of about 7 substituents per cyclodextrin molecule (SBE7-β-CD), is being commercialized by CyDex, Inc. (Kansas) as CAPTISOL®;CYCLODEXTRIN.

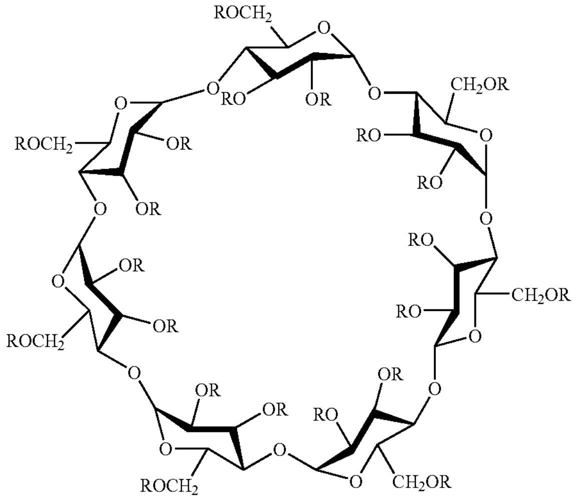

Sulfobutyl Ether-β-Cyclodextrin (Captisol®)

R=$(—H)_{21-n}$ or $(—(CH_2)_4—SO_3Na)_n$
where $n$ = 6.0-7.1

The anionic sulfobutyl ether substituent dramatically improves the aqueous solubility of the parent cyclodextrin. Reversible, non-covalent, complexation of drugs with the CAPTISOL® cyclodextrin generally allows for increased solubility and stability of drugs in aqueous solutions.

A number of references disclose capsule dosage forms comprising a fill composition comprising a cyclodextrin, aqueous or non-aqueous vehicle, active agent and other pharmaceutical excipients.

U.S. Pat. No. 6,287,594 to Wilson et al. and U.S. Pat. No. 6,365, 180 to Meyer et al. disclose oral liquid compositions that can be included in capsule dosage forms. The liquid compositions comprise an acidic active agent, a dispersing agent, a solubilizing agent (0-90% or 60-90% wt.), an optional surfactant (0-10% wt.) and an optional plasticizing agent (0-25% wt.). The dispersing agent can be a carbohydrate-based agent, for example a "derivatized cyclodextrin". The solubilizing agent is water or poly(ethylene glycol). The ratio of active agent to dispersing agent is about 3:1 to about 1:30. The patents do not disclose that the cyclodextrin can reduce or stop dissolution, erosion or degradation of the shell by the aqueous fill composition. Moreover, no examples including a cyclodextrin are disclosed.

U.S. Pat. No. 6,383,471 to Chen et al. discloses a liquid composition comprising an ionizable hydrophobic active agent, ionizing agent, surfactant and optionally solubilizers, triglycerides and neutralizing agents. The liquid composition can be used in capsules. Chen et al. disclose that solubilizers can include cyclodextrins, among many other compounds. A sulfobutyl ether cyclodextrin is listed as an exemplary cyclodextrin. Chen et al. do not disclose or suggest that the cyclodextrin is present in an amount sufficient to reduce or stop dissolution, erosion or degradation of the shell by the aqueous fill composition.

U.S. Pat. No. 6,046,177 and No. 5,874,418 to Stella et al. disclose capsule dosage forms containing a non-aqueous solid physical mixture of an SAE-CD and an active agent. The physical mixture is not a liquid or semi-solid composition and water is not included in the physical mixture in order to reduce the formation of an inclusion complex between the cyclodextrin and the active agent. Stella et al. do not disclose that the cyclodextrin can be present in an amount sufficient to reduce or stop dissolution, erosion or degradation of the shell by water in the fill composition.

U.S. Pat. No. 5,376,645 and No. 5,134,127 to Stella et al. disclose pharmaceutical compositions comprising an active agent, an SAE-CD and a liquid or solid carrier. The SAE-CD and active agent are present as an inclusion complex. Stella et al. generally disclose "soft gelatin capsules wherein the active ingredient (the mixture containing the inclusion complex of SAE-CD and active agent) is mixed with water or oil". They also disclose that, "Pharmaceutical formulations suitable for oral administration wherein the carrier is liquid may conveniently be presented as a solution in an aqueous liquid or a non-aqueous liquid, or as an oil-in-water or water-in-oil liquid emulsion." Stella et al. do not disclose or suggest that an SAE-CD can be present in an aqueous fill composition (for capsules) in an amount sufficient to reduce or stop dissolution, erosion or degradation of the shell by water in the fill composition.

Moreover, Stella et al. disclose combinations wherein the SAE-CD must form an inclusion complex with the active agent.

U.S. Pat. No. 3,426,011 to PARMERTER et al. discloses anionic cyclodextrin derivatives having sulfoalkyl ether substituents. Parmerter et al. do not disclose the use of sulfoalkyl ether cyclodextrins in an aqueous composition contained within a capsule.

Lammers et al. (*Recl. Trav. Chim. Pays-Bas* (1972), 91 (6), 733-742); *Staerke* (1971), 23 (5), 167-71) disclose sulfoalkyl ether derivatized cyclodextrins; however, they do not disclose the use of cyclodextrins to reduce or stop dissolution, erosion or degradation of a shell by an aqueous fill composition.

A need remains for improved capsule fill compositions that stabilize a shell from dissolution, erosion, swelling or degradation by water in the fill composition. None of the art discloses or suggests the invention as claimed herein. The prior art does not disclose an aqueous fill composition for a capsule, wherein the fill composition comprises a derivatized cyclodextrin, such as an SAE-CD, an active agent, and an aqueous carrier, and the derivatized cyclodextrin is present in an amount sufficient to reduce or stop dissolution, erosion, swelling or degradation of the capsule shell by water in the fill composition. Moreover, the prior art does not disclose or suggest a method of stabilizing a water soluble, erodible, swellable or degradable capsule shell surrounding an aqueous fill composition by including a derivatized cyclodextrin in the fill composition.

SUMMARY OF THE INVENTION

The present invention seeks to overcome some or all of the disadvantages inherent in other known formulations. The invention provides a commercially viable composition for use in hard or soft capsules, such that capsules filled with the aqueous fill composition can be prepared and stored without significant degradation, erosion, swelling or dissolution of the capsule shell during the acceptable shelf-life of the filled capsule. The invention provides a capsule dosage form and an aqueous fill composition therefor. The capsule comprises a soft or hard shell. In one aspect, the invention provides a sulfoalkyl ether cyclodextrin (SAE-CD)-based (derivatized cyclodextrin-based) aqueous fill composition. The fill composition comprises an aqueous vehicle, a sulfoalkyl ether cyclodextrin (SAE-CD), an active agent, and optionally other ingredients. The shell is generally made from water soluble, erodible, swellable or degradable material(s); however, a shell material that is not water soluble, erodible, swellable or degradable can also be used. The SAE-CD, or other derivatized cyclodextrin, is present in an amount sufficient to reduce or stop dissolution, erosion, swelling or degradation of the shell by water in the fill composition. In other words, the derivatized cyclodextrin reduces dissolution, erosion, swelling or degradation of the shell by the fill composition as compared to a similar fill composition excluding the derivatized cyclodextrin, i.e., wherein the derivatized cyclodextrin is replaced by water or another non-shell-stabilizing material. In the absence of other shell-stabilizing material (s), the SAE-CD stabilizes the capsule shell against dissolution, erosion, swelling or degradation caused by water in the fill composition.

The capsule dosage form comprises a shell and an aqueous fill composition comprising an SAE-CD, or water soluble derivatized cyclodextrin. In the absence of other shell-stabilizing materials and depending upon the materials that comprise the shell, the fill composition can include at least about 30% by weight of SAE-CD, or derivatized cyclodextrin, based upon the total weight of water and SAE-CD, or derivatized cyclodextrin, present. The amount of derivatized cyclodextrin required to provide the desired level of shell stabilization will vary according to the composition of the shell and the materials comprising the fill composition. The more stable a shell is toward water, the lower the amount of derivatized cyclodextrin that may be required. The less stable the shell is toward water, the greater the amount of derivatized cyclodextrin that may be required. In the absence of other shell-stabilizing materials, the fill composition comprises less than about 70% by weight of water based upon the total weight of water and SAE-CD present. The minimum shelf life of the filled capsule is at least about 1 week, 2 weeks, 3 weeks, 1 month, 3 months, 6 months, or 1 year, or more than about 1 year.

The invention also provides a method of stabilizing a water soluble, erodible or degradable capsule shell surrounding an aqueous fill composition. The method comprises the step of including an SAE-CD, or derivatized cyclodextrin, in the fill composition such that the SAE-CD, or derivatized cyclodextrin, is present in an amount sufficient to reduce or stop the dissolution, erosion, swelling or degradation of the capsule shell caused by the water in the fill composition.

The fill composition can include other shell-stabilizing materials and/or other water activity-reducing materials if desired. The fill composition can also include other ingredients suitable for use in capsule fill compositions.

It is not necessary for the active agent to complex with the derivatized cyclodextrin in order for the derivatized cyclodextrin to exert its stabilizing effect upon the capsule shell. The fill composition can include one or more active agents, and each active agent independently may or may not complex with the derivatized cyclodextrin.

Any shell forming material suitable for use in hard or soft shell capsules or the encapsulation of fill composition can be used in the present invention.

The SAE-CD formulation has a sufficiently high stability for use as a commercial product. The formulation can be prepared as a clear aqueous composition that is sterilizable by sterile filtration (for example, filter pore size of less than or equal to 0.22, UM) and other conventional methods. The aqueous composition is stable under a variety of storage conditions. The SAE-CD can be used to enhance the solubility of active agents by non-covalent ionic binding and/or by complexation via the formation of inclusion complexes.

The fill composition may or may not be clear depending upon the identity and amounts of ingredients included therein. During storage the clarity of the fill composition may or may not change. In other words, one or more components of the fill composition may further dissolve or precipitate during storage. The fill composition, which is a water-containing composition, can be a gel, syrup, fluid, semi-solid, solid, suspension, emulsion, paste, or glassy material.

Accordingly, one aspect of the invention provides an aqueous fill composition in a water erodible, degradable, swellable or soluble shell (or encapsulating material), the fill composition comprising water, one or more derivatized cyclodextrins, optionally one or more active agents and optionally one or more excipients, wherein the derivatized cyclodextrin is present in an amount sufficient to reduce or stop the erosion, degradation, swelling or dissolution of the shell by the fill composition.

Specific embodiments of the invention include those wherein: 1) the derivatized cyclodextrin is SAE-CD and is present in an amount of at least about 30% by wt. based upon the total weight of water and SAE-CD; 2) the fill composition further comprises a shell-stabilizing material; 3) the fill composition has a pH in the range of about 1-11; 4) the fill composition comprises one or more excipients; 5) the shell is a soft shell; 6) the shell is a hard shell; 7) the water activity of the fill composition is less than about 0.95 as measured according to the procedures detailed herein; 8) the fill composition further comprises a solubility-enhancing agent; 9) the SAE-CD complexes with one or more of the active agents; 10) the SAE-CD does not complex with the one or more active agents; 11) the fill composition further comprises a liquid carrier other than water; 12) the fill composition is a liquid; 13) the fill composition is a semi-solid; 14) the fill composition is a solid; 15) the fill composition has been prepared at a temperature at or above 5° C., at or above 25° C., at or above 35° C., at or above 45° C. or at or above 50° C.; 16) the formulation has been prepared at a temperature approximating ambient temperature; 17) the SAE-CD, or derivatized cyclodextrin, reduces the water activity of the aqueous fill composition; 18) the shell is a hard gelatin shell and the fill composition comprises at least 60% wt. of derivatized cyclodextrin; 19) the shell is a soft gelatin shell and the fill composition comprises at least 50% wt. of derivatized cyclodextrin; 20) the shell is a hard shell comprising cellulose, cellulose derivative, starch, starch derivative, or a combination thereof and optionally other excipients, and the fill composition comprises at least 30% wt. of derivatized cyclodextrin; and/or 21) the fill composition further comprises a water activity-reducing material.

The invention also provides a first capsule within a second capsule. In this case the first and/or second capsule can contain the aqueous fill composition.

Another aspect of the invention provides a method of stabilizing an aqueous composition-filled capsule from erosion, dissolution, swelling or degradation of its shell by water present in the fill, the method comprising the step of including in the aqueous fill a derivatized cyclodextrin present in an amount sufficient to reduce or stop the rate of erosion, dissolution, swelling or degradation of the shell by water in the fill composition as compared to the rate of erosion, dissolution, swelling or degradation of the shell by a similar fill composition excluding the derivatized cyclodextrin, i.e., a fill composition wherein the derivatized cyclodextrin is replaced by water or another material that does not stabilize the shell (a non-shell-stabilizing material). The derivatized cyclodextrin is capable of stabilizing the shell against erosion, dissolution, swelling or degradation of the shell by water in the fill composition either in the absence, and optionally presence, of another shell-stabilizing material.

Yet another aspect of the invention provides an aqueous fill composition enclosed within an encapsulating material, the fill composition comprising a derivatized cyclodextrin and an aqueous carrier, wherein the derivatized cyclodextrin is present in an amount sufficient to reduce the water activity of the fill composition thereby reducing the rate of erosion, dissolution, swelling or degradation of the encapsulating material by water in the aqueous fill. The water activity of the fill composition is generally reduced to less than about 0.95±0.025, less than 0.95±0.01, less than 0.925, or less than 0.90. The preferred water activity value may vary according to the components present in the fill and according to the composition of the capsule shell itself. The observed water activity value can also vary according to the instrument used to measure it as well as the calibration of the instrument and reproducibility of measurements (as expressed by standard deviation) taken by the instrument. The preferred water activity value will also vary according to the composition of the shell. Generally, the more water stable the shell, the higher the water activity of the fill composition can be, and the less water stable the shell, the lower the water activity of the fill composition should be, if the fill composition does not contain any other shell-stabilizing material(s).

Specific embodiments of the invention include those wherein: 1) the derivatized cyclodextrin is SAE-CD, HPCD, a water soluble derivatized cyclodextrin capable of reducing the water activity of the fill composition or a mixture thereof; 2) the fill composition further comprises a shell-stabilizing material; 3) the fill composition further comprises a water activity-reducing agent; 4) the fill composition further comprises an active agent; and/or 5) the fill composition further comprises one or more pharmaceutical excipients.

The invention also provides a method of reducing the water activity of an aqueous composition, the method comprising the step of including a water soluble derivatized cyclodextrin in the aqueous composition at a concentration sufficient to reduce the water activity.

The invention also provides capsule formulations that provide active agent release according to a controlled, sustained, extended, slow, rapid, pulsed, timed, targeted, colonic, zero order, pseudo-zero order, first order, pseudo-first order, and/or enteric release profile, wherein release of the active agent begins immediately (less than 30 minutes) or after passage of a delay period (≧30 min) after exposure to an environment of use. In other words, initial release of drug can be immediate or delayed as well as being released according to the modified release profiles mentioned herein. The capsule formulation can be a coated capsule, uncoated capsule, osmotic capsule, capsule within a capsule, or multi-layered capsule.

The invention also provides a capsule comprising:

a water soluble, erodible, degradable and/or swellable shell; and an aqueous fill composition comprising water present in an amount sufficient to solubilize, erode, degrade and/or swell the shell, one or more active agents, and a water soluble cyclodextrin derivative present in an amount sufficient to suppress dissolution, erosion, degradation or swelling of the shell by water in the fill composition, wherein the capsule has a shelf-life of at least one week.

Another embodiment of the invention provides a stabilized capsule formulation having a shelf-life of at least one week, the formulation comprising:

a water soluble, erodible, swellable and/or degradable shell, and an aqueous fill composition comprising a water soluble cyclodextrin derivative, an aqueous carrier and optionally one or more active agents; wherein, the capsule formulation has an increased shelf life as compared to a similar capsule formulation excluding the cyclodextrin derivative and any other shell-stabilizing material; water in the aqueous carrier is present in an amount sufficient to at least partially dissolve, erode, swell and/or degrade the shell; and the cyclodextrin derivative is present in an amount sufficient to reduce the rate of or eliminate dissolution, erosion, swelling or degradation of the shell by water in aqueous carrier.

Still another embodiment of the invention provides an aqueous fill composition enclosed within a water soluble, erodible, swellable and/or degradable encapsulating material, the fill composition comprising:

an aqueous carrier present in an amount sufficient to at least partially dissolve, erode, swell and/or degrade the encapsulating material;

a water soluble cyclodextrin derivative present in an amount insufficient to on its own stop dissolution, erosion, swelling and/or degradation of the encapsulating material by the aqueous carrier;

a shell-stabilizing material present in an amount insufficient to on its own stop dissolution, erosion, swelling and/or degradation of the encapsulating material by the aqueous carrier;

optionally, one or more active agents; and optionally, one or more excipients; wherein, the cyclodextrin derivative and the shell-stabilizing material synergistically at least reduce the rate of or stop dissolution, erosion, swelling and/or degradation of the encapsulating material by the aqueous carrier.

In specific embodiments: 1) the aqueous fill composition is water miscible; 2) the active agent is present in a therapeutically effective amount; 2) the active agent is present in a sub-therapeutically effective amount; 3) the active agent is sparingly soluble, slightly soluble, very slightly soluble, practically insoluble or insoluble in water; 4) the active agent is more soluble in the aqueous fill composition than it is in water; 5) the active agent is soluble, freely soluble or very soluble in water; 6) the active agent complexes with the derivatized cyclodextrin to form an inclusion complex and/or a non-covalent ionic complex; 7) the active agent is selected from the active agents or therapeutic categories disclosed herein; 8) the fill composition further comprises alcohol; 9) the fill composition further comprises a water miscible hydroxy moiety-containing material, e.g., poly-ol, glycol, polymeric glycol, alcohol, or saturated glycolized glycerides, PEG 660 12-hydroxystearate (SOLUTOL™-15); 10) the water soluble cyclodextrin derivative is present in an amount sufficient to solubilize the active agent when it is released into an environment of use, such as the gastrointestinal tract or an aqueous fluid.

Other features, advantages and embodiments of the invention will become apparent to those skilled in the art by the following description, accompanying examples.

BRIEF DESCRIPTION OF THE FIGURES

The following drawings are part of the present specification and are included to further demonstrate certain aspects of the invention. The invention may be better understood by reference to one or more of these drawings in combination with the detailed description of the specific embodiments presented herein.

DETAILED DESCRIPTION OF THE INVENTION

Figure 1:
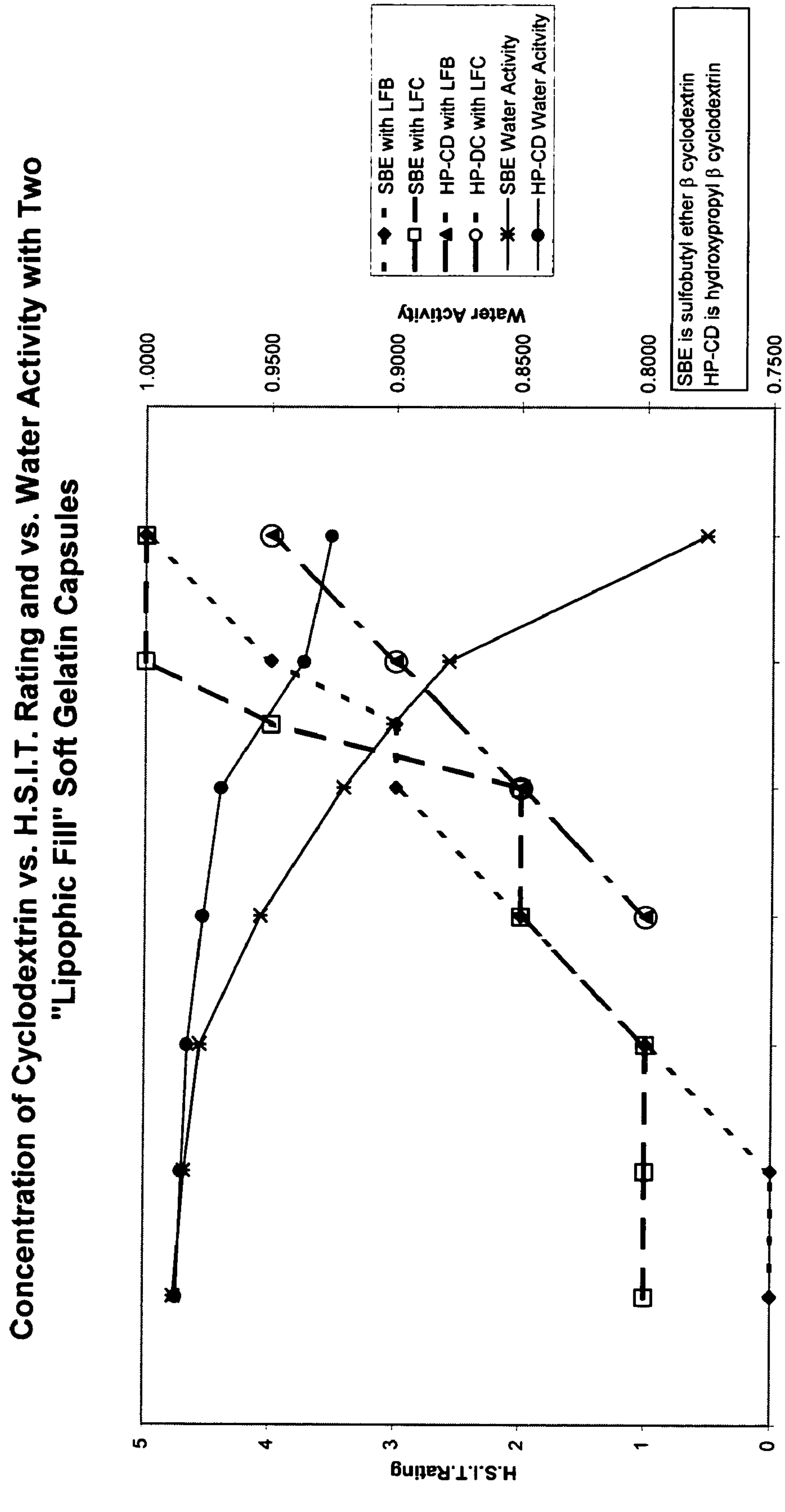
FIG. 1 depicts a graph of concentration of derivatized cyclodextrin (SBE-CD or HPCD) present in a fill composition versus H.S.I.T. rating for soft gelatin capsules LFB (lipophilic fill shells from Banner) and LFC (lipophilic fill shells from Cardinal) containing the fill composition versus water activity of the fill composition.

As used herein, the term "aqueous fill composition" according to the invention means a composition that is used as a fill for a capsule or other encapsulated dosage form, e. g., a coated dosage form, and that contains water and SAE-CD, wherein the water is present in an amount of at least about 10%, 15%, 17%, or 20% wt. of the fill composition. In the absence of a water soluble cyclodextrin derivative, such as SAE-CD, the water is present in an amount sufficient to at least partially erode, dissolve, degrade and/or swell the shell of the capsule to the point that the capsule will not be stable for at least a predetermined shelf-life. The fill composition can be a liquid, solution, suspension, dispersion, microemulsion, particulate mass, emulsion, gel, glass, semi-solid, syrup, cream, meltable solid or solid. In the absence of other shell-stabilizing materials and depending upon the materials comprising the shell, the fill composition can contain up to about 70% by weight of water with respect to the total weight of the fill composition, and the balance of the fill composition comprises a water soluble cyclodextrin derivative, optionally one or more active agents, optionally a water-activity-reducing agent, optionally a shell-stabilizing material, and optionally one or more excipients. In some specific embodiments, the aqueous fill composition is water miscible. Accordingly, the water soluble cyclodextrin derivative suppresses the ability of water in the aqueous fill composition to degrade, erode, dissolve or swell the shell.

The table below depicts the results of preliminary stability studies performed on soft gelatin shells by exposure to aqueous fill compositions. The samples were prepared according to Example 1 and contained varying amounts of water and SAE-CD.

| [SAE-CD] (% wt.) | Capsule Type (Banner) | Time for failure | Observations | Increase in shell size |
|---|---|---|---|---|
| 40% | LFB | 3 days | shape intact | 2.5× |
| | HFB | 3 days | shape intact | 2× |

-continued

| [SAE-CD] (% wt.) | Capsule Type (Banner) | Time for failure | Observations | Increase in shell size |
|---|---|---|---|---|
| 50% | LFB | 7 days | Deformed | 2.5 × original |
| | HFB | 16 days | Slightly deformed | 2.5 × original |
| 55% | LFB | 10 days | Deformed | 2 × original |
| | HFB | 10 days | Deformed | 2 × original |
| 60% | LFB | ≧21 days | Slight widening | no change in length |
| | HFB | ≧21 days | No change | no change |

LFB denotes a shell made for a lipophilic fill.
HFB denotes a shell made for hydrophilic fill.

According to the above data, soft gelatin shells obtained from BANNER PHARMACAPS containing less than 40% by wt. SAE-CD were unstable under the conditions tested. As the concentration of SAE-CD was increased, the stability of the shell toward the fill composition increased. Soft gelatin capsules containing ≧50% wt. SAE-CD were stable for at least one week. Those containing ≧55% wt. SAE-CD were stable for at least ten days, and those containing ≧60% wt. were stable for at least three weeks. Applicants note that capsules having an approximately one-week shelf-life are suitable for use in pharmacies that compound active prior to use.

The same tests were performed on gelatin capsules obtained from CARDINAL HEALTH. The results are detailed in the table below.

| [SAE-CD] (% wt.) | Capsule Type (Cardinal) | Time for failure | Observations | Increase in shell size |
|---|---|---|---|---|
| 40% | LFC | 4 days | shape intact | >3 × original |
| | HFC | 4 days | deformed | 3 × original |
| 50% | LFC | 7 days | deformed | 2 × original |
| | HFC | 7 days | shape intact | 2 × original |
| 55% | LFC | ≧14 days | No deformities | Slightly enlarged |
| | HFC | ≧14 days | No deformities | No change |
| 60% | LFC | >21 days | no change | no change |
| | HFC | >21 days | no change | no change |

LFC denotes a shell made for a lipophilic fill.
HFC denotes a shell made for hydrophilic fill.

According to the above data, soft gelatin shells obtained from CARDINAL HEALTH containing less than 40% by wt. SAE-CD were unstable under the conditions tested. As the concentration of SAE-CD was increased, the stability of the shell toward the fill composition increased. Soft gelatin capsules containing ≧50% wt. SAE-CD were stable for at least one week. Those containing ≧55% wt. SAE-CD were stable for at least two weeks, and those containing ≧60% wt. were stable for at least 21 days.

Soft gelatin capsules are stabilized from dissolution, erosion, swelling or degradation by water in the fill composition by including in the composition SAE-CD present in an amount of 50% wt. or more based upon the total weight of water and SAE-CD or upon the total weight of the fill composition, so that the capsules have a shelf-life of at least one week. Higher concentrations of SAE-CD result in longer shelf-life.

HPCD, hydroxypropyl derivatized cyclodextrin, was evaluated under the same conditions described above using the same HFB, LFB, HFC, and LFC soft gelatin capsules. The results are detailed in the table below.

| [HP-CD] (% wt.) | Capsule Type | Time for failure | Observations | Increase in shell size |
|---|---|---|---|---|
| 40% | LFC | 2 days | Deformed | >3 × original |
| | HFC | 2 days | Deformed | >3 × original |
| | LFB | 2 days | Deformed | >3 × original |
| | HFB | 2 days | Deformed | >3 × original |
| 50% | LFC | 4 days | Shape intact | 2 × original |
| | HFC | 4 days | shape intact | 2 × original |
| | LFB | 4 days | shape intact | 2 × original |
| | HFB | 4 days | shape intact | 2 × original |
| 60% | LFC | 7 days | Slight deformity | 2 × original |
| | HFC | 7 days | Slight deformity | 2 × original |
| | LFB | 7 days | Shape intact | 2 × original |
| | HFB | 7 days | Shape intact | 2 × original |
| 70% | LFC | 14 days | Shape intact | 1.5 × original |
| | HFC | 14 days | Shape intact | 1.5 × original |
| | LFB | 14 days | Shape intact | 1.5 × original |
| | HFB | 14 days | Shape intact | 1.5 × original |

Soft gelatin capsules are stabilized from dissolution, erosion, swelling or degradation by water in the fill composition by including in the composition HPCD present in an amount of 60% wt. or more based upon the total weight of water and HP-CD, so that the capsules have a shelf-life of at least one week. Higher concentrations of HPCD result in longer shelf-life.

FIG. 1 depicts a chart of the relationship between concentration of derivatized cyclodextrin, H.S.I.T. (HALF-SHELL integrity test) rating and water activity. SBE (sulfobutyl ether cyclodextrin having a degrees of substitution (DS) of about 6.5-7.5), when present at an amount of about ≧50% wt., provided at least a one week stability for LFB and LFC soft gelatin capsules. Likewise HPCD (hydroxypropyl cyclodextrin having a degrees of substitution (DS) of about 5.5), when present at an amount of about ≧60% wt., provided at least a one-week stability for LFB and LFC soft gelatin capsules.

Figure 2:
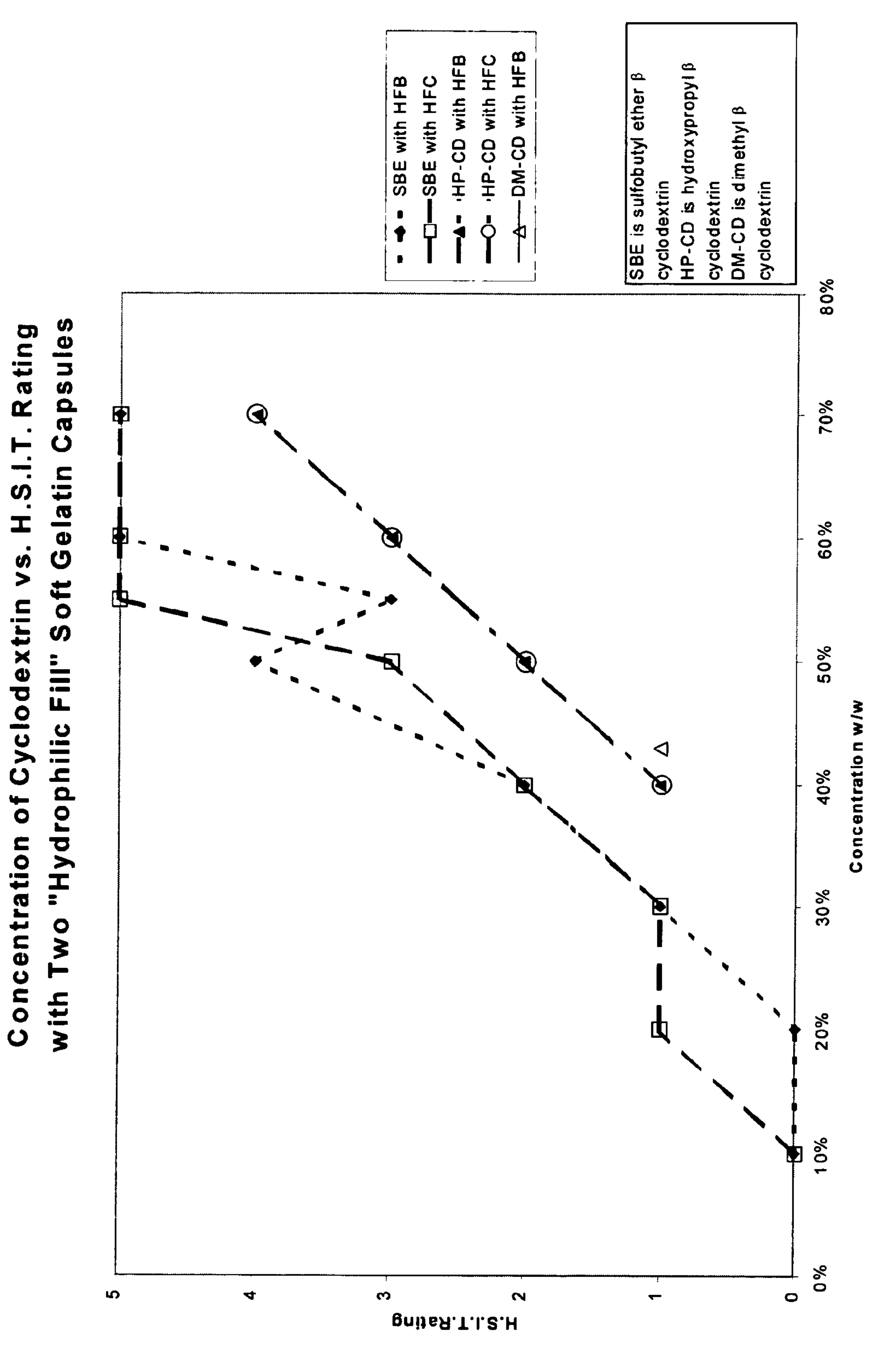
FIG. 2 depicts a graph of concentration of cyclodextrin present in a fill composition versus H.S.I.T. rating for soft gelatin capsules HFB (hydrophilic fill shells from Banner) and HFC (hydrophilic fill shells from Cardinal) containing the fill composition versus water activity of the fill composition.

FIG. 2 depicts a chart of the relationship between concentration of derivatized cyclodextrin and H.S.I.T. (HALF-SHELL integrity test) rating. SBE (sulfobutyl ether cyclodextrin having a degrees of substitution (DS) of about 6.5-7.5), when present at an amount of about ≧50% wt. , provided at least a one week stability for LFB and LFC soft gelatin capsules. Likewise HPCD (hydroxypropyl cyclodextrin having a degrees of substitution (DS) of about 5.5), when present at an amount of about ≧60% wt., provided at least one week stability for LFB and LFC soft gelatin capsules. The maximum achievable concentration of DMCD was about 42% wt., and at that concentration, it only slightly increased the stability of the shell.

Figure 3:
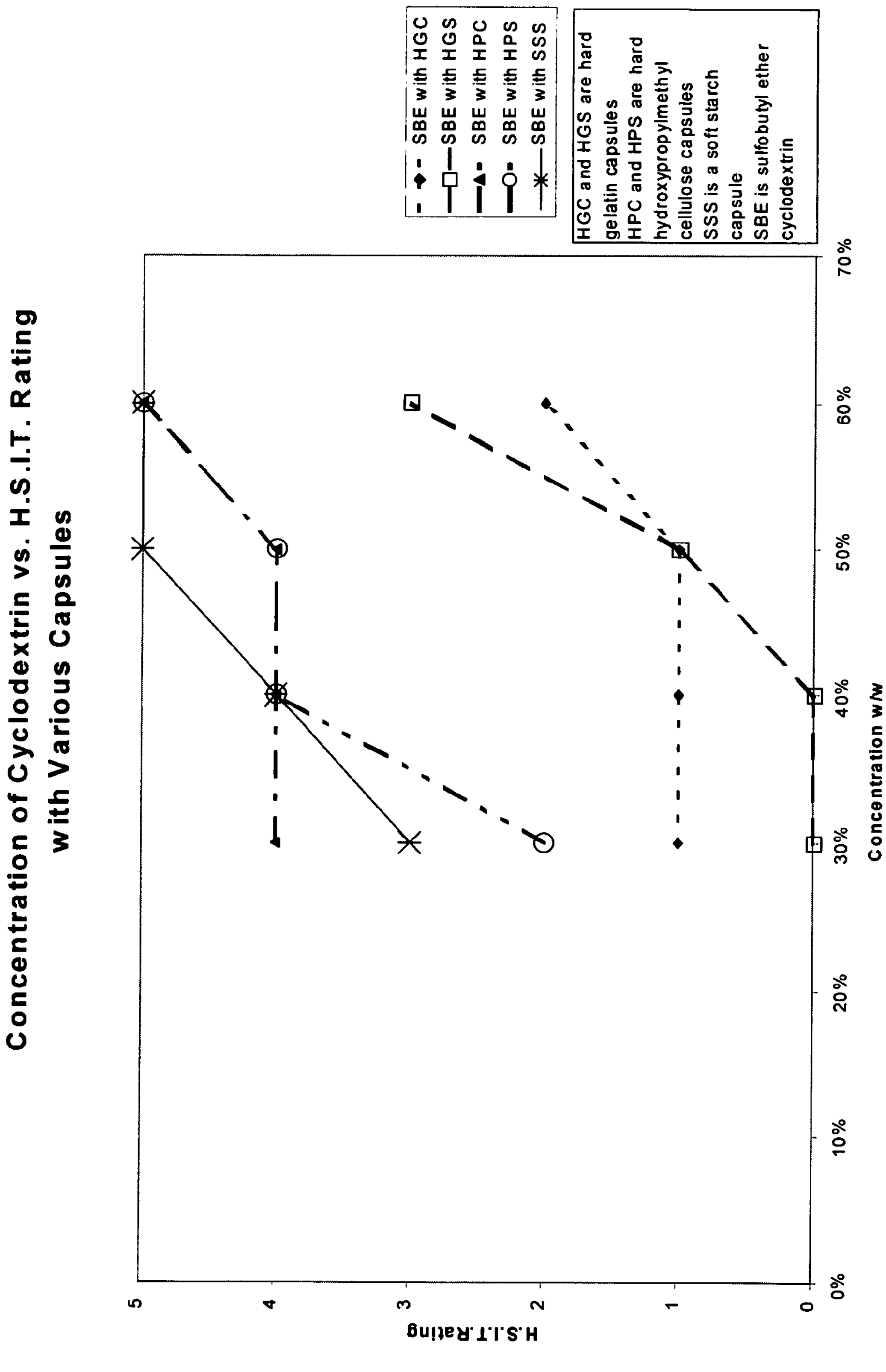
FIG. 3 depicts a graph of concentration of cyclodextrin present in a fill composition versus H.S.I.T. rating for various different capsule shells HGC (hard gelatin capsule from Capsugel), HGS (hard gelatin capsule from Shionogi), HPC (hard hydroxypropyl methylcellulose capsule from Capsugel), HPS (hard hydroxypropyl methylcellulose capsule from Shionogi), SSS (soft starch capsule from Swisscaps).

FIG. 3 depicts a chart of the relationship between concentration of SBE cyclodextrin and H.S.I.T. (HALF-SHELL integrity test) rating for HGC (hard gelatin capsule From CAPSUGEL), HGS (hard gelatin capsule from SHIONOGI), HPC (hard hydroxypropyl methylcellulose shell from CAPSUGEL), and HPS (hard hydroxypropyl methylcellulose shell from SHIONOGI), and SSS (soft starch shell SWISSCAPS). The stability obtained was dependent upon the composition of the capsule gel. For hard gelatin capsules, SBE concentration of about ≧60% wt. provided at least a one-week stability. For hard hydroxypropyl methylcellulose capsules, SBE concentration of about 240% wt. provided at least a two-week stability. For soft starch capsules, SBE concentration of about ≧30% wt. provided at least a one-week stability.

Figure 4:
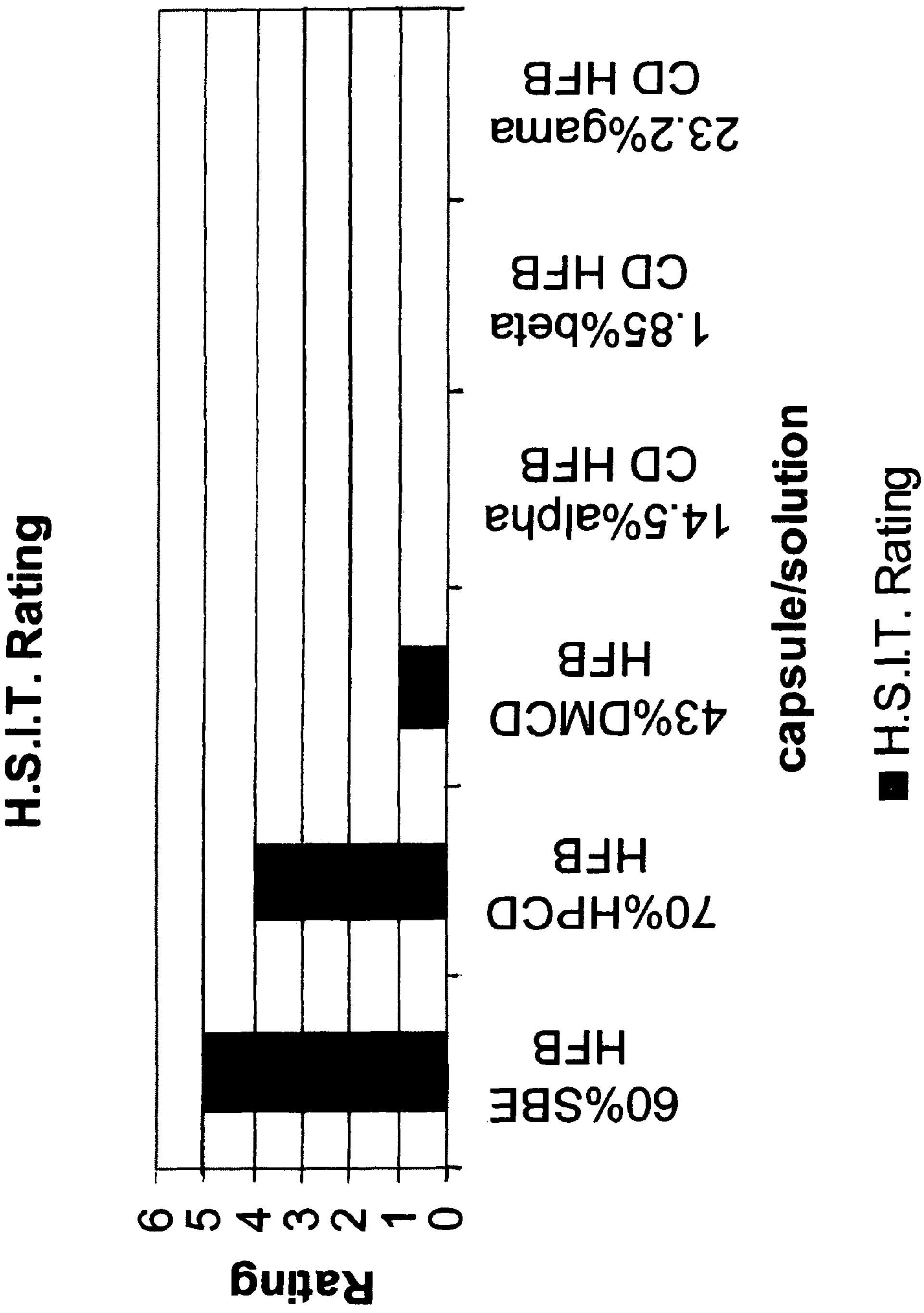
FIG. 4 depicts a graph of H.S.I.T. rating of various different aqueous fill compositions comprising different cyclodextrins and cyclodextrin derivatives when placed in contact with a hydrophilic fill soft gelatin capsule.

The parent cyclodextrins have limited water solubility as compared to SAE-CD and HPCD. Underivatized α-CD has a water solubility of about 14.5% w/w at saturation. Underivatized (β-CD has a water solubility of about 1.85% w/w at saturation. Underivatized γ-CD has a water solubility of about 23.2% w/w at saturation. At these concentrations, these parent cyclodextrins are unable to stabilize the soft gelatin capsules from dissolution, erosion, swelling or degradation by water in the fill composition. Dimethylcyclodextrin (DMCD) forms a 43% w/w aqueous solution at saturation. At this concentration, DMCD is unable to stabilize the soft gelatin capsules from dissolution, erosion, swelling or degradation by water in the fill composition. FIG. 4 depicts a chart of the relationship between H.S.I.T. rating and concentration of these cyclodextrins as present in a fill composition exposed to a soft gelatin capsule.

Hard shell capsules and soft shell capsules differ in their thickness, amount of cross-linking, rigidity, composition, shape and other ways. Accordingly, an aqueous fill composition suitable for filling a soft shell capsule might not be suitable for filling a hard shell capsule and vice versa. That said, an artisan will be able to select the appropriate and approximate initial conditions for concentration of derivatized cyclodextrin in the fill composition by following the selection/evaluation procedures described herein, especially in Example 2.

Two types of hard shell capsules obtained from CAPSUGEL were evaluated. A conventional hard gelatin capsule (HCAP) and a hard HPMC (hydroxypropyl methylcellulose) capsule (VCAP) were evaluated under identical conditions using aqueous solutions differing in the concentration of SBE-CD (sulfobutyl ether cyclodextrin). Results from the evaluation are included in the table below.

| Soln | capsule | failure time | observations | size |
|---|---|---|---|---|
| 30% SBE | hardcap | 24 hrs | deformed/bends | 2 × length |
| | vcap | >14 days | | |
| 40% SBE | hardcap | 48 hrs | deformed/closed | >2 × width |
| | vcap | >14 days | | |
| 50% SBE | hardcap | 48 hrs | deformed/closed | 2 × width |
| | vcap | >14 days | | |
| 60% SBE | hardcap | 4 days | closed/stuck | 2 × width |
| | vcap | >14 days | | |

In the absence of SBE or another shell-stabilizing material, these shell materials were unstable to erosion, dissolution, swelling and degradation by water. Under the conditions of the assay, SBE cyclodextrin was able to stabilize the VCAP shells for ≧14 days even at concentrations of ≧30% wt. of the fill composition. In this assay, monitoring was discontinued after fourteen days.

Without being held bound to a particular mechanism, it is believed that the increasing the concentration of derivatized cyclodextrin present in the aqueous fill composition results in reduced water activity for the fill composition. The table below provides a summary of water activity versus concentration of cyclodextrin derivatives or some shell-stabilizing materials in water at about 20-25° C., or ambient temperature.

| Concentration (% w/w) | Water Activity (approximate values) SBE7-β-CD | HP-β-CD DS = 5.5 | PEG 400 | PVP K17 |
|---|---|---|---|---|
| 0 | 1.00 | 1.00 | 1.00 | 1.00 |
| 10 | ~0.98 | ~0.99 | — | ~0.99 |
| 20 | ~0.98 | ~0.99 | ~0.99 | ~0.99 |
| 30 | ~0.97 | ~0.98 | ~0.97 | ~0.99 |
| 40 | ~0.95 | ~0.98 | ~0.95 | ~0.97 |
| 50 | ~0.91 | ~0.97 | ~0.90 | ~0.95 |
| 55 | ~0.88 | | | |
| 60 | ~0.86 | ~0.94 | ~0.84 | ~0.87 |
| 70 | ~0.76 | ~0.93 | | |

PEG-400 denotes poly(ethylene glycol) having an approximate molecular weight of 400.

The values detailed above are approximate and can vary from instrument to instrument. These values were determined according to the procedure described herein on a water activity meter described herein. The numbers can also vary within the standard deviation of a particular instrument. It is also possible for the numbers to vary according to the accuracy and reproducibility of the instrument used as well as the method for calibrating the instrument with solution standards of known water activity.

Under the test conditions, the water activity of a solution containing dimethyl cyclodextrin (DMCD; 43% wt.; the approximate saturation concentration of DMCD) and water was approximately 0.996. All SAE-CD or HPCD containing fill compositions evaluated were clear.

As depicted in FIG. 1, as the concentration of water soluble derivatized cyclodextrin is increased, the water activity of the fill composition decreases while the H. S.I.T. rating of the fill composition increases. This means that a water soluble derivatized cyclodextrin such as SAE-CD is capable of decreasing the water activity of an aqueous fill composition and consequently increasing the stability (shelf-life) of a shell in contact with the fill composition. For SAE-CD in a soft-gelatin capsule, a fill composition having a water activity of less than about 0.95 or less than about 0.94 provides an increase in the stability of the shell toward the fill composition.

Accordingly, the invention also provides a method of reducing the water activity of an aqueous fill composition in a capsule, the method comprising the step of including a derivatized cyclodextrin in the fill composition in an amount sufficient to reduce the water activity to less than about 0.95±0.015 as determined according to the method and instrument described herein. The standard deviation of reproducibility and accuracy can vary more widely or narrowly depending upon the experimental conditions used to measure the water activity or operator skill. Typically a standard deviation of ±0.02 is permissible. The activity of the water in the fill composition can be reduced by a water soluble derivatized cyclodextrin or a combination of a water soluble derivatized cyclodextrin and one or more other components, such as a shell-stabilizing material or water activity-reducing material.

Figure 5:
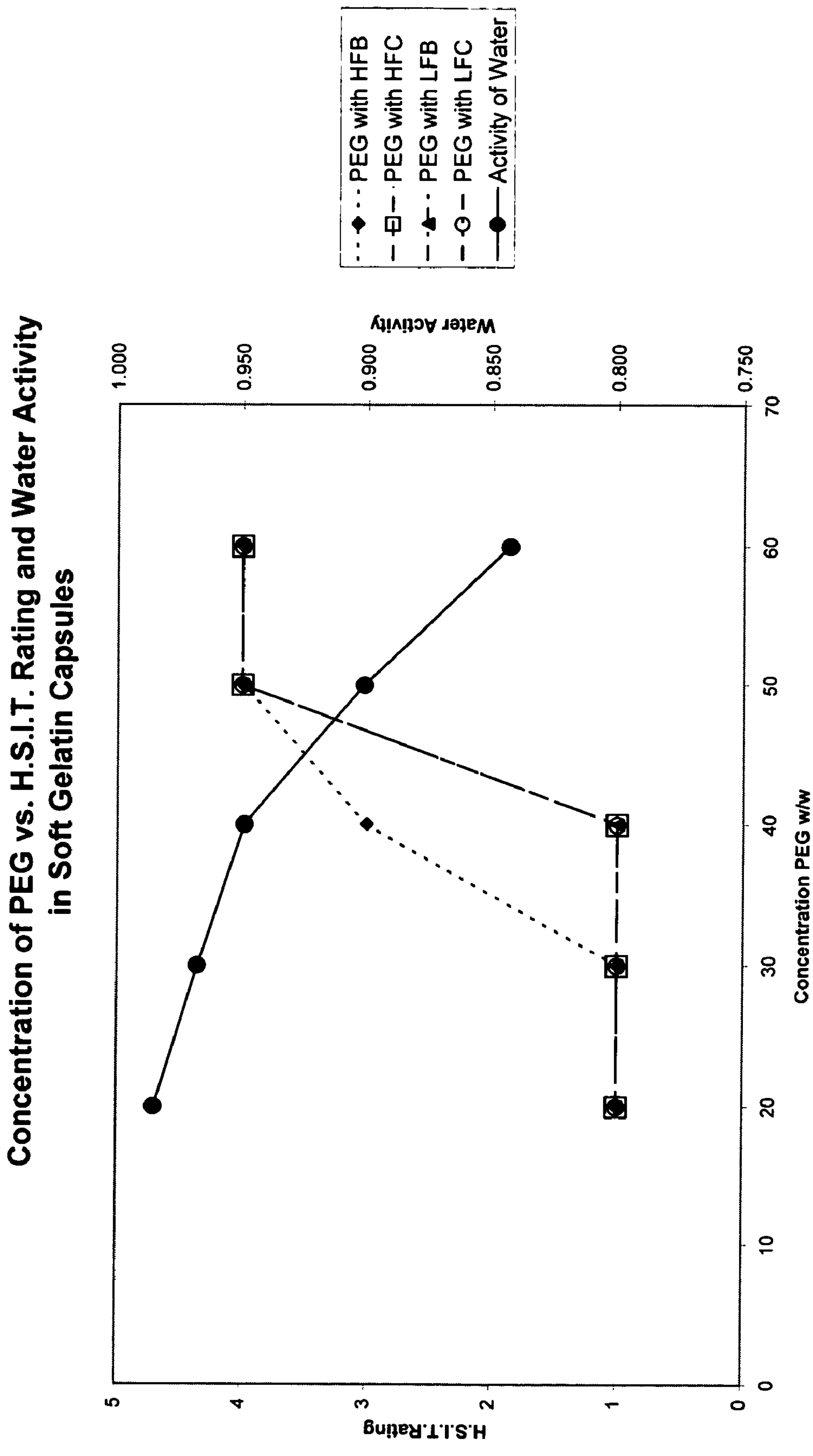
FIG. 5 depicts a graph of concentration of PEG (poly (ethylene glycol)) in a fill composition versus the H.S.I.T. rating of the fill composition for a soft gelatin capsule containing the fill composition and versus the water activity of the fill composition.

PEG is used as a fill material in aqueous fill compositions for capsules and is recognized as a shell stabilizing material. The present inventors believe that, among its other properties, the ability of PEG to reduce water activity is responsible for its usefulness in this fill composition. FIG. 5 depicts a chart of the relationship between concentration of PEG in a fill composition versus the H.S.I.T. rating of the fill composition for a soft gelatin capsule and versus the water activity of the fill composition. As the concentration of PEG is increased, the water activity of the fill composition decreases while the H.S.I.T. rating of the fill composition increases. For PEG in a soft-gelatin capsule, a fill composition having a water activity of less than about 0.95 or less than about 0.9±0.02 provides an increase in the stability of the shell toward the fill composition.

According to the data above, water soluble poly (vinyl pyrrolidone) is an effective water-activity reducing agent.

The maximum amount of water permissible in the fill composition will depend upon the amount of SAE-CD present, the presence or absence of other shell-stabilizing materials and/or water activity-reducing materials, the composition of the shell, the pH of the fill composition, the storage conditions for the capsules, the formulation of the fill composition and other variables.

An aqueous fill composition can comprise a derivatized cyclodextrin, a water activity-reducing agent and an aqueous carrier, wherein the derivatized cyclodextrin and water activity-reducing agent are together present in an amount sufficient to reduce the water activity to less than about 0.95 or less than about 0.90±0.02. In one embodiment, neither the derivatized cyclodextrin nor the water activity-reducing agent is present in an amount sufficient to individually reduce the water activity to the desired value. In other words, the water activity-reducing material and derivatized cyclodextrin together can provide an improved, additive or synergistic enhancement over the shell-stabilizing effect of either material alone.

A water activity-reducing agent is a compound or mixture of compounds capable of reducing the water activity of the fill composition. Increasing the concentration of a water activity-reducing agent in the fill composition causes a decrease in the water activity of the fill composition. A shell-stabilizing material can also serve as a water activity reducing agent. As used herein, a shell-stabilizing material is one or more materials (other than cyclodextrin derivative) included in the fill composition to minimize dissolution, erosion, swelling or degradation of the shell by the aqueous fill composition. Suitable materials include PEG (poly(ethylene glycol); in particular water soluble or water swellable PEG), glycol, polyol, glycerin, propanediol, surfactant, detergent, soap, benzyl alcohol, sugar, salt, thickening agent, hygroscopic agent, equilibrium protecting agent, deliquescent agent, hydrogenated glucose syrup (lycasin), mannitol, triacetin, tetraglycol, PVP (in particular water soluble or water swellable PVP) and combinations thereof. One or more shell-stabilizing materials can be used in combination with one or more derivatized cyclodextrins in the fill composition. Likewise, one or more water activity-reducing materials can be used in combination with one or more derivatized cyclodextrins in the fill composition.

When a shell-stabilizing material is present, it can be present in an amount insufficient to, on its own, stabilize the shell from degradation, erosion, dissolution or swelling by water in the fill composition. In other words, when another shell-stabilizing material is present, the derivatized cyclodextrin may need to be present in order to stabilize the shell from dissolution, erosion, swelling or degradation by water from the fill composition.

Likewise, when a shell-stabilizing material and derivatized cyclodextrin are present, the derivatized cyclodextrin can be present in an amount insufficient to, on its own, stabilize the shell. In other words, the derivatized cyclodextrin would also need the shell-stabilizing material in order to stabilize the shell. In the absence of a shell-stabilizing material, the derivatized cyclodextrin will be able to stabilize the shell on its own provided the derivatized cyclodextrin is present in an amount sufficient to do so. The invention also includes embodiments wherein each is present in an amount sufficient to, on its own, stabilize the shell as described herein.

Figure 6A:
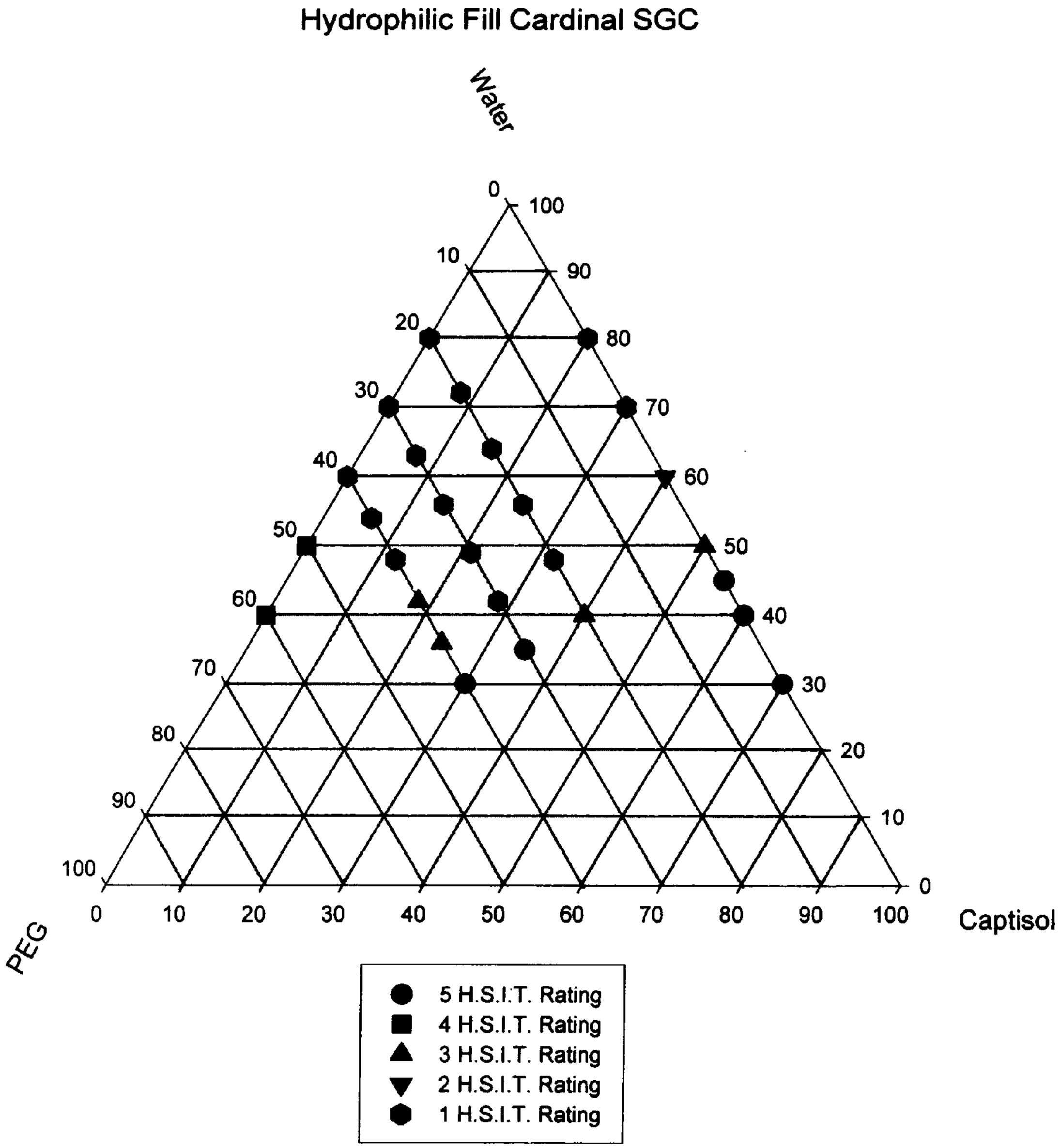
FIGS. 6*a*-6*b* depict ternary graphs of cyclodextrin concentration, PEG concentration and water concentration versus H.S.I.T. rating for soft gelatin capsules recognized by their manufacturers as being suitable for use with a hydrophilic fill composition.
Figure 6B:
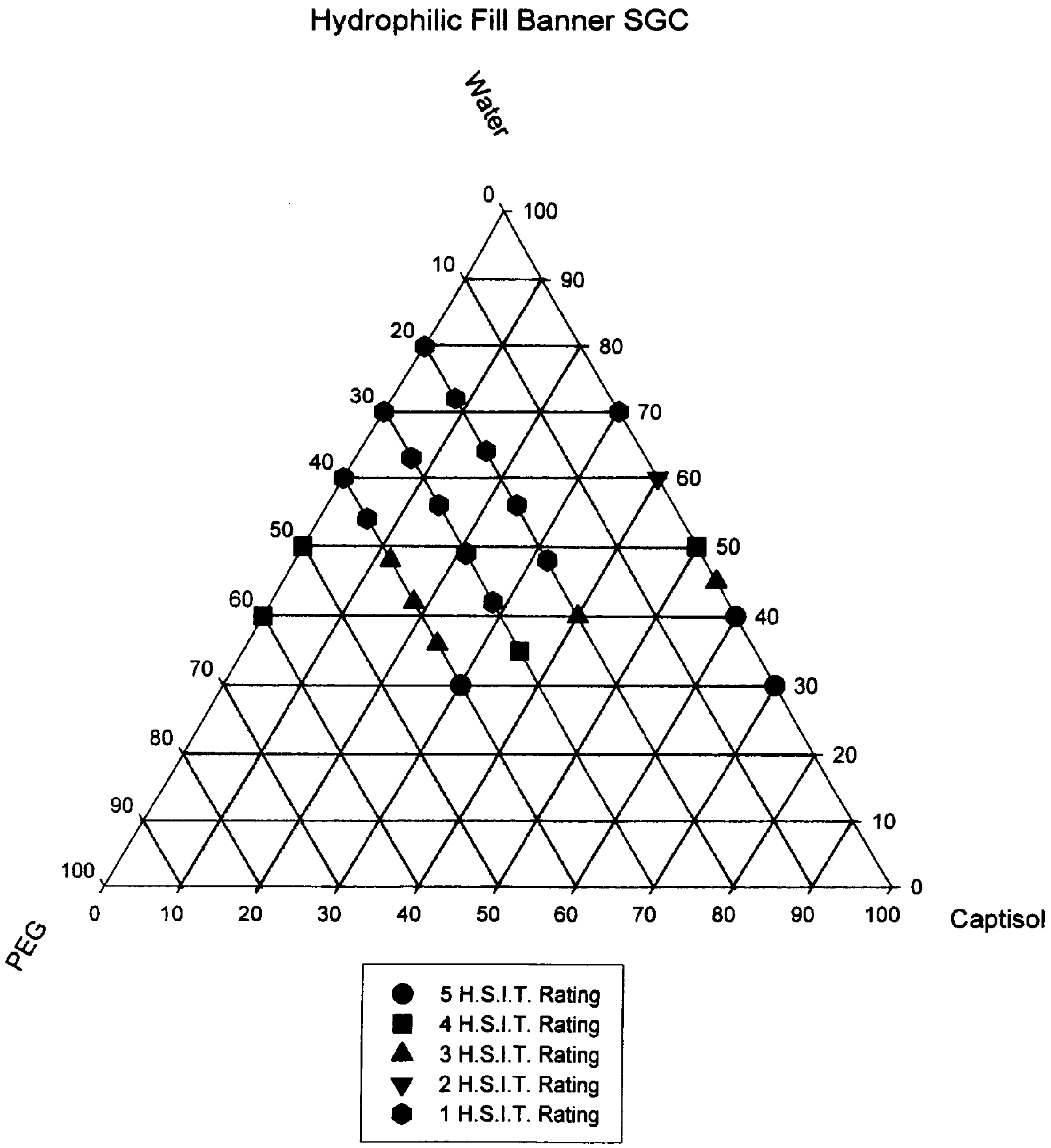
Figure 7A:
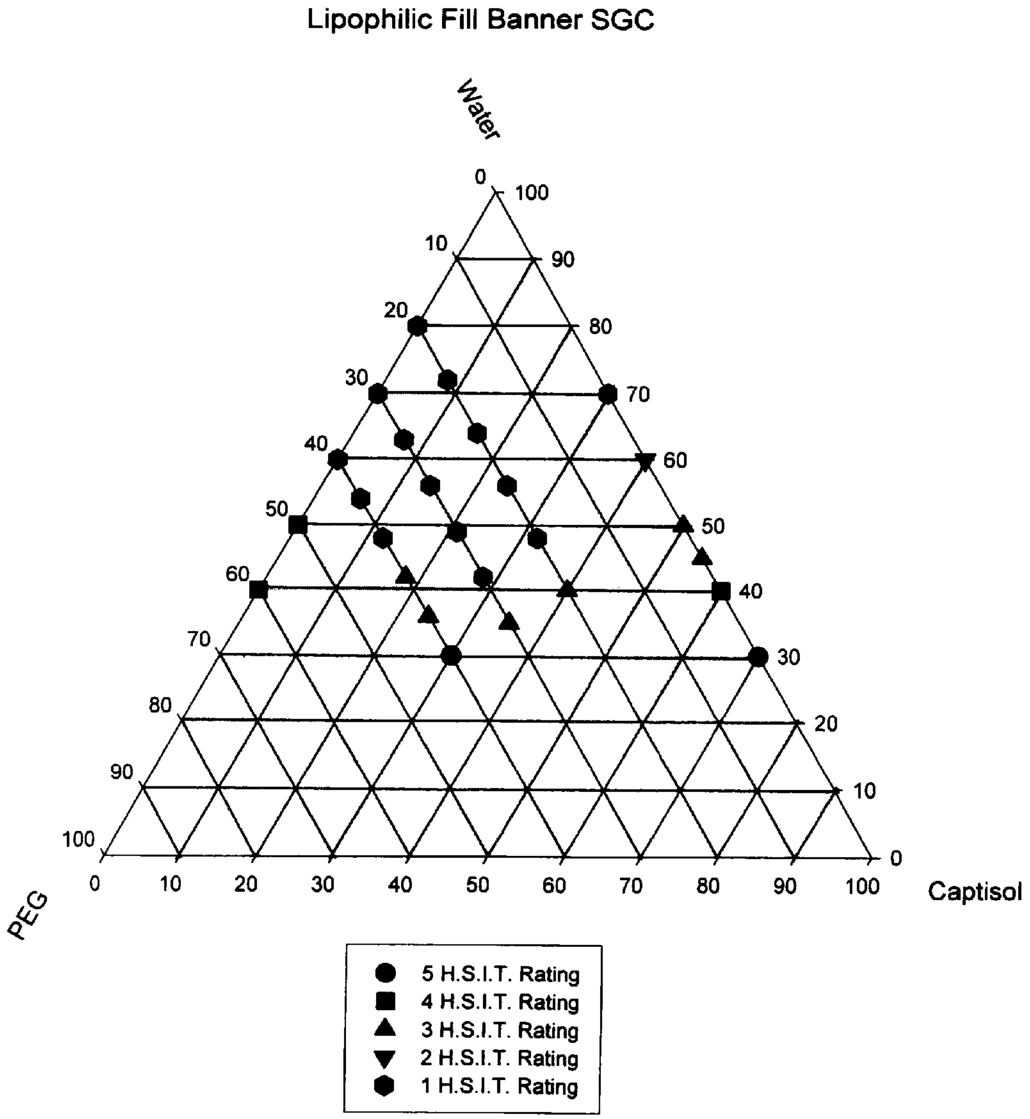
FIGS. 7*a*-7*b* depict ternary graphs of cyclodextrin concentration, PEG concentration and water concentration versus H.S.I.T. rating for soft gelatin capsules recognized by their manufacturers as being suitable for use with a lipophilic fill composition.
Figure 7B:
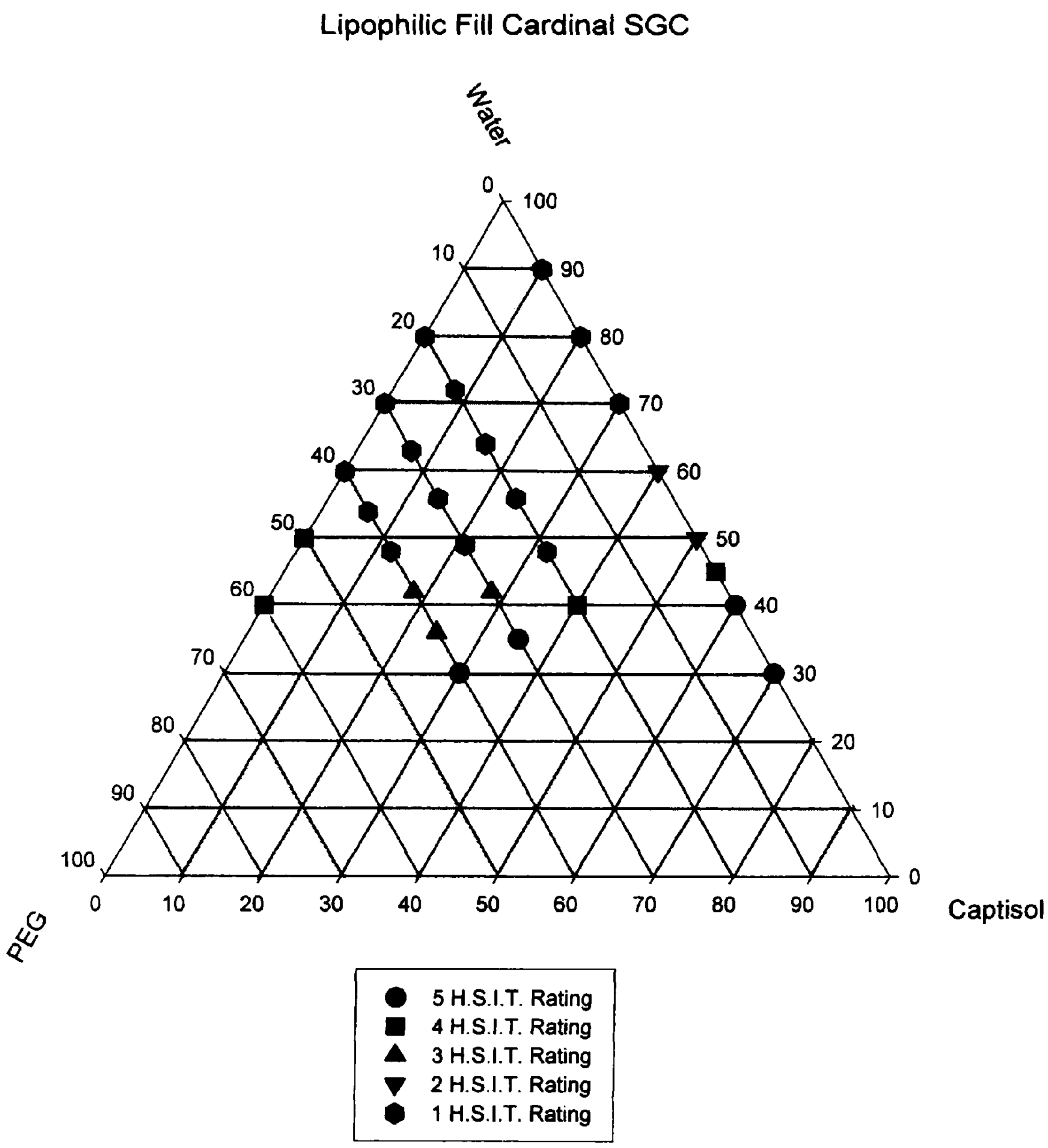

It has been discovered that PEG has a beneficial effect upon the shell-stabilizing property of an aqueous fill composition comprising SAE-CD. FIG. 6*a* depicts a ternary graph correlating the concentration of SAE-CD, water and PEG in a fill composition to the H.S.I.T. rating of a soft shell capsule exposed to the fill composition. Aqueous fill solutions comprising differing amounts of PEG, SAE-CD and water were prepared. The stability tests were conducted as described below. The HFC soft gelatin capsules described herein were used. For a composition comprising 40% wt. SBE-CD, 40% wt. water and 20% wt. PEG, the shell was stable for greater than 5 days. For a composition comprising 35% wt. SBE-CD, 35% wt. water and 30% wt. PEG, the shell was stable for greater than 5 days. For a composition comprising 18% wt. SBE-CD, 42% wt. water and 40% wt. PEG, the shell was stable for greater than 5 days. Under each of the conditions tested, the control sample excluded SAE-CD, i.e., containing only water and PEG at the indicated concentration, and failed within 24 hours. About the same results were obtained for the HFB (FIG. 6*b*), LFB (FIG. 7*a*) and LFC (FIG. 7*b*) soft gelatin capsules. Increasing the SAE-CD concentration to values higher than those indicated further increases the shelf-life of the shell or provides an HSIT rating of at least 4. Stabilized aqueous fill composition-containing capsule formulations can be achieved with each capsule if the following fill compositions are used.

| CAPSULE | SAE-CD (%) | PEG + SAE-CD (%) | Water (%) |
|---|---|---|---|
| HFC | ≧18 | ≧50 | ≦50 |
| HFB | ≧12 | ≧52 | ≦48 |
| LFB | ≧18 | ≧50 | ≦50 |
| LFC | ≧18 | ≧52 | ≦48 |

Figure 8:
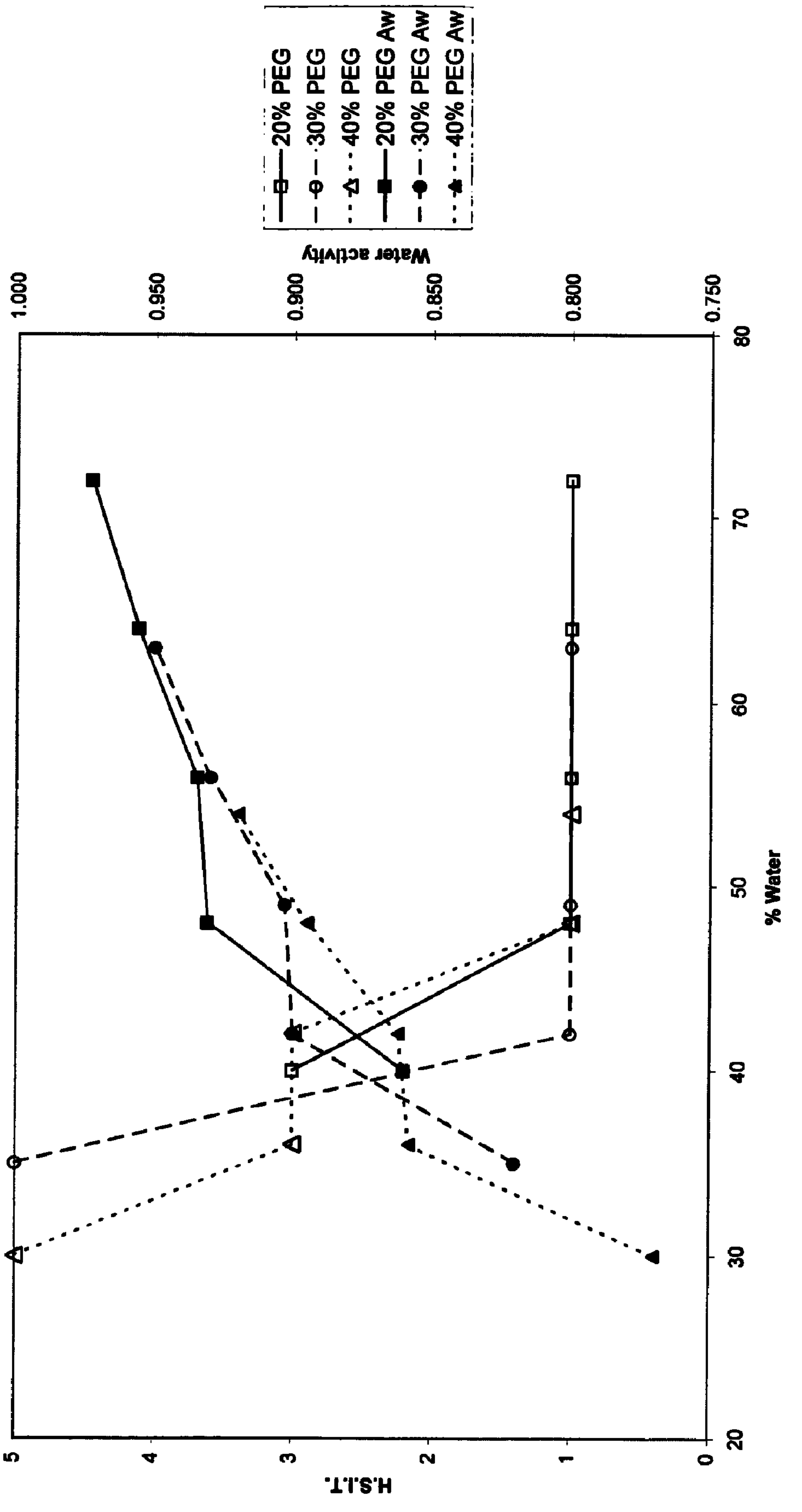
FIG. 8 depicts a graph of concentration of water in a fill composition comprising SBE versus the H.S.I.T. rating of the fill composition for a soft gelatin capsule containing the fill composition and versus the water activity of the fill composition. The different lines represent different concentrations of PEG.

FIG. 8 depicts a graph of correlating the concentration of water of a fill composition versus the H.S.I.T. rating of a soft gelatin capsule exposed to the fill composition versus water activity of the fill composition. The data of FIG. 8 is a different expression of the same data of FIG. 6*b*. The fill composition comprises water, SBE-CD and PEG, and the fill composition was made by mixing PEG with an aqueous SBE-CD-containing solution. The concentration of water is expressed as the concentration of water in the entire fill composition. Based upon the results detailed in FIG. 8, a fill composition comprising SBE-CD, PEG and water will form a stable soft gelatin capsule formulation as long as the water activity of the fill composition is about ≦0.90±0.02.

Specific embodiments of A capsule containing an aqueous fill composition comprising water, SAE-CD and PEG can be prepared according to invention by employing the following criteria:

1. Water comprises ≦50% of the fill composition, and the combination of SAE-CD, PEG, one or more optional excipients and one or more optional active agents comprises ≧50% of the fill composition; wherein SAE-CD can comprise up to 90% (85%, 83%, or 80%) of the weight of the fill composition, and PEG can comprise less than 90%, respectively, of the weight of the fill composition, provided that PEG ≧45% when SAE-CD comprises ≦5 % of the weight of the fill composition, and when PEG ≦45% then SAE-CD ≧18%, wherein both PEG (preferably water soluble or water swellable) and SAE-CD are present.

2. Water comprises ≦45% of the fill composition, and the combination of SAE-CD, PEG, one or more optional excipients and one or more optional active agents comprises ≧50% of the fill composition; wherein SAE-CD can comprise up to 90% (85%, 83%, or 80%) of the weight of the fill composition, and PEG can comprise less than 90%, respectively, of the weight of the fill composition, provided that PEG ≧45% when SAE-CD comprises ≦5% of the weight of the fill composition, and when PEG ≦45% then SAE-CD ≧10%, wherein both PEG (preferably water soluble or water swellable) and SAE-CD are present.

Accordingly, the invention provides a method of increasing the shelf-life of a capsule formulation containing an aqueous fill composition comprising an aqueous carrier and first shell-stabilizing material present in an amount insufficient to, on its own, stabilize the shell from erosion, dissolution, degradation or swelling, the method comprising the step of including a derivatized cyclodextrin in the fill composition. By so doing, the first shell-stabilizing material and derivatized cyclodextrin cooperate to improve the shelf-life of the capsule formulation. This can be done even when the derivatized cyclodextrin is present in an amount insufficient to, on its own, stabilize the shell from erosion, dissolution, degradation or swelling by the aqueous fill composition.

When either one or both of the derivatized cyclodextrin and the other shell-stabilizing material (or water activity-reducing agent) is present in an amount that, on its own, is insufficient to stabilize the shell, then the cyclodextrin and the other shell-stabilizing material (or water activity-reducing agent) cooperate to synergistically stabilize the shell.

The invention also provides a water-stabilized capsule formulation comprising a water soluble, erodible, swellable and/or degradable shell, and an aqueous fill composition comprising a derivatized cyclodextrin and an aqueous carrier, wherein the capsule formulation has an increased shelf life as compared to a similar capsule formulation excluding the derivatized cyclodextrin.

Figure 9:
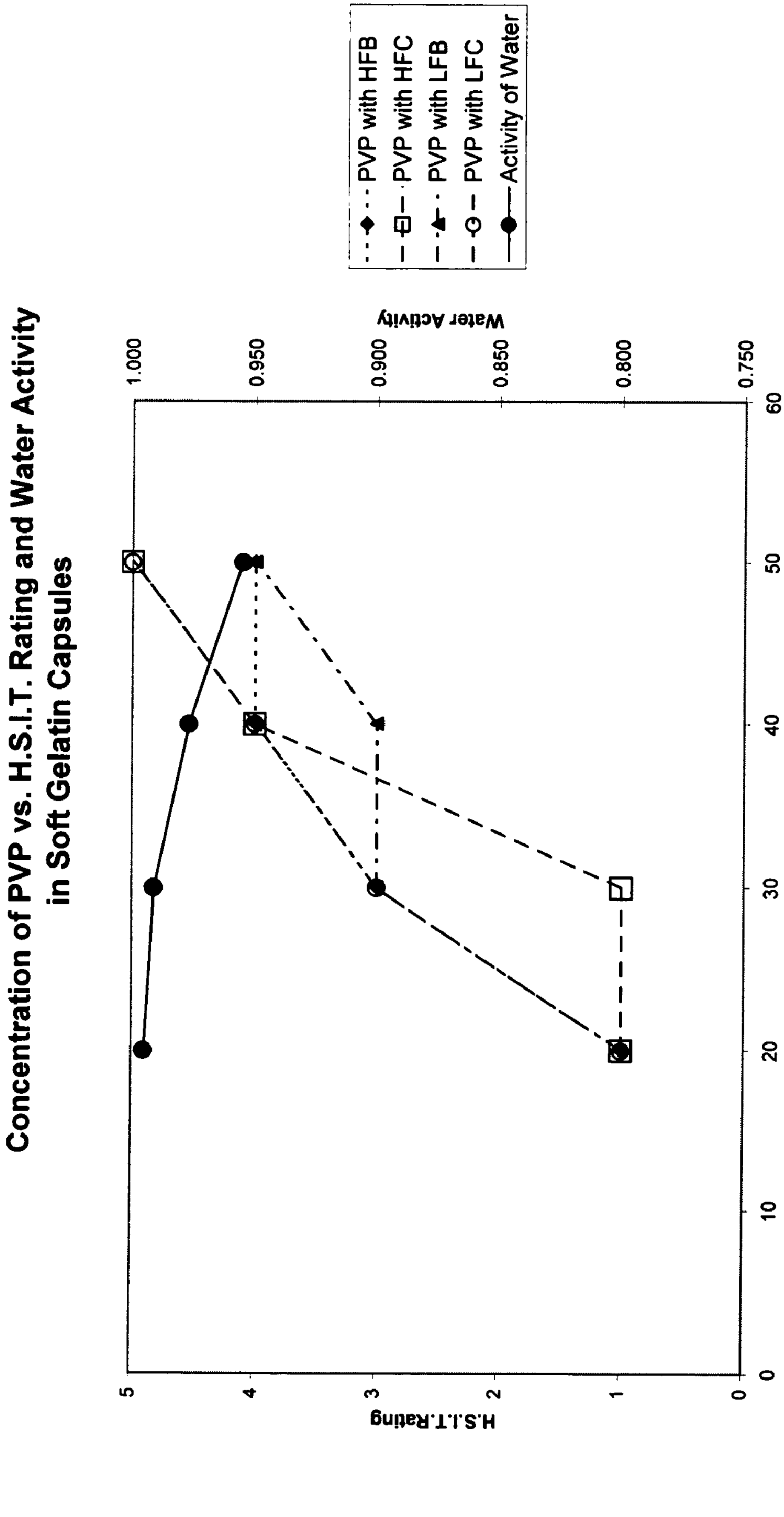
FIG. 9 depicts a graph of concentration of poly (vinyl pyrrolidone) (PVP) in a fill composition versus the H.S.I.T. rating of the fill composition for a soft gelatin capsule containing the fill composition and versus the water activity of the fill composition.

Surprisingly, PVP can on its own (in the absence of a derivatized cyclodextrin) also stabilize a shell exposed to an aqueous fill composition. FIG. 9 depicts a graph correlating the concentration of water soluble PVP in a fill composition versus the H.S.I. T. rating of a soft gelatin capsule exposed to the fill composition and the water activity of the fill composition. The data indicate that an aqueous fill composition comprising at least about 25-30% wt. of PVP can stabilize a shell from water in the fill composition. A solution containing 25-30% wt of PVP has a water activity of approximately ≦0.996± the standard deviation. Accordingly, the invention also provides a method of stabilizing a shell material from erosion, dissolution, swelling or degradation by water in an aqueous fill composition, the method comprising the step of including water soluble PVP in the fill composition in an amount sufficient to stabilize the shell.

Figure 10A:
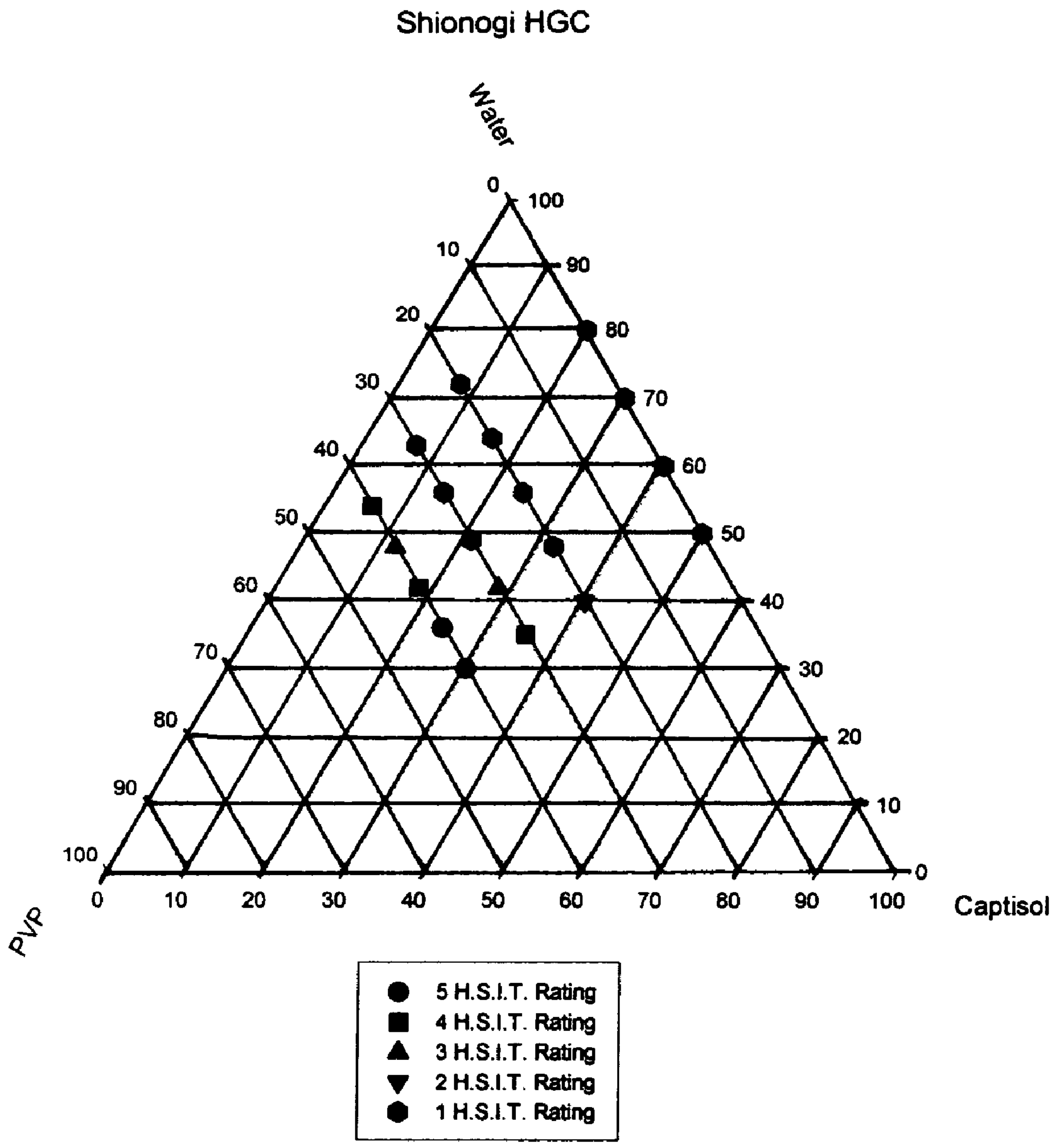
FIGS. 10A-10I depict ternary graphs of cyclodextrin concentration, PVP concentration and water concentration versus H.S.I.T. rating for various different capsules.
Figure 10B:
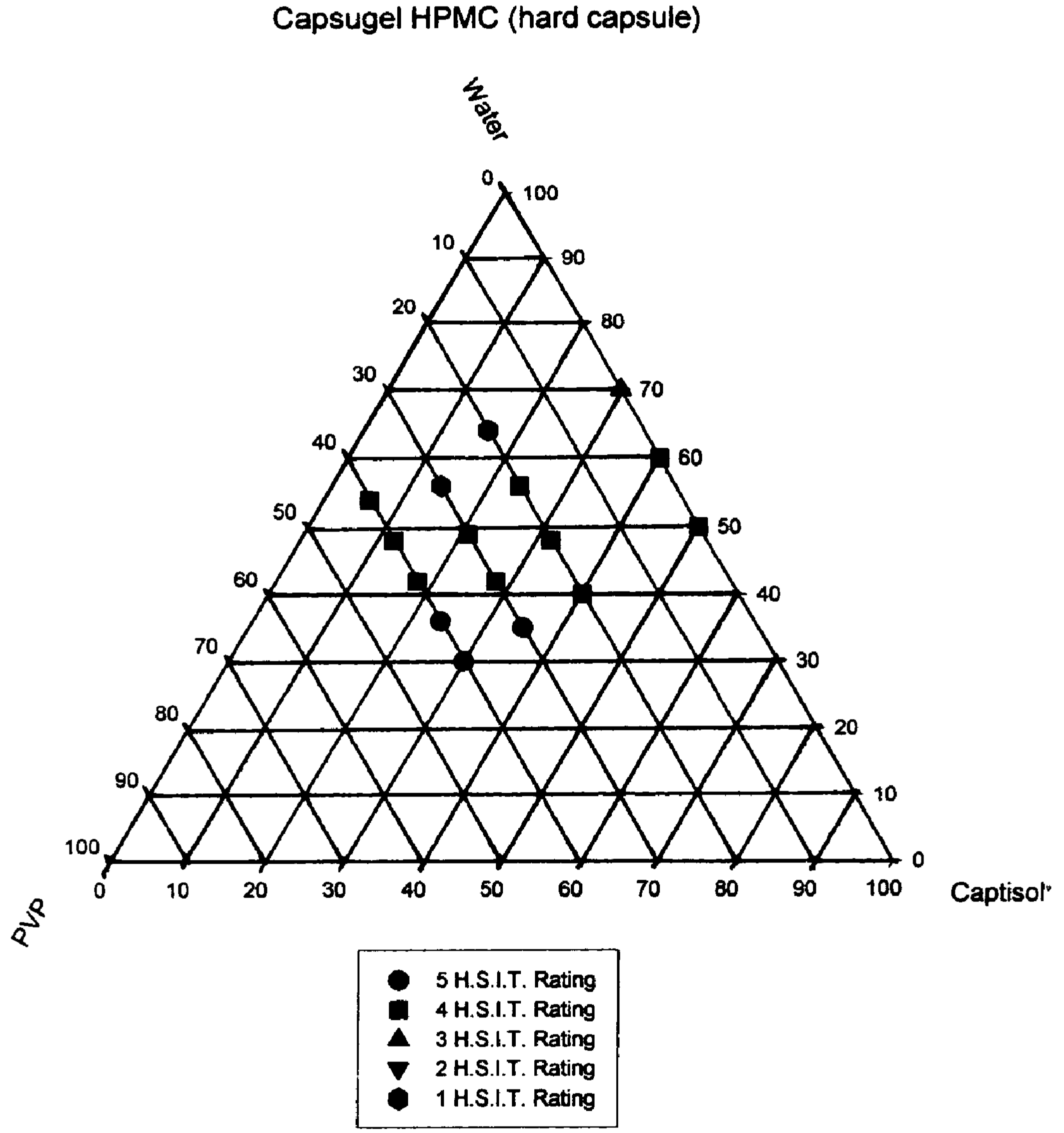
Figure 10C:
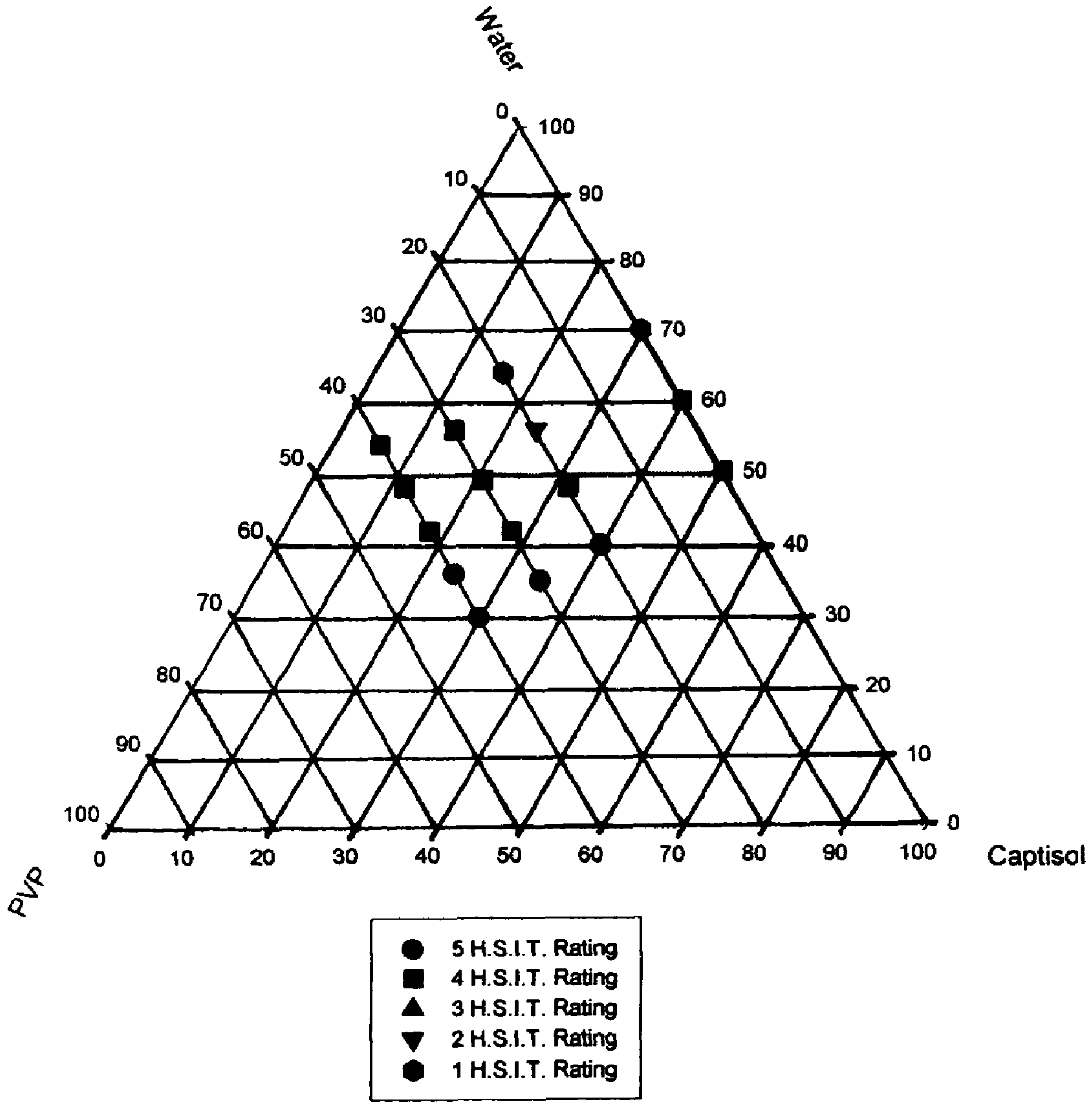
Figure 10D:
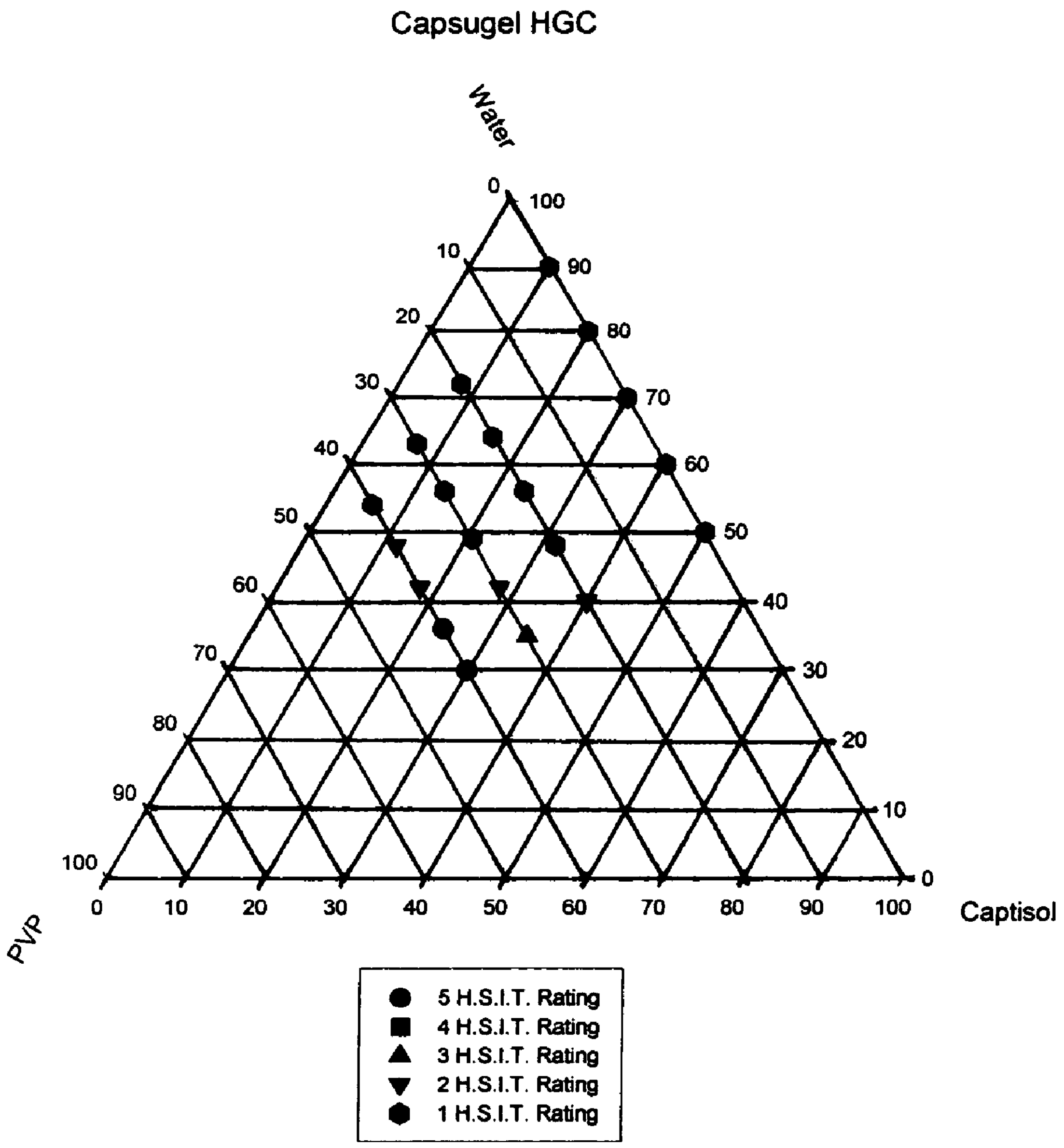
Figure 10E:
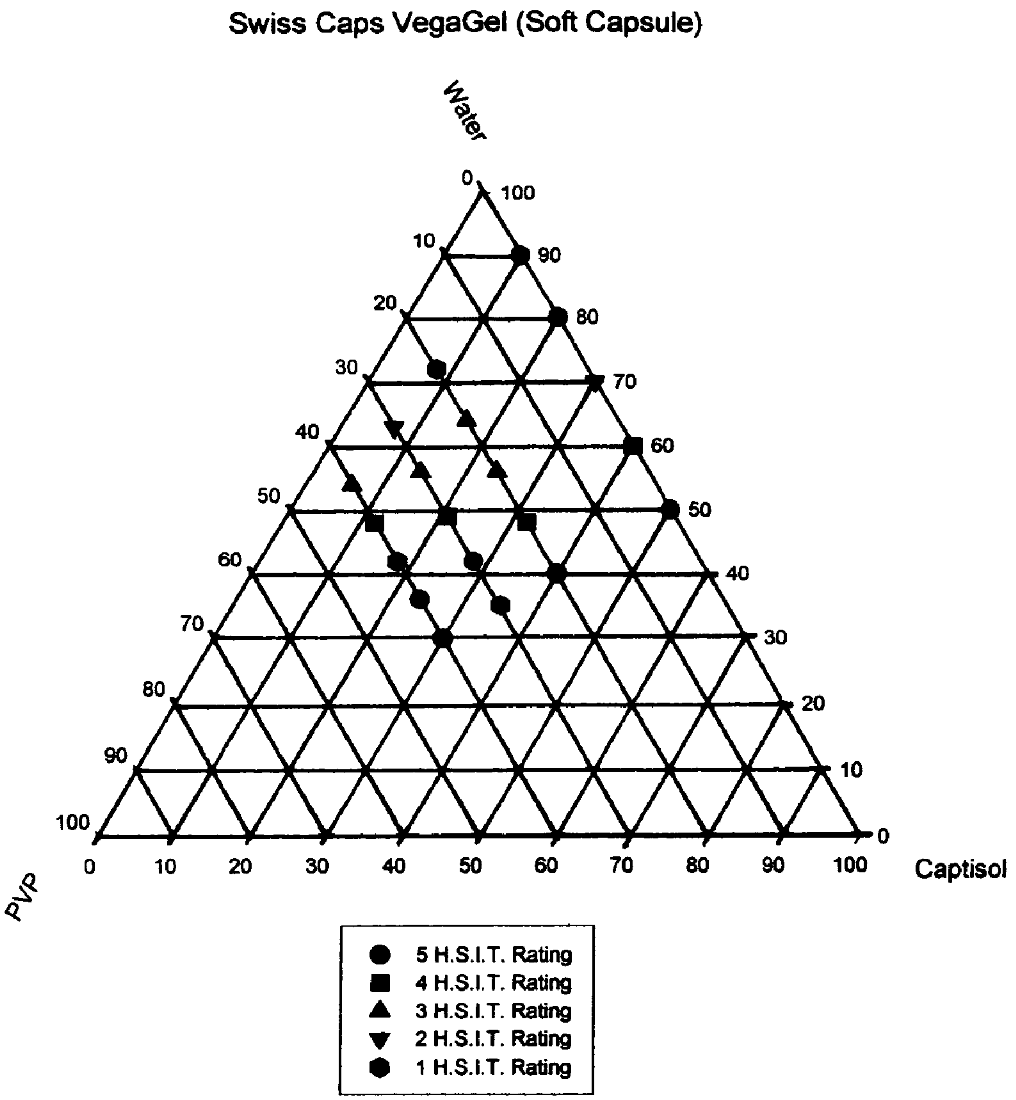
Figure 10F:
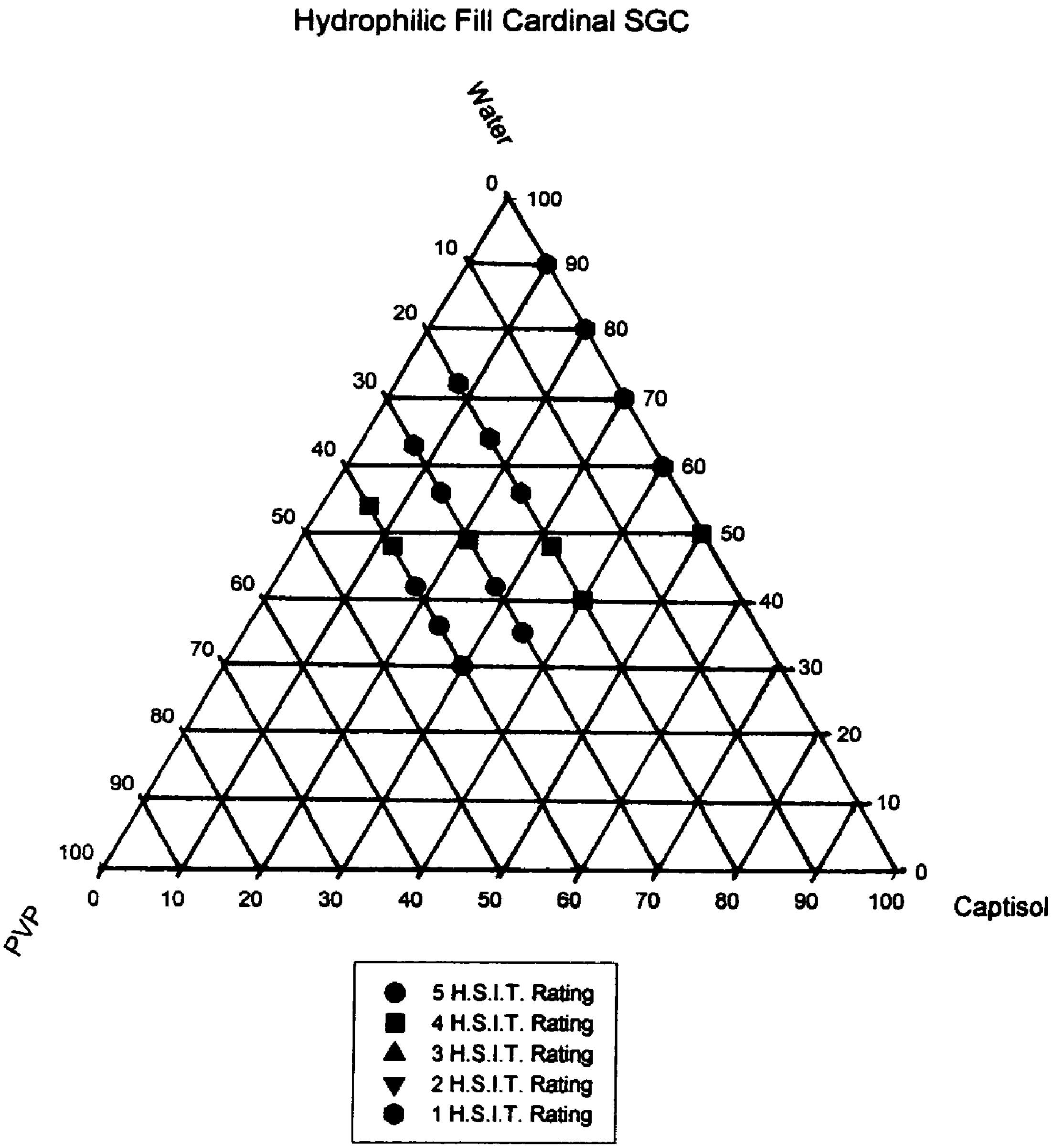
Figure 10G:
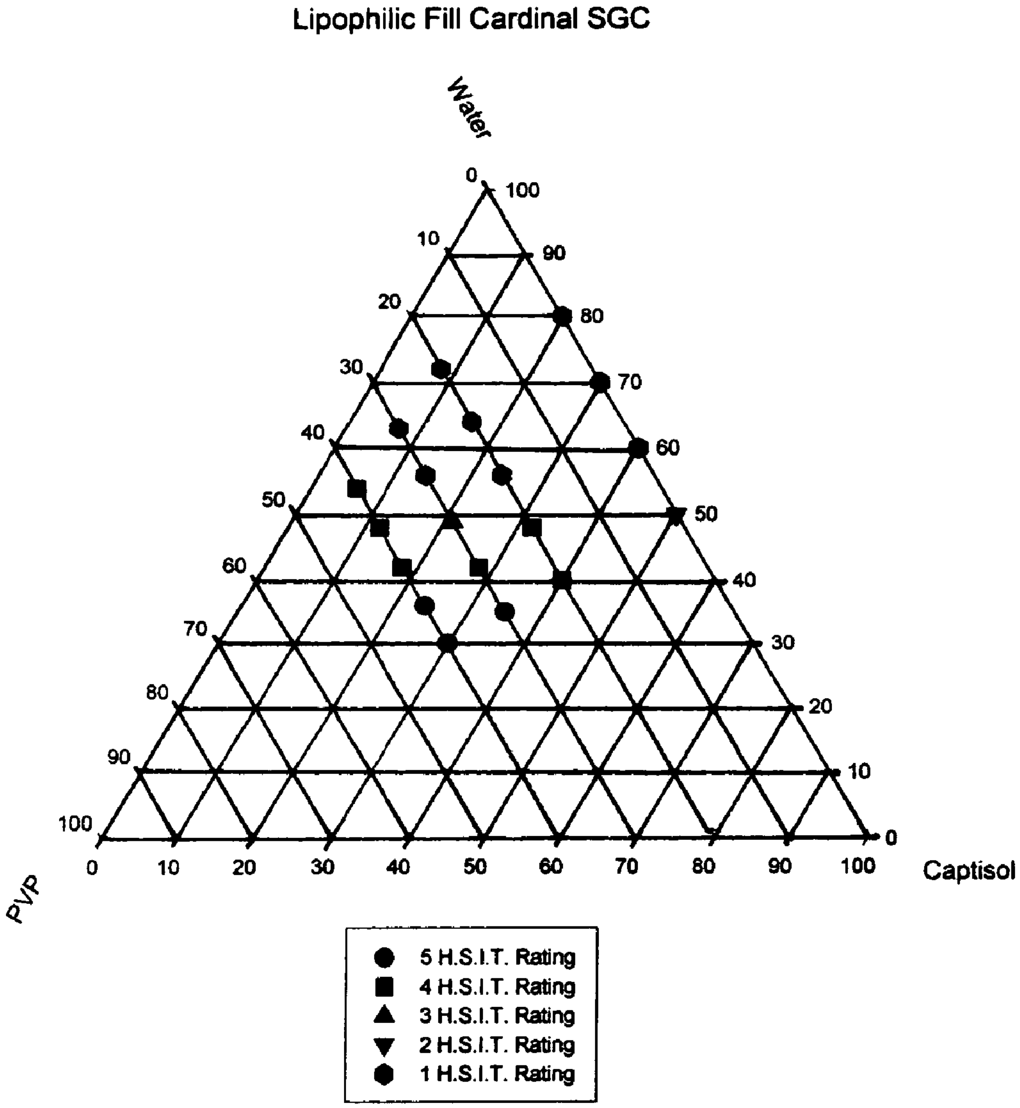
Figure 10H:
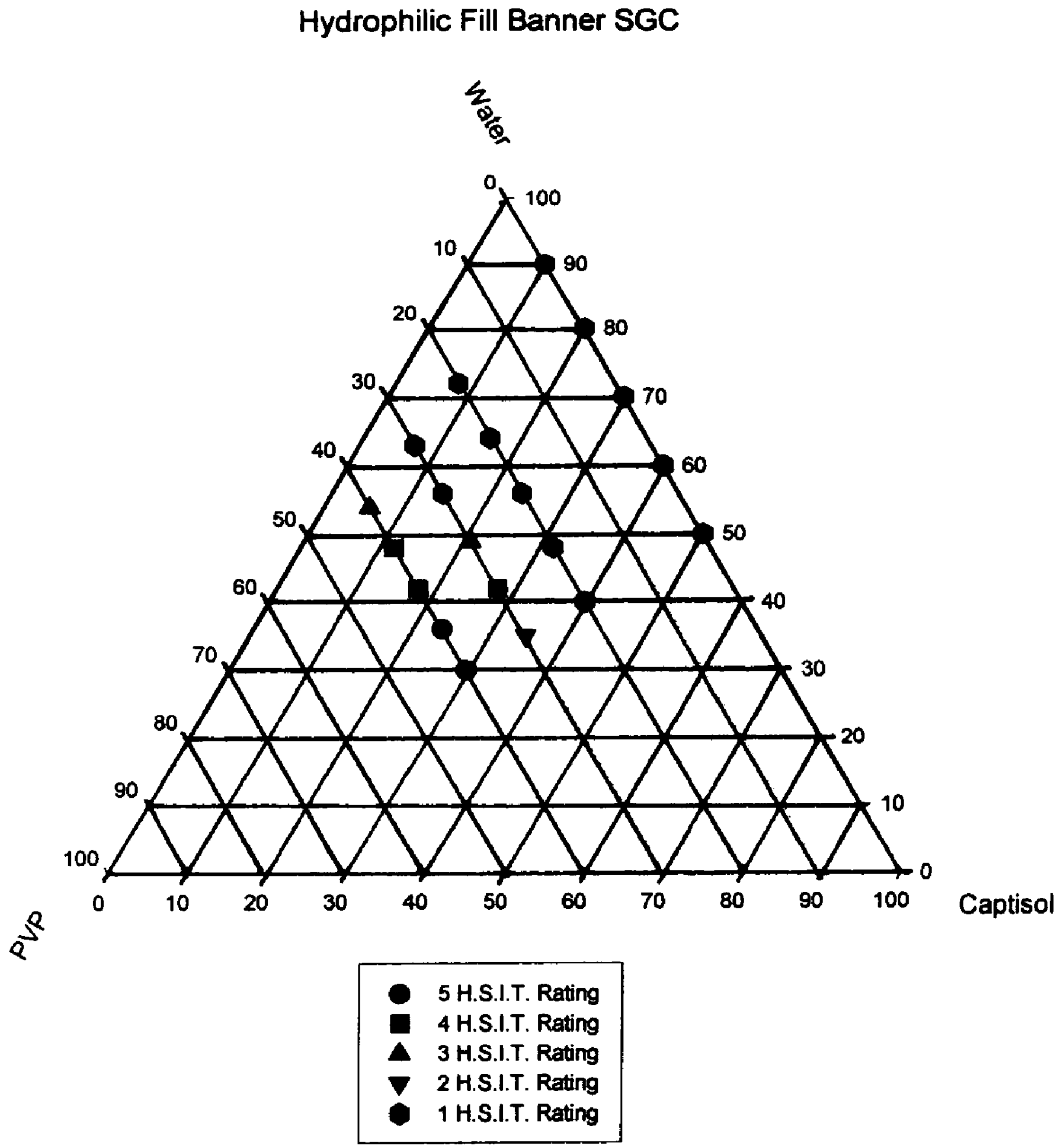
Figure 10I:
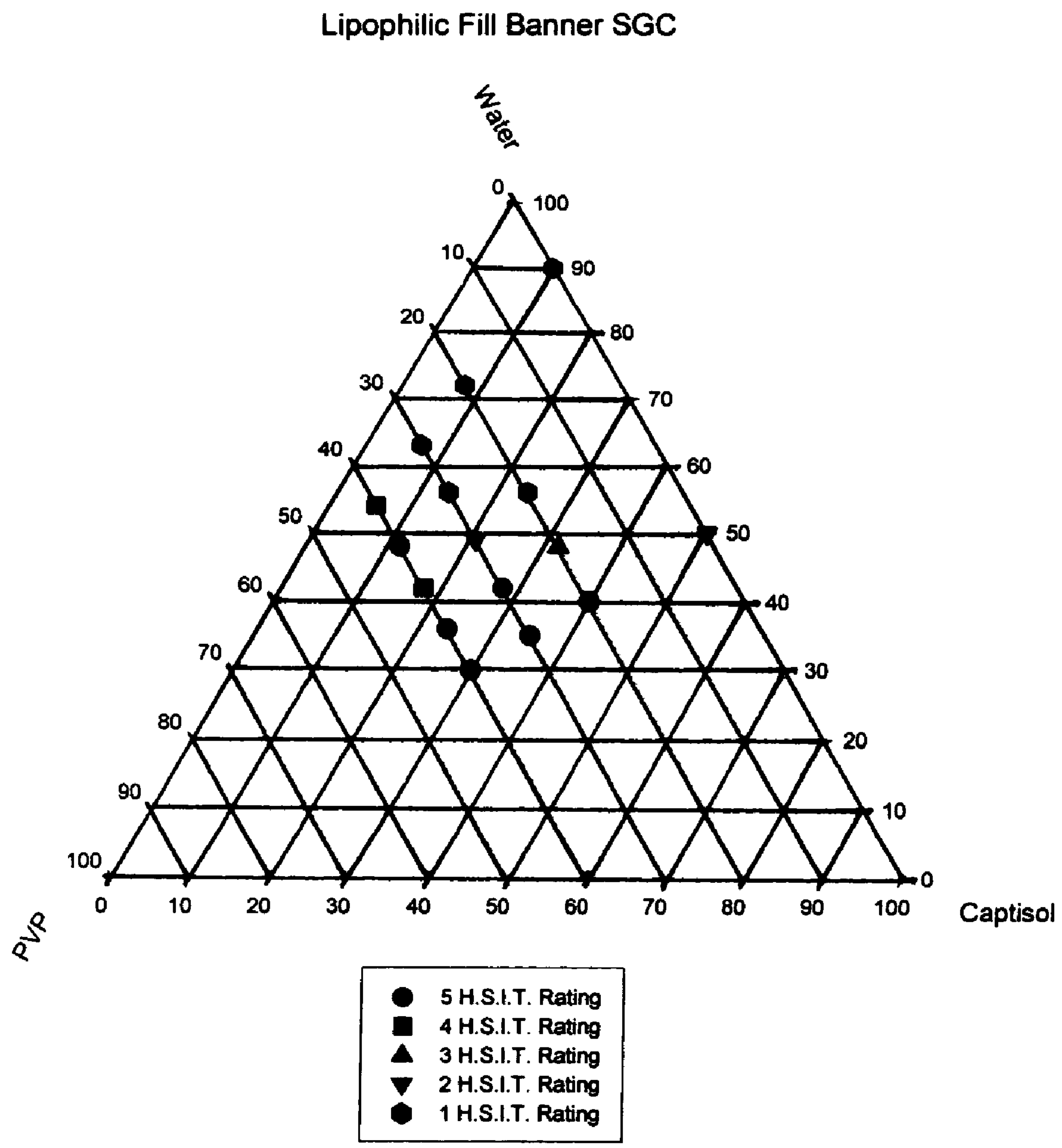

FIGS. 10*a*-10*i* depict ternary graphs correlating the concentration of SAE-CD, water and PVP in a fill composition to the H.S.I.T. rating of a soft shell capsule exposed to the fill composition. Aqueous fill solutions comprising differing amounts of PVP, SAE-CD and water were prepared. The stability tests were conducted as described below. The capsules described herein were used: SHIONOGI HGC (hard gelatin capsule) (FIG. 10A), CAPSUGEL HPMC hard shell capsule (FIG. 10*b*), SHIONOGI HPMC hard shell capsule (FIG. 10C), CAPSUGEL HGC (FIG. 10D), VEGAGEL hard shell capsule (FIG. 10E), hydrophilic fill-grade CARDINAL SGC (soft gelatin capsule) (FIG. 10*f*), lipophilic fill-grade CARDINAL SGC (FIG. 10*g*), hydrophilic fill-grade BANNER SGC (FIG. 10*h*), and lipophilic fill-grade BANNER SGC (FIG. 10*i*). No other shell-stabilizing material(s) was (were) included in the fill compositions evaluated. The results varied according to the capsule used. Stabilized aqueous fill composition-containing capsule formulations can be achieved with each capsule if one or more of the following fill compositions detailed below are used.

1. Water comprises ≧55% of the fill composition, and the combination of SAE-CD, PVP, one or more optional excipients and one or more optional active agents comprises ≧45% of the fill composition; wherein SAE-CD can comprise up to 90% (85%, 83%, or 80%) of the weight of the fill composition, and PVP can comprise less than 90%, respectively, of the weight of the fill composition, provided that the fill composition comprises >≧35% PVP when SAE-CD comprises � LT; ≦15% of the weight of the fill composition, and wherein both PVP (preferably water soluble or water swellable) and SAE-CD are present.
2. Water comprises ≦45% of the fill composition, and the combination of SAE-CD, PVP, one or more optional excipients and one or more optional active agents comprises ≧55% of the fill composition; wherein SAE-CD can comprise up to 90% (85%, 83%, or 80%) of the weight of the fill composition, and PVP can comprise less than 90%, respectively, of the weight of the fill composition, provided that the fill composition comprises ≧35% PVP when SAE-CD comprises ≦20% of the weight of the fill composition, and wherein both PVP (preferably water soluble or water swellable) and SAE-CD are present.
3. Water comprises ≦70% of the fill composition, and the combination of SAE-CD, PVP, one or more optional excipients and one or more optional active agents comprises ≧30% of the fill composition; wherein SAE-CD can comprise up to 90% (85%, 83%, or 80%) of the weight of the fill composition, and PVP can comprise less than 90%, respectively, of the weight of the fill composition, provided that PVP ≧35% when SAE-CD comprises ≦15% of the weight of the fill composition, and when PVP ≦35% then SAE-CD ≧15% when water ≧50%, and wherein both PVP (preferably water soluble or water swellable) and SAE-CD are present.
4. Water comprises ≦65% of the fill composition, and the combination of SAE-CD, PVP, one or more optional excipients and one or more optional active agents comprises ≧35% of the fill composition; wherein SAE-CD can comprise up to 90% (85%, 83%, or 80%) of the weight of the fill composition, and PVP can comprise less than 90%, respectively, of the weight of the fill composition, provided that both PVP (preferably water soluble or water swellable) and SAE-CD are present.
5. Water comprises ≦45% of the fill composition, and the combination of SAE-CD, PVP, one or more optional excipients and one or more optional active agents comprises ≧55% of the fill composition; wherein SAE-CD can comprise up to 90% (85%, 83%, or 80%) of the weight of the fill composition, and PVP can comprise less than 90%, respectively, of the weight of the fill composition, wherein both PVP (preferably water soluble or water swellable) and SAE-CD are present.
6. Water comprises ≦50% of the fill composition, and the combination of SAE-CD, PVP, one or more optional excipients and one or more optional active agents comprises ≧50% of the fill composition; wherein SAE-CD can comprise up to 90% (85%, 83%, or 80%) of the weight of the fill composition, and PVP can comprise less than 90%, respectively, of the weight of the fill composition, provided that the fill composition comprises ≧35% PVP when SAE-CD comprises ≦15% of the weight of the fill composition, and wherein both PVP (preferably water soluble or water swellable) and SAE-CD are present.

The above values for water, SAE-CD, PVP, optional drug (s) and optional excipient(s) add up to 100% wt. of the fill composition. Depending upon the shell being used, fill compositions made according to the above-noted ranges provide an HSIT rating of at least "3" for a capsule containing the aqueous fill composition.

The table below summarizes some of the data observed in FIGS. LOA-LOI for obtaining capsules according to the invention, wherein the capsule has an HSIT rating of at least "3".

| CAPSULE | SAE-CD (%) | PVP + SAE-CD + OTHER (%) | Water (%) |
|---|---|---|---|
| SHIONOGI HGC | ≧6 | ≧46 | ≦54 |
| CAPSUGEL HPMC hard shell capsule | ≧6 | ≧30 | ≦70 |
| SHIONOGI HPMC hard shell capsule | ≧6 | ≧40 | ≦60 |
| CAPSUGEL HGC | ≧24 | ≧64 | ≦36 |
| VEGAGEL hard shell capsule | ≧6 | ≧36 | ≦64 |
| hydrophilic fill-grade CARDINAL SGC | ≧6 | ≧46 | ≦54 |
| lipophilic fill-grade CARDINAL SGC | ≧6 | ≧61 | ≦49 |
| hydrophilic fill-grade BANNER SGC | ≧6 | ≧46 | ≦54 |
| lipophilic fill-grade BANNER SGC | ≧6 | ≧46 | ≦54 |

Under each of the conditions tested, the control sample excluded SAE-CD, i.e., containing only water and PVP at the indicated concentration, and failed within 24 hours (See FIG. 9). Increasing the SAE-CD and/or the PVP concentration to values higher than those indicated above or in the ternary graphs further increases the shelf-life of the shell or provides an HSIT rating of at least 4.

As used herein, the term "water-stabilized capsule shell" refers to a shell that has been rendered stable for at least a predetermined period of time to an aqueous fill composition therein, wherein the stability is expressed in terms of the erosion, degradation, dissolution or swelling of the shell by water in the aqueous fill composition.

A water-stabilized capsule shell has an increased shelf life due to the presence of a derivatized cyclodextrin, and optionally a shell-stabilizing material and/or water activity reducing material, in an aqueous fill composition contained within the shell.

A capsule according to the invention will have a storage shelf life of no less than one week, three weeks, one month, three months, six months, or one year. In this case, shelf life is determined only as regards the stability of the shell toward erosion, dissolution, swelling or degradation of the shell by water in the fill composition. For example, for a capsule having a shelf life of at least six months, the shell of the capsule will not fail storage stability tests due to erosion, dissolution, swelling or degradation of the shell by water from the fill composition for a storage period of at least six months.

The criteria for acceptable shelf-life are set as needed according to a given capsule product and its storage stability requirements. It should be noted that a shelf-life of as little as one week is suitable for products that are compounded by a pharmacist and sold to customers of a pharmacy.

As used herein, a pharmaceutically acceptable liquid carrier is any aqueous or nonaqueous medium used in the pharmaceutical sciences such as water, organic solvent, organic compound, or a combination thereof.

The shell can be hard or soft and any materials suitable for preparing such shells can be used in the capsule of the invention. Materials suitable for the preparation of the capsule shell include soft gelatin, hard gelatin, hydroxypropyl methylcellulose, starch, animal gelatin, agar, fish (piscine) gelatin or a combination thereof. Other suitable materials include: polvinyl alcohol/polyvinyl acetate copolymer (U.S. Pat. No. 3,300,546); a blend of hydroxybutyl methylcellulose and hydroxypropyl methylcellulose (U.S. Pat. No. 4,765,916); polyvinyl acetate (U.S. Pat. No. 2,560,649, No. 3,346,502); water-soluble gelatin (U.S. Pat. No. 3,525,426); polyvinyl alcohol (U.S. Pat. No. 3,528,921, No. 3,534,851, No. 3,556,765, No. 3,634,260, No. 3,671,439, No. 3,706,670, No. 3,857,195, No. 3,877,928, No. 4,367,156, No. 4,747,976, No. 5,270,054); polymers derived from such monomers as vinyl chloride, vinyl alcohol, vinyl pyrrolidone, furan, acrylonitrile, vinyl acetate, methyl acrylate, methyl methacrylate, styrene, vinyl ethyl ether, vinyl propyl ether, acrylamide, ethylene, propylene, acrylic acid, methacrylic acid, maleic anhydride, salts of any of the aforementioned acids and mixtures thereof; polyvinyl chloride; polypropylene; acrylic/maleic copolymers; sodium polyacrylate; polyvinyl pyrrolidone; glucomannan and optionally another natural polysaccharide with a polyhydric alcohol such as glycerin (U.S. Pat. No. 4,851,394); plastic and polylactide/polyglycolide (Elanco Animal Health Co.); HPMC (Shionogi Qualicaps Co. Ltd (Nara Japan); SUHEUNG CAPSULES CO. LTD. (KYUNGGI-DO, KOREA) and Capsugel); or a combination thereof. Essentially any material known to those of ordinary skill in the art as being for the preparation of capsule shell can be used in a capsule according to the invention. Suitable starch capsules can be made and used according to Vilivalam et al. (*Pharmaceutical Science & Technology Today* (2000), 3 (2), 64-69). A chitosan capsule for colonic delivery can be made and used according to Yamamoto (*Kobunshi* (1999), 48 (8), 595) or Tozaki et al. (*Drug Delivery System* (1997), 12 (5), 311-320).

Capsules from the following suppliers were evaluated herein:

Banner Pharmacaps hydrophilic and lipophilic fill, soft gelatin capsules (SGC).

Cardinal Health hydrophilic and lipophilic fill SGC.

Swiss Caps VegaGel flaxseed oil filled, potato starch soft capsules

SHIONOGI Qualicaps Posilok hard gelatin capsules (HGC) and QualiV (HPMC) capsules.

Capsugel HGC and Vcap (HPMC) capsules.

The term "shell" as used herein is taken to mean the shell of a capsule dosage form or the encasement or encapsulation material used to encapsulate fill compositions. Any material suitable for use in forming a capsule shell or in encapsulating another composition can be used according to the invention. An aqueous composition according to the invention is surrounded by a water erodible, soluble, swellable and/or degradable shell or encapsulating material.

Other suitable shell materials are disclosed in U.S. patent application Publication No. 2002/0081331 to R. P. Scherer Technologies Inc. (Cardinal Health, Inc.), which discloses film-forming compositions comprising modified starches and iota-carrageenan.

The formulation of the invention can comprise a sulfoalkyl ether cyclodextrin of the formula I:

Formula 1

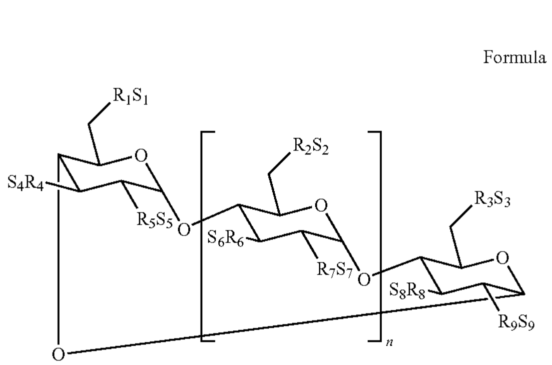

wherein:

is 4, 5 or 6;

$R_1$, $R_2$, $R_3$, $R_4$, $R_5$, $R_6$, $R_7$, $R_8$ and $R_9$ are each, independently, —O— or a —O—($C_2$-$C_6$ alkylene)-$SO_3^-$ group, wherein at least one of $R_1$, $R_2$, $R_3$, $R_4$, $R_5$, $R_6$, $R_7$, $R_8$ and $R_9$ is independently a —O —($C_2$-$C_6$ alkylene)-$SO_3^-$ group, preferably a —O—$(CH_2)_m SO_3^-$ group, wherein m is 2 to 6, preferably 2 to 4, (e.g. —$OCH_2CH_2CH_2SO_3^-$or-$OCH_2CH_2CH_2CH_2SO_3^-$); and $S_1$, $S_2$, $S_3$, $S_4$, $S_5$, $S_6$, $S_7$, $S_8$ and $S_9$ are each, independently, a cation which includes, for example, $H^+$, alkali metals (e.g. $Li^+$, $Na^+$, $K^+$), alkaline earth metals (e.g., $Ca^{+2}$, $Mg^{+2}$), ammonium ions and amine cations such as the cations of ($C_1$-$C_6$)-alkylamines, piperidine, pyrazine, ($C_1$-$C_6$)-alkanolamine and ($C_4$-$C_8$)-cycloalkanolamine.

Since SAE-CD is a poly-anionic cyclodextrin, it can be provided in different salt forms. Suitable counterions include cationic organic atoms or molecules and cationic inorganic atoms or molecules. The SAE-CD can include a single type of counterion or a mixture of different counterions. The properties of the SAE-CD can be modified by changing the identity of the counterion present. For example, a first salt form of SAE-CD can have a greater water activity reducing power than a different second salt form of SAE-CD. Likewise, an SAE-CD having a first degree of substitution can have a greater water activity reducing power than a second SAE-CD having a different degree of substitution.

The SAE-CD used in the formulation is described in U.S. Pat. No. 5,376,645 and No. 5,134,127 to Stella et al, the entire disclosures of which are hereby incorporated by reference. The preparation process may comprise dissolving the cyclodextrin in aqueous base at an appropriate temperature, e.g., 70° to 80° C., at the highest concentration possible. For example, to prepare the cyclodextrin derivatives herein, an amount of an appropriate alkyl sultone, corresponding to the number of moles of primary CD hydroxyl group present, is added with vigorous stirring to ensure maximal contact of the heterogeneous phase. According to one embodiment, the SAE-CD is SBE-7-β-CD (CAPTISOL® cyclodextrin), or SBE-4-β-CD (ADAVASEP®). An SAE-CD made according to other known procedures should also be suitable for use in the invention as long as the SAE-CD has the ability to reduce water activity.

The terms "alkylene" and "alkyl", as used herein (e.g., in the -0-(C2-C6-alkylene) S03$^-$ group or in the alkylamines), include linear, cyclic, and branched, saturated and unsaturated (i.e., containing one double bond) divalent alkylene groups and monovalent alkyl groups, respectively. The term "alkanol" in this text likewise includes both linear, cyclic and branched, saturated and unsaturated alkyl components of the alkanol groups, in which the hydroxyl groups may be situated at any position on the alkyl moiety. The term "cycloalkanol" includes unsubstituted or substituted (e.g., by methyl or ethyl) cyclic alcohols.

The present invention provides compositions containing a mixture of cyclodextrin derivatives wherein two or more different types of cyclodextrin derivatives are included in the fill composition. By different types, is meant cyclodextrins derivatized with different types of functional groups e.g., hydroxyalkyl and sulfoalkyl, and not to the heterogeneous nature of derivatized cyclodextrins due to their varying degrees of substitution. The amount of each type of cyclodextrin derivative present can be varied as desired to provide a mixture having the desired properties.

The present invention also provides compositions containing a single type of cyclodextrin derivative, or at least 50% of a single type of cyclodextrin derivative. The invention also includes compositions containing cyclodextrin derivatives having a narrow or wide and high or low degree of substitution. These combinations can be optimized as needed to provide cyclodextrins having particular properties.

The cyclodextrin derivatives of the present invention are obtained as purified compositions, i.e., compositions containing at least 50% wt. of cyclodextrin derivative(s). In other words, a derivatized cyclodextrin can include a minor (less than 50% wt.) amount of underivatized cyclodextrin. In a preferred embodiment, purified compositions containing at least 90 wt. % cyclodextrin derivative (s) are obtained.

In some of the compositions of the invention unreacted/underivatized cyclodextrin has been substantially removed, with the remaining impurities being inconsequential to the performance of the cyclodextrin derivative-containing composition.

Exemplary SAE-CD derivatives include SBE4-β-CD, SBE7-β-CD, SBELL-β-CD, and SBE4-γ-CD which correspond to SAE-CD derivatives of the formula I wherein n=5, 5, 5 and 6; M is 4; and there are 4, 7, 11 and 4 sulfoalkyl ether substituents present, respectively. It has been found that these SAE-CD derivatives increase the solubility of poorly water soluble active agents to varying degrees.

By "complexed" is meant "being part of a clathrate or inclusion complex with", i.e., a complexed active agent is part of a clathrate or inclusion complex with a cyclodextrin derivative.

By active agent/CD complex is generally meant a clathrate or inclusion complex of a cyclodextrin derivative and an active agent. The ratio of active agent: CD present in the molecular complex can vary and can be in the range of about 10 to about 0.1, on a molar basis. Thus, the CD will generally be, but need not be, present in excess of the active agent. The amount of excess will be determined by the intrinsic solubility of the agent, the expected dose of the agent, and the binding constant for inclusion complexation between the specific drug (agent) and the specific CD derivative used. It should be noted that the cyclodextrin derivative can be present in uncomplexed form and therefore in amounts substantially in excess of the amount of active agent present. The weight ratio or molar ratio of derivatized cyclodextrin to active agent can exceed 100, 1000 or even more.

Under conditions wherein an ionized cyclodextrin derivative can form one or more ionic bonds with a positively charged acid-ionizable compound, the derivatized cyclodextrin can be present in low concentrations and the ratio of compound to derivatized cyclodextrin can be greater than one. Therefore, it is possible for the compound to be complexed by way of an inclusion complex with the derivatized cyclodextrin and to be non-covalently ionically bound to the derivatized cyclodextrin.

These derivatized cyclodextrins differ in their degree of substitution by functional groups, the number of carbons in the functional groups, their molecular weight, the number of glucopyranose units contained in the base cyclodextrin used to form the derivatized cyclodextrin and or their substitution patterns. In addition, the derivatization of (3-cyclodextrin with functional groups occurs in a controlled, although not exact manner. For this reason, the degree of substitution is actually a number representing the average number of functional groups per cyclodextrin (for example, SBE7-β-CD, has an average of 7 substitutions per cyclodextrin). In addition, the regiochemistry of substitution of the hydroxyl groups of the cyclodextrin is variable with regard to the substitution of specific hydroxyl groups of the hexose ring. For this reason, substitution of the different hydroxyl groups is likely to occur during manufacture of the derivatized cyclodextrin, and a particular derivatized cyclodextrin will possess a preferential, although not exclusive or specific, substitution pattern. Given the above, the molecular weight of a particular derivatized cyclodextrin may vary from batch to batch and will vary from derivatized cyclodextrin. All of these variations can lead to changes in the complexation equilibrium constant $K_{1:1}$ which in turn will affect the required molar ratios of the derivatized cyclodextrin to active agent. The equilibrium constant is also somewhat variable with temperature and allowances in the ratio are required such that the agent remains solubilized during the temperature fluctuations that can occur during manufacture, storage, transport, and use. The equilibrium constant is also variable with pH and allowances in the ratio are required such that the agent remains solubilized during pH fluctuations that can occur during manufacture, storage, transport, and use. The equilibrium constant is also variable by the presence of other excipients (e.g., buffers, preservatives, antioxidants) Accordingly, the ratio of derivatized cyclodextrin to active agent may need to be varied from the ratios set forth herein in order to compensate for the above-mentioned variables.

The HPCD can be obtained from Research Diagnostics Inc. (Flanders, N.J.). HPCD is available with different degrees of substitution. Exemplary products include ENCAPSIN™ (degree of substitution-4; HP4-P-CD) and MOLECUSOL™ (degree of substitution ~8 ; HP8-β-CD), however, embodiments including other degrees of substitution are also available. Since HPCD is non-ionic, it is not available in salt form. As with other derivatized cyclodextrins of the invention, changes in the degree of substitution can result in changes in the ability of the HPCD to stabilize the shell. One grade of HPCD used was C*CAVITRON 82005 (Cerestar USA, Inc. Hammond, Ind.). It has an average degree of substitution of 5.5.

Dimethyl cyclodextrin is available from FLUKA Chemie (Buchs, CH) or Wacker (IOWA). Other derivatized cyclodextrins suitable in the invention include water soluble derivatized cyclodextrins. Exemplary water-soluble derivatized cyclodextrins include carboxylated derivatives; sulfated derivatives; alkylated derivatives; hydroxyalkylated derivatives; methylated derivatives; and carboxy-β-cyclodextrins, e.g. succinyl-β-cyclodextrin, $6^A$-amino-$6^A$-deoxy-N-(3-carboxypropyl)-β-cyclodextrin. All of these materials can be made according to methods known in the prior art. Suitable derivatized cyclodextrins are disclosed in Modified Cyclodextrins: Scaffolds and Templates for Supramolecular Chemistry (Eds. Christopher J. Easton, Stephen F. Lincoln, Imperial College Press, London, UK, 1999) and New Trends in Cyclodextrins and Derivatives (Ed. Dominique Duchene, Editions de Santé, Paris, France, 1991).

Although not necessary, the formulation of the present invention may include a preservative, antioxidant, buffering agent, acidifying agent, alkalizing agent, antibacterial agent, antifungal agent, colorant, solubility-enhancing agent, complexation enhancing agent, solvent, electrolyte, salt, water, glucose, stabilizer, tonicity modifier, antifoaming agent, oil, plasticizer, flavors, sweeteners, other excipients known by those of ordinary skill in the art for use in aqueous fill capsules, or a combination thereof.

A complexation-enhancing agent can be added to the aqueous liquid formulation of the invention. A complexation-enhancing agent is a compound, or compounds, that enhance(s) the complexation of an active agent with the derivatized cyclodextrin. When the complexation-enhancing agent is present, the required ratio of derivatized cyclodextrin to active agent may need to be changed such that less derivatized cyclodextrin is required. Suitable complexation enhancing agents include one or more pharmacologically inert water soluble polymers, hydroxy acids, and other organic compounds typically used in liquid formulations to enhance the complexation of a particular agent with cyclodextrins. Suitable water soluble polymers include water soluble natural polymers, water soluble semisynthetic polymers (such as the water soluble derivatives of cellulose) and water soluble synthetic polymers. The natural polymers include polysaccharides such as inulin, pectins, algin derivatives and agar, and polypeptides such as casein and gelatin. The semi-synthetic polymers include cellulose derivatives such as methylcellulose, hydroxyethyl cellulose, hydroxypropyl cellulose, their mixed ethers such as hydroxypropyl methylcellulose and other mixed ethers such as hydroxyethyl ethylcellulose, hydroxypropyl ethylcellulose, hydroxypropyl methylcellulose phthalate and carboxymethylcellulose and its salts, especially sodium carboxymethylcellulose. The synthetic polymers include polyoxyethylene derivatives (polyethylene glycols) and polyvinyl derivatives (polyvinyl alcohol, poly (vinyl pyrrolidone) and polystyrene sulfonate) and various copolymers of acrylic acid (e. g. CARBOMER™). Suitable hydroxy acids include by way of example, and without limitation, citric acid, malic acid, lactic acid, and tartaric acid and others known to those of ordinary skill in the art.

A solubility-enhancing agent can be added to the aqueous liquid formulation of the invention. A solubility-enhancing agent is a compound, or compounds, that enhance(s) the solubility of active agent in the liquid composition. When a solubility-enhancing agent is present, the ratio of derivatized cyclodextrin to active agent may need to be changed such that less derivatized cyclodextrin is required. Suitable solubility enhancing agents include one or more organic solvents, detergents, soaps, surfactants and other organic compounds typically used in parenteral formulations to enhance the solubility of a particular agent. Suitable organic solvents include, for example, ethanol, glycerin, poly (ethylene glycols), propylene glycol, poly (propylene glycols), poloxamers, and others known to those of ordinary skill in the art.

As used herein, the term "alkalizing agent" is intended to mean a compound used to provide alkaline medium for product stability. Such compounds include, by way of example and without limitation, ammonia solution, ammonium carbonate, diethanolamine, monoethanolamine, potassium hydroxide, sodium borate, sodium carbonate, sodium bicarbonate, sodium hydroxide, triethanolamine, organic amine base, alkaline amino acids and trolamine and others known to those of ordinary skill in the art.

As used herein, the term "acidifying agent" is intended to mean a compound used to provide an acidic medium for product stability. Such compounds include, by way of example and without limitation, acetic acid, acidic amino acids, citric acid, fumaric acid and other alpha hydroxy acids, hydrochloric acid, ascorbic acid, phosphoric acid, sulfuric acid, tartaric acid and nitric acid and others known to those of ordinary skill in the art.

As used herein, the term "preservative" is intended to mean a compound used to prevent the growth of microorganisms. Such compounds include, by way of example and without limitation, benzalkonium chloride, benzethonium chloride, benzoic acid, benzyl alcohol, cetylpyridinium chloride, chlorobutanol, phenol, phenylethyl alcohol, phenylmercuric nitrate, phenylmercuric acetate, thimerosal, metacresol, myristylgamma picolinium chloride, potassium benzoate, potassium sorbate, sodium benzoate, sodium propionate, sorbic acid, thymol, and methyl, ethyl, propyl, or butyl parabens and others known to those of ordinary skill in the art.

As used herein, the term "antioxidant" is intended to mean an agent that inhibits oxidation and thus is used to prevent the deterioration of preparations by the oxidative process. Such compounds include by way of example and without limitation, acetone, sodium bisulfate, ascorbic acid, ascorbyl palmitate, citric acid, butylated hydroxyanisole, butylated hydroxytoluene, hydrophosphorous acid, monothioglycerol, propyl gallate, sodium ascorbate, sodium citrate, sodium sulfide, sodium sulfite, sodium bisulfite, sodium formaldehyde sulfoxylate, thioglycolic acid, sodium metabisulfite, EDTA (edetate), pentetate and others known to those of ordinary skill in the art.

As used herein, the term "buffering agent" is intended to mean a compound used to resist change in pH upon dilution or addition of acid or alkali. Such compounds include, by way of example and without limitation, acetic acid, sodium acetate, adipic acid, benzoic acid, sodium benzoate, citric acid, maleic acid, monobasic sodium phosphate, dibasic sodium phosphate, lactic acid, tartaric acid, glycine, potassium metaphosphate, potassium phosphate, monobasic sodium acetate, sodium bicarbonate, sodium tartrate and sodium citrate anhydrous and dihydrate and others known to those of ordinary skill in the art.

As used herein, the term "stabilizer" is intended to mean a compound used to stabilize a active agent against physical, chemical, or biochemical process that would otherwise reduce the therapeutic activity of the agent. Suitable stabilizers include, by way of example and without limitation, albumin, sialic acid, creatinine, glycine and other amino acids, niacinamide, sodium acetyltryptophonate, zinc oxide, sucrose, glucose, lactose, sorbitol, mannitol, glycerol, polyethylene glycols, sodium caprylate and sodium saccharin and others known to those of ordinary skill in the art.

As used herein, the term "colorant" is intended to mean a compound used to impart color to pharmaceutical preparations. Such compounds include, by way of example and without limitation, FD&C Red No. 3, FD&C Red No. 20, FD&C Yellow No. 6, FD&C Blue No. 2, D&C Green No. 5, D&C Orange No. 5, D&C Red No. 8, caramel, and iron oxide (black, red, yellow), other F. D. & C. dyes and natural coloring agents such as grape skin extract, beet red powder, betacarotene, annato, carmine, turmeric, paprika, combinations thereof and other such materials known to those of ordinary skill in the art.

The capsule of the invention can also include oils such as fixed oils, fish oil, peanut oil, sesame oil, cottonseed oil, corn oil and olive oil; fatty acids such as oleic acid, stearic acid and isostearic acid; and fatty acid esters such as ethyl oleate, isopropyl myristate, fatty acid glycerides and acetylated fatty acid glycerides. The capsule can also include alcohol such as ethanol, isopropanol, hexadecyl alcohol, glycerol and propylene glycol; glycerol ketals such as 2,2-dimethyl-1,3-dioxolane-4-methanol; ethers such as poly (ethyleneglycol) 450; petroleum hydrocarbons such as mineral oil and petrolatum; water; mixtures thereof; or a pharmaceutically suitable surfactant, suspending agent or emulsifying agent.

Soaps and synthetic detergents may be employed as surfactants and as vehicles for detergent compositions. Suitable soaps include fatty acid alkali metal, ammonium, and triethanolamine salts. Suitable detergents include cationic detergents such as dimethyl dialkyl ammonium halides, alkyl pyridinium halides, and alkylamine acetates; anionic detergents such as alkyl, aryl and olefin sulfonates, alkyl, olefin, ether and monoglyceride sulfates, and sulfosuccinates; non-ionic detergents such as fatty amine oxides, fatty acid alkanolamides, and poly(oxyethylene)-block-poly(oxypropylene) copolymers; amphoteric detergents such as alkyl β-aminopropionates and 2-alkylimidazoline quaternary ammonium salts; and mixtures thereof.

As used herein, the term "tonicity modifier" is intended to mean a compound or compounds that can be used to adjust the tonicity of the liquid formulation. Suitable tonicity modifiers include glycerin, lactose, mannitol, dextrose, sodium chloride, sodium sulfate, sorbitol, trehalose and others known to those or ordinary skill in the art.

As used herein, the term "antifoaming agent" is intended to mean a compound or compounds that prevents or reduces the amount of foaming that forms on the surface of the fill composition. Suitable antifoaming agents include by way of example and without limitation, dimethicone, SIMETHICONE, octoxynol and others known to those of ordinary skill in the art.

It should be understood, that compounds used in the pharmaceutical arts generally serve a variety of functions or purposes. Thus, if a compound named herein is mentioned only once or is used to define more than one term herein, its purpose or function should not be construed as being limited solely to that named purpose (s) or function (s).

The chemical stability of the fill composition of the invention, in terms of forming a precipitate or gel, may be enhanced by adjusting the pH of the liquid carrier.

The pH of the fill composition will generally range from about pH 1 to about pH 11; however, fill compositions having pH values that are neutral, basic or acidic can also be prepared. An acidic fill composition would be suitable for a capsule which shell is stable to acid in the fill composition. Likewise, a basic fill composition would be suitable for a capsule which shell is stable to alkaline materials in the fill composition.

The release profile of active agent from the capsule can be any release profile known for capsule/encapsulated formulations. For example after oral administration, the release of active agent can be gastric (release in the stomach), delayed (release in the gastrointestinal tract downstream of the stomach), enteric (release in the small intestine) or colonic (release in the colon). Release of active agent from the capsule can be rapid or sustained (extended or controlled) release. A sustained release capsule can be made according to Miyao (*Pharm. Tech. Jpn*. (1988), 4 (2), 141-3) and modified according to the invention to include an aqueous fill composition. A controlled release capsule can be made according to Okahata (*Sen'I Gakkaishi* (1987), 43 (12), 482-488) and modified according to the invention to include an aqueous fill composition. Hard gelatin capsules can be made according to Berezovskaya et al. (*Khim.-Farm. Zh*. (1978), 12 (10), 87-97) and modified according to the invention to include an aqueous fill composition. Microencapsulated dosage forms can be made according to Luzzi (*Drugs Pharm. Sci.* (1976), 3 (microencapsulation), 193-206) and modified according to the invention to include an aqueous fill composition.

The TARGIT™ colonic delivery (West Pharmaceutical Services (Nottingham, UK; U.S. Pat. No. 6,228,396) capsule technology can be used to make capsules according to the invention by injection molding of starch capsules and then coating of the capsules with a mixture of plasticized enteric polymers such as EUDRAGIT™ L and EUDRAGIT™ S. By changing the thickness of the coating, drug delivery to the terminal ileum, ascending colon, transverse colon or descending colon can be achieved.

BANNER PHARMACAPS (Highpoint, N.C.) manufactures a line of soft gelatin capsules under the trademark GELATIN BINARY SYSTEM®;, which capsules are adapted for enteric delivery of drugs. Those uncoated capsules achieve enteric delivery of drug due to the enteric release properties incorporated within the gelatin material itself. Such capsules can be used to deliver a fill composition according to the invention.

Enteric and colonic release capsules according to the invention provide a substantial advantage over solid non-aqueous enteric and colonic release dosage forms. In particular for colonic delivery, the water included within the present capsules serves to aid in distribution of the fill composition in the colon and avoids the step of dissolving the fill composition in the intestine prior to delivery as must be done with non-aqueous colonic delivery dosage forms. The capsules also have increased osmotic pressure in the colon and small intestines, as compared to those other dosage forms. As a result, the present capsules can employ the increased osmotic pressure to enhance drug release.

The invention also includes an embodiment comprising a capsule within a capsule. The inner and/or outer capsule can contain an aqueous fill composition according to the invention or another composition. Such a system can be made according to Bakhshaee et al. (PCT International Publication No. WO 02/07710 A2 (Jan. 31, 2002) and modified according to the present invention by including the present aqueous fill composition.

The loading or filling of a liquid composition into a capsule can be achieved by any known method for preparing liquid, gel, semi-solid or solid melt filled capsules. In particular, the methods described by R. P. Scherer company, Alza or MW Encap Ltd. can be used. One exemplary method is described by Bowtle (*Pharmaceutical Technology Europe* (1998), 10 (10), 84,86, 88-90.

A liquid filled capsule having a biphasic release profile can be made according to Bowtle (*International Journal of Pharmaceutics* (1996) 141 (1-2), 9-16) and modified as described herein to include an aqueous fill composition as described herein.

A multi-layered capsule can be made according to Ishibashi et al. (*Int. J Pharm.* (1998), 168,31-40) and modified as described herein to include an aqueous fill composition as described herein. The multi-layered capsule would have an inner capsule coated with a layer of cationic polymer, then a layer of water soluble or erodible material and finally an outer layer containing a material that dissolves at a pH of about 5 or higher. This capsule would provide delayed release (release after the stomach) for a predetermined lag time such that the content of the fill composition would be release abruptly upon rupture, erosion or dissolution of the innermost shell.

Polyvinyl acetate phthalate (PVAP) can be used as a coating material for capsules. This material is suitable for enteric release of an active agent included in the capsule. When a capsule coated with PVAP is administered orally to a subject, the active agent is released in the GI tract downstream from the stomach.

Since the fill composition does not require PEG or other similar materials known to affect crosslinking of a soft gelatin shell, a capsule dosage form is generally free of the crosslinking the occurs during storage.

The fill composition of the invention can be prepared by numerous different methods. According to one method, a first aqueous solution comprising derivatized cyclodextrin and optionally one or more excipients is prepared. Then, a second solution comprising an active agent and optionally one or more excipients is prepared. Finally, the first and second solutions are mixed to form the fill composition. The first and second solutions can independently comprise other excipients and agents described herein. Additionally, the second solution can be water and/or an organic solvent-based solution.

Another method of preparation is similar to the above-described method except that the active agent is added directly to the first solution without the formation of a second solution.

A third method of preparing the fill composition is similar to the above-described first method except that the derivatized cyclodextrin is added directly to an aqueous second solution containing the active agent without formation of the first solution.

A fourth method of preparing the fill composition comprises the steps of adding an aqueous solution comprising an active agent to a powdered or particulate derivatized cyclodextrin and mixing the solution until the derivatized cyclodextrin has dissolved.

A fifth method of preparing the fill composition comprises the steps of adding the active agent directly to the powdered or particulate derivatized cyclodextrin and then adding an aqueous solution and mixing until the derivatized cyclodextrin and active agent have dissolved.

A sixth method for preparing the fill composition comprises the steps of heating either the first solution or heating the second solution, or heating a combination thereof of any solutions described in the above methods followed by the step of cooling the respectively heated solution.

Another method for preparing the fill composition comprises the step concentrating a solution of derivatized cyclodextrin. The step of concentrating can be by accomplished by evaporation, drum drying, tray drying or other conventional methods of reducing the amount of water in a composition.

Any of the above solutions can contain other pharmaceutical excipients or ingredients as described herein.

Specific embodiments of the method of preparing the fill composition include those wherein the method further comprises the step of 1) sterile filtering the fill composition through a filtration medium wherein the pore size is about 0.22 μm or smaller; 2) sterilizing the fill composition by irradiation; 3) sterilizing the fill composition by treatment with ethylene oxide; 4) purging the fill composition with an inert gas to reduce the amount of dissolved oxygen therein; and/or 5) heating one or more of the solutions used to prepare the fill composition.

A unit dosage form is a single or multiple dose form containing a quantity of the active ingredient and the diluent or carrier, said quantity being such that one or more predetermined units are normally required for a single therapeutic administration. In the case of multiple dose forms, such as capsules, said predetermined unit will be one fraction such as a half or quarter of the multiple dose form. It will be understood that the specific dose level for any patient will depend upon a variety of factors including the indication being treated, active agent employed, the activity of active agent, severity of the indication, patient health, age, sex, weight, diet, and pharmacological response, the specific dosage form employed and other such factors.

The phrase “pharmaceutically acceptable” is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term “patient” or “subject” is taken to mean warm blooded animals such as mammals, for example, cats, dogs, mice, guinea pigs, horses, bovine cows, sheep, and humans.

The fill composition can include one or more of any known active agents. The active agent included in the present invention can possess a wide range of values for water solubility, bioavailability and hydrophilicity. Active agents to which the present invention is particularly suitable include water insoluble, poorly water soluble, slightly water soluble, moderately water soluble, water soluble, very water soluble, hydrophobic, or hydrophilic therapeutic agents. It will be understood by the artisan of ordinary skill that an active agent used in the fill composition of the present invention is independently selected at each occurrence from any known active agent and from those disclosed herein. It is not necessary that the active agent complex with the derivatized cyclodextrin.

Active agents generally include physiologically or pharmacologically active substances that produce a systemic or localized effect or effects on animals and human beings. Active agents also include pesticides, herbicides, insecticides, antioxidants, plant growth instigators, sterilization agents, catalysts, chemical reagents, food products, nutrients, cosmetics, vitamins, sterility inhibitors, fertility instigators, microorganisms, flavoring agents, sweeteners, cleansing agents and other such compounds for pharmaceutical, veterinary, horticultural, household, food, culinary, agricultural, cosmetic, industrial, cleaning, confectionery and flavoring applications. The active agent can be present in its neutral, ionic, salt, basic, acidic, natural, synthetic, diastereomeric, isomeric, enantiomerically pure, racemic, hydrate, chelate, derivative, analog, or other common form.

The capsule of the invention can be used to deliver two or more different active agents. Particular combinations of active agents can be provided by the present capsule. Some combinations of active agents include: 1) a first drug from a first therapeutic class and a different second drug from the same therapeutic class; 2) a first drug from a first therapeutic class and a different second drug from a different therapeutic class; 3) a first drug having a first type of biological activity and a different second drug having about the same biological activity; 4) a first drug having a first type of biological activity and a different second drug having a different second type of biological activity. Exemplary combinations of active agents are described herein.

Figure 11:
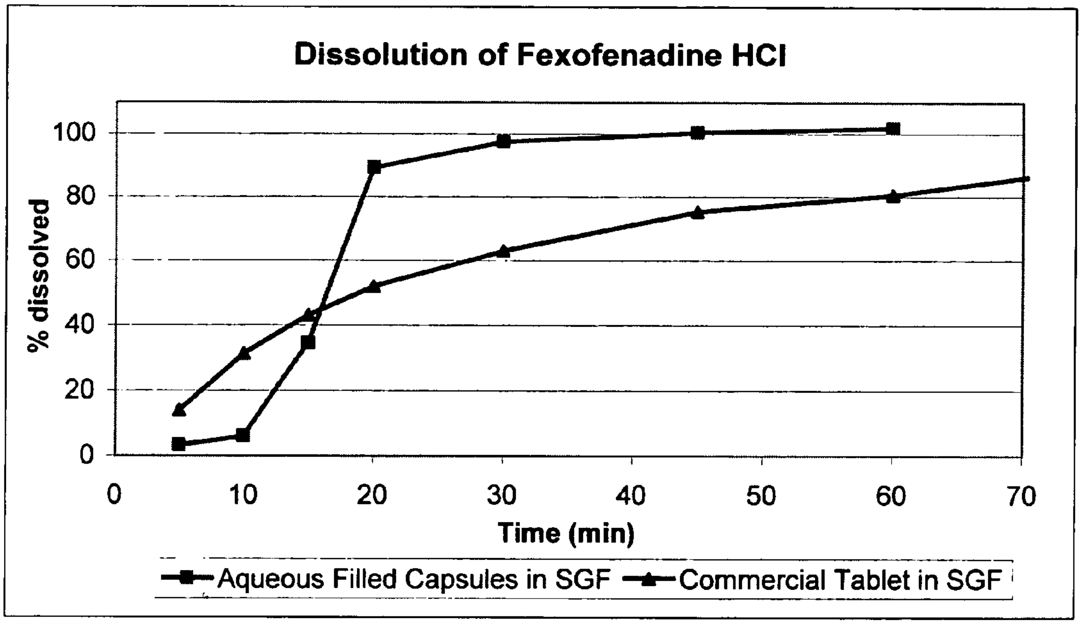
FIG. 11 depicts dissolution profiles for a commercial tablet containing fexofenadine hydrochloride (FEX) and a capsule according to the invention containing SAE-CD, FEX and water.

FIG. 11 shows the dissolution profiles obtained according to Example 6. The percent fexofenadine hydrochloride dissolved as a function of time in USP Simulated Gastric Fluid TS as dissolution media is depicted for a commercial immediate release tablet (ALLEGRAÆ 60 mg. From Aventis Pharmaceuticals, Inc., Kansas City, Mo. 64137 USA) and a capsule according to the invention. Because the capsules used were made from gelatin, the enzymes in the USP test solutions were not excluded from the dissolution medium. Initially, the tablet provides a more immediate release of drug; however, the capsule quickly surpasses the tablet in terms of the rate of drug release and the total amount of drug released within a one-hour period. After a short initial lag time, the aqueous filled capsule dissolved much more rapidly in the dissolution apparatus. The results indicate that a capsule of the invention may improve the rate and extent of absorption of the drug and be especially useful for drugs where a rapid on set of activity is desired.

The effect of dissolution medium upon the release of drug from the capsule versus the commercial tablet was evaluated. The table below shows the results.

| Sample | Media | Time for 80% to dissolve |
|---|---|---|
| Capsule | USP Simulated Gastric Fluid, TS (Test Solution) | 19 minutes |
| Tablet | USP Simulated Gastric Fluid, TS (without enzymes) | 41 minutes |
| Capsule | USP Simulated Intestinal Fluid, TS | 27 minutes |
| Tablet | USP Simulated Intestinal Fluid, TS (without enzymes) | 9 minutes |
| Capsule | Water | 26 minutes |
| Tablet | Water | 8 minutes |

The aqueous filled capsules dissolved rapidly, (less than 30 minutes for 80% of the drug to dissolve), regardless of the media used. It was fastest in simulated gastric fluid. Dissolution of the commercial tablet was slowest in simulated gastric fluid. As this media is most like the environment first encountered by an oral dosage form, aqueous filled compositions stabilized with derivatized cyclodextrins could be expected to be especially useful for active ingredients that dissolve slowly in simulated gastric fluid. The invention provides an improved method of orally delivering a drug to the gastric region of a subject, the improvement comprising administering the drug in a gastric fluid soluble, erodible and/or degradable capsule comprising an aqueous fill composition comprising SAE-CD, the drug, water, and one or more optional excipients, wherein the SAE-CD is present in amount sufficient to stabilize the capsule against dissolution, erosion, swelling or degradation caused by water in the fill composition but not against dissolution, erosion, swelling or degradation caused by gastric fluid.

Whenever mentioned and unless otherwise specified, the term “active agent” includes all forms of the active agent including optically pure, racemic, free base, free acid, salt, diastereomeric, regioisomeric, amorphous, hydrate, anhydrous and/or crystalline forms.

The active agent can be independently selected at each occurrence from active agents such as an antibiotic agent, antihistamine agent, decongestant, anti-inflammatory agent, antiparasitic agent, antiviral agent, local anesthetic, antifungal agent, amoebicidal agent, trichomonocidal agent, analgesic agent, anti-arthritic agent, anti-asthmatic agent, anticoagulant agent, anticonvulsant agent, antidepressant agent, antidiabetic agent, antineoplastic agent, anti-psychotic agent, neuroleptic agent, antihypertensive agent, hypnotic agent, sedative agent, anxiolytic energizer agent, antiparkinson agent, muscle relaxant agent, antimalarial agent, hormonal agent, contraceptive agent, sympathomimetic agent, hypoglycemic agent, antilipemic agent, ophthalmic agent, electrolytic agent, diagnostic agent, prokinetic agent, gastric acid secretion inhibitor agent, anti-ulcerant agent, anti-flatulent agent, anti-incontinence agent, cardiovascular agent or a combination thereof.

Protease inhibitors which can be included in the present formulations include, by way of example and without limitation, antipain, leupeptin, chymostatin, amistatin, puromycin and others known to those of ordinary skill in the art.

Penetration enhancers which can be included in the present formulations include, by way of example and without limitation, calcium chelators such as EDTA, methylated P-cyclodextrin, and polycarboxylic acids; surfactants such as sodium lauryl sulfate, sodium dodecyl sulfate, carnitine, carnitine esters, and tween; bile salts such as sodium taurocholate; fatty acids such as oleic and linoleic acid; and non-surfactants such as AZONE™ and dialkyl sulfoxides; E-flux inhibitors such as AV171 (AyMax, Inc., South San Francisco, Calif.), D-α-tocopheryl polyethylene glycol 1000 succinate (TPGS), and peppermint oil; chitosan and chitosan derivatives such as N-methyl chitosan, N-trimethyl chitosan, mono-N-carboxymethyl chitosan, quaternized chitosan derivatives; SNAC (N-(8-[2-hydroxybenzoyl]amino) caprylate) and SNAD (N-[10-(2-hydroxybenzoyl)amino]-decanoate) (Emisphere Technologies, Inc., Tarrytown, N.Y.); N-acylated non-alpha amino acids; HEMISPHERE brand delivery agents; Gélucire 44/14 or Vitamin E TPGS; CARBOPOL® 934P; others known to those of ordinary skill in the art; and combinations thereof.

Drugs suitable for use in the compositions described herein include the following categories and examples of drugs and alternative forms of these drugs such as alternative salt forms, free acid forms, free base forms, and hydrates:

analgesics/antipyretics (e.g., aspirin, acetaminophen, ibuprofen, naproxen sodium, buprenorphine, propoxyphene hydrochloride, propoxyphene napsylate, meperidine hydrochloride, hydromorphone hydrochloride, morphine, oxycodone, codeine, dihydrocodeine bitartrate, pentazocine, hydrocodone bitartrate, levorphanol, diflunisal, trolamine salicylate, nalbuphine hydrochloride, mefenamic acid, butorphanol, choline salicylate, butalbital, phenyltoloxamine citrate, diphenhydramine citrate, methotrimeprazine, cinnamedrine hydrochloride, and meprobamate);

antiasthmatics (e.g., ketotifen and traxanox);

antibiotics (e.g., neomycin, streptomycin, chloramphenicol, cephalosporin, ampicillin, penicillin, tetracycline, and ciprofloxacin);

antidepressants (e. g., nefopam, oxypertine, doxepin, amoxapine, trazodone, amitriptyline, maprotiline, phenelzine, desipramine, nortriptyline, tranylcypromine, fluoxetine, doxepin, imipramine, imipramine pamoate, isocarboxazid, trimipramine, and protriptyline);

antidiabetics (e.g., biguanides and sulfonylurea derivatives);

antifungal agents (e.g., griseofulvin, ketoconazole, itraconizole, amphotericin B, nystatin, and candicidin);

antihypertensive agents (e.g., propanolol, propafenone, oxyprenolol, nifedipine, reserpine, trimethaphan, phenoxybenzamine, pargyline hydrochloride, deserpidine, diazoxide, guanethidine monosulfate, minoxidil, rescinnamine, sodium nitroprusside, rauwolfia serpentina, alseroxylon, and phentolamine);

anti-inflammatory agents (e.g., (non-steroidal) indomethacin, ketoprofen, flurbiprofen, naproxen, ibuprofen, ramifenazone, piroxicam, (steroidal) cortisone, dexamethasone, fluazacort, CELECOXIB, rofecoxib, hydrocortisone, prednisolone, and prednisone);

antineoplastics (e.g., cyclophosphamide, actinomycin, bleomycin, daunorubicin, doxorubicin, epirubicin, mitomycin, methotrexate, FLUOROURACIL, carboplatin, carmustine (BCNU), methyl-CCNU, cisplatin, etoposide, camptothecin and derivatives thereof, phenesterine, PACLITAXEL and derivatives thereof, docetaxel and derivatives thereof, vinblastine, vincristine, tamoxifen, and PIPOSULFAN);

antianxiety agents (e.g., lorazepam, buspirone, prazepam, chlordiazepoxide, oxazepam, clorazepate dipotassium, diazepam, hydroxyzine pamoate, hydroxyzine hydrochloride, ALPRAZOLAM, droperidol, halazepam, chlormezanone, and dantrolene);

immunosuppressive agents (e.g., cyclosporine, azathioprine, mizoribine, and FK506 (TACROLIMUS));

antimigraine agents (e.g., ergotamine, PROPANOLOL, isometheptene mucate, and dichloralphenazone);

sedatives/hypnotics (e.g., barbiturates such as pentobarbital, pentobarbital, and secobarbital; and benzodiazapines such as flurazepam hydrochloride, triazolam, and midazolam);

antianginal agents (e.g., beta-adrenergic blockers ; calcium channel blockers such as nifedipine, and diltiazem; and nitrates such as nitroglycerin, isosorbide dinitrate, pentaerythritol tetranitrate, and erythrityl tetranitrate);

antipsychotic agents (e. g., haloperidol, loxapine succinate, loxapine hydrochloride, thioridazine, thioridazine hydrochloride, thiothixene, FLUPHENAZINE, FLUPHENAZINE decanoate, fluphenazine enanthate, trifluoperazine, chlorpromazine, perphenazine, lithium citrate, and prochlorperazine);

antimanic agents (e.g., lithium carbonate);

antiarrhythmic agents (e.g., bretylium tosylate, esmolol, verapamil, amiodarone, encainide, digoxin, digitoxin, mexiletine, disopyramide phosphate, procainamide, quinidine sulfate, quinidine gluconate, quinidine polygalacturonate, flecainide acetate, tocainide, and lidocaine);

antiarthritic agents (e.g., phenylbutazone, sulindac, PENICILLANINE, salsalate, piroxicam, azathioprine, indomethacin, MECLOFENAMATE, gold sodium thiomalate, ketoprofen, auranofin, aurothioglucose, and tolmetin sodium);

antigout agents (e.g., colchicine, and allopurinol); anticoagulants (e.g., heparin, heparin sodium, and warfarin sodium);

thrombolytic agents (e.g., urokinase, streptokinase, and alteplase);

antifibrinolytic agents (e.g., aminocaproic acid);

hemorheologic agents (e.g., pentoxifylline);

antiplatelet agents (e.g., aspirin);

anticonvulsants (e.g., VALPROIC acid, divalproex sodium, phenytoin, phenytoin sodium, clonazepam, primidone, phenobarbitol, carbamazepine, amobarbital sodium, methsuximide, metharbital, mephobarbital, mephenytoin, phensuximide, paramethadione, ethotoin, phenacemide, SECOBARBITOL sodium, clorazepate dipotassium, and trimethadione);

antiparkinsonism agents (e.g., ethosuximide);

antihistamines/antipruritics (e.g., hydroxyzine, diphenhydramine, chlorpheniramine, brompheniramine maleate, cyproheptadine hydrochloride, terfenadine, clemastine fumarate, triprolidine, carbinoxamine, diphenylpyraline, phenindamine, azatadine, tripelennamine, dexchlorpheniramine maleate, methdilazine, and);

agents useful for calcium regulation (e.g., calcitonin, and parathyroid hormone);

antibacterial agents (e.g., amikacin sulfate, aztreonam, chloramphenicol, chloramphenicol palirtate, ciprofloxacin, clindamycin, clindamycin palmitate, clindamycin phosphate, metronidazole, metronidazole hydrochloride, gentamicin sulfate, lincomycin hydrochloride, tobramycin sulfate, vancomycin hydrochloride, polymyxin B sulfate, colistimethate sodium, and colistin sulfate);

antiviral agents (e.g., interferon alpha, beta or gamma, zidovudine, amantadine hydrochloride, ribavirin, and acyclovir);

antimicrobials (e.g., cephalosporins such as cefazolin sodium, cephradine, cefaclor, cephapirin sodium, ceftizoxime sodium, CEFOPERAZONE sodium, cefotetan disodium, cefuroxime e azotil, cefotaxime sodium, cefadroxil monohydrate, cephalexin, cephalothin sodium, cephalexin hydrochloride monohydrate, cefamandole nafate, cefoxitin sodium, cefonicid sodium, ceforanide, ceftriaxone sodium, ceftazidime, cefadroxil, cephradine, and cefuroxime sodium; penicillins such as ampicillin, amoxicillin, penicillin G benzathine, cyclacillin, ampicillin sodium, penicillin G potassium, penicillin V potassium, piperacillin sodium, oxacillin sodium, bacampicillin hydrochloride, cloxacillin sodium, ticarcillin disodium, azlocillin sodium, carbenicillin indanyl sodium, penicillin G procaine, methicillin sodium, and nafcillin sodium; erythromycins such as erythromycin ethylsuccinate, erythromycin, erythromycin estolate, erythromycin lactobionate, erythromycin stearate, and erythromycin ethylsuccinate; and tetracyclines such as tetracycline hydrochloride, doxycycline hyclate, and minocycline hydrochloride, azithromycin, clarithromycin);

anti-infectives (e.g., GM-CSF);

bronchodilators (e.g., sympathomimetics such as epinephrine hydrochloride, metaproterenol sulfate, terbutaline sulfate, isoetharine, isoetharine mesylate, isoetharine hydrochloride, albuterol sulfate, albuterol, bitolterolmesylate, isoproterenol hydrochloride, terbutaline sulfate, epinephrine bitartrate, metaproterenol sulfate, epinephrine, and epinephrine bitartrate; anticholinergic agents such as ipratropium bromide; xanthines such as aminophylline, dyphylline, metaproterenol sulfate, and aminophylline; mast cell stabilizers such as cromolyn sodium; inhalant corticosteroids such as beclomethasone dipropionate (BDP), and beclomethasone dipropionate monohydrate; salbutamol; ipratropium bromide; budesonide; ketotifen; salmeterol; xinafoate; terbutaline sulfate; triamcinolone; theophylline; nedocromil sodium; metaproterenol sulfate; albuterol; flunisolide; fluticasone proprionate;

steroidal compounds and hormones (e.g., androgens such as danazol, testosterone cypionate, fluoxymesterone, ethyltestosterone, testosterone enathate, methyltestosterone, fluoxymesterone, and testosterone cypionate; estrogens such as estradiol, estropipate, and conjugated estrogens; progestins such as methoxyprogesterone acetate, and norethindrone acetate; corticosteroids such as triamcinolone, betamethasone, betamethasone sodium phosphate, dexamethasone, dexamethasone sodium phosphate, dexamethasone acetate, prednisone, methylprednisolone acetate suspension, triamcinolone acetonide, methylprednisolone, prednisolone sodium phosphate, methylprednisolone sodium succinate, hydrocortisone sodium succinate, triamcinolone hexacetonide, hydrocortisone, hydrocortisone cypionate, prednisolone, fludrocortisone acetate, paramethasone acetate, prednisolone tebutate, prednisolone acetate, prednisolone sodium phosphate, and hydrocortisone sodium succinate; and thyroid hormones such as levothyroxine sodium);

hypoglycemic agents (e.g., human insulin, purified beef insulin, purified pork insulin, glyburide, chlorpropamide, glipizide, tolbutamide, and tolazamide); hypolipidemic agents (e.g., clofibrate, dextrothyroxine sodium, probucol, pravastitin, atorvastatin, lovastatin, and niacin);

proteins (e.g., DNase, alginase, superoxide dismutase, and lipase);

nucleic acids (e.g., sense or anti-sense nucleic acids encoding any therapeutically useful protein, including any of the proteins described herein);

agents useful for erythropoiesis stimulation (e.g., erythropoietin);

anticulcer/antireflux agents (e.g., famotidine, cimetidine, and ranitidine hydrochloride);

antinausea/antiemetics (e.g., meclizine hydrochloride, nabilone, prochlorperazine, dimenhydrinate, promethazine hydrochloride, thiethylperazine, and scopolamine);

oil-soluble vitamins (e.g., vitamins A, D, E, K, and the like); as well as other drugs such as mitotane, halonitrosoureas, anthrocyclines, and ellipticine.

Other useful agents include decongestant, antiparasitic agent, local anesthetic, amoebicidal agent, trichomonocidal agent, neuroleptic agent, anxiolytic energizer, muscle relaxant agent, antimalarial agent, hormonal agent, contraceptive agent, sympathomimetic agent, antilipemic agent, ophthalmic agent, electrolytic agent, diagnostic agent, prokinetic agent, gastric acid secretion inhibitor agent, anti-flatulent agent, anti-incontinence agent, cardiovascular agent, NOOTROPIC, and vasodilators. A description of these and other classes of usefull drugs and a listing of species within each class can be found in Martindale, The Extra Pharmacopoeia, 31ST Ed. (The Pharmaceutical Press, London 1996), the disclosure of which is incorporated herein by reference in its entirety.

Examples of still other drugs suitable for use in the compositions and methods described herein include ceftriaxone, ketoconazole, ceftazidime, oxaprozin, albuterol, valacyclovir, urofollitropin, famciclovir, flutamide, enalapril, mefformin, itraconazole, buspirone, gabapentin, fosinopril, tramadol, acarbose, lorazepan, follitropin, glipizide, omeprazole, fluoxetine, lisinopril, tramsdol, levofloxacin, zafirlukast, interferon, growth hormone, interleukin, erythropoietin, granulocyte stimulating factor, nizatidine, bupropion, perindopril, erbumine, adenosine, alendronate, alprostadil, benazepril, betaxolol, bleomycin sulfate, dexfenfluramine, diltiazem, fentanyl, flecainid, gemcitabine, glatiramer acetate, granisetron, lamivudine, mangafodipir trisodium, mesalamine, metoprolol fumarate, metronidazole, miglitol, moexipril, monteleukast, octreotide acetate, olopatadine, paricalcitol, somatropin, sumatriptan succinate, tacrine, verapamil, nabumetone, trovafloxacin, dolasteron, zidovudine, finasteride, tobramycin, isradipine, tolcapone, enoxaparin, fluconazole, lansoprazole, terbinafine, pamidronate, didanosine, diclofenac, cisapride, venlafaxine, troglitazone, fluvastatin, losartan, imiglucerase, donepezil, olanzapine, valsartan, fexofenadine, calcitonin, and ipratropium bromide. These drugs are generally considered to be water soluble.

Preferred drugs include albuterol, adapalene, doxazosin mesylate, mometasone furoate, ursodiol, amphotericin, enalapril maleate, felodipine, nefazodone hydrochloride, valrubicin, albendazole, conjugated estrogens, medroxyprogesterone acetate, nicardipine hydrochloride, zolpidem tartrate, amlodipine besylate, ethinyl estradiol, omeprazole, rubitecan, amlodipine besylate/benazepril hydrochloride, etodolac, paroxetine hydrochloride, paclitaxel, atovaquone, felodipine, podofilox, paricalcitol, betamethasone dipropionate, fentanyl, pramipexole dihydrochloride, Vitamin D3 and related analogues, finasteride, quetiapine fumarate, alprostadil, candesartan, cilexetil, fluconazole, ritonavir, busulfan, carbamazepine, flumazenil, risperidone, carbemazepine, carbidopa, levodopa, ganciclovir, saquinavir, amprenavir, carboplatin, glyburide, sertraline hydrochloride, rofecoxib carvedilol, halobetasolproprionate, sildenafil citrate, celecoxib, chlorthalidone, imiquimod, simvastatin, citalopram, ciprofloxacin, irinotecan hydrochloride, sparfloxacin, efavirenz, cisapride monohydrate, lansoprazole, tamsulosin hydrochloride, mofafinil, clarithromycin, letrozole, terbinafine hydrochloride, rosiglitazone maleate, diclofenac sodium, lomefloxacin hydrochloride, tirofiban hydrochloride, telmisartan, diazapam, loratadine, toremifene citrate, thalidomide, dinoprostone, mefloquine hydrochloride, trandolapril, docetaxel, mitoxantrone hydrochloride, tretinoin, etodolac, triamcinolone acetate, estradiol, ursodiol, nelfmavir mesylate, indinavir, beclomethasone dipropionate, oxaprozin, flutamide, famotidine, nifedipine, prednisone, cefuroxime, lorazepam, digoxin, lovastatin, griseofulvin, naproxen, ibuprofen, isotretinoin, tamoxifen citrate, nimodipine, amiodarone, and alprazolam.

Other drugs that can be included in the capsule include progesterone, acetohexamide, dapsone, ivermectin, pilocarpine, spironolactone, tegaserod maleate, tolbutamide, 1,2-dithiole-3-thiones, 5-niro-2-(3-phenylpropylamino) benzoic acid, 5-phenyl-1, 2-dithiole-3-thione, 9-aminocamptothecin, alosetrom, ampotericin B, aripiprazole, artemisinin, ascomycin, bafilomycin A, benzylguanine, BMS 214662, BMS-247550, bumetanide, bupivacaine, calcipotriol, ceterizine, chloropropamide, chlorotoxin, ciclesonide, cimetideine, cinnarizine, concanamycin A, darifenacin, des-loratadine, dexmedetomidine, dextromethorphan+pseudoephedrine, dihydroergotamine, dipyridamole, ditiazem, DY-9760e, elitriptan, EPLERENONE, epothilone B, erlotinib, fenofibrate, flurbiprofen, fluticasone diproprionate, fluticasone propionate, salmeterol xinafoate, furosemide, gentamycin, glibenclamide, hexylresorcinol, idarubicin, irenotecan, ketanserin, ketodolac, ketorolac, kynostatin, leuprolide, linezolid, loratidine, mechlorethamine, melphalan, metfomin, methoxy-morpholinodoxorubicin, methylphenidate, metoclopramide, miconazole, mirtazapine, o6-benzylguanine, ondansetron, pantoprazole, pen G, pentamidine, pioglitazone hydrochloride, prilocaine hydrochloride, propofol, R-(+)-DIOA, r (+)-iaa-94, rabeprazole, rapamycin, rifampicin, sanguinarine chloride, saquinavir mesylate, silatecan, tarceva (OSI-774), teniposide, teva TV-470 1, tirilazid mesylate, topotecan, triclosan, triptans, vindesine, vinpocetine, voriconazole, clotrimazole, zaleplon, ziprasidone, zopiclone, zyvox, escitalopram, ropinirole, and vinorelbine.

The above-mentioned lists should not be considered exhaustive and is merely exemplary of the many embodiments considered within the scope of the invention. Many other active agents can be administered with the capsule of the present invention.

The active agent (s) contained within the present capsule can be formulated as its pharmaceutically acceptable salts. As used herein, "pharmaceutically acceptable salts" refers to derivatives of the disclosed compounds wherein the active agent is modified by reacting it with an acid or base as needed to form an tonically bound pair. Examples of pharmaceutically acceptable salts include conventional non-toxic salts or the quaternary ammonium salts of the parent compound formed, for example, from non-toxic inorganic or organic acids. Suitable non-toxic salts include those derived from inorganic acids such as hydrochloric, hydrobromic, sulfuric, sulfonic, sulfamic, phosphoric, nitric and others known to those of ordinary skill in the art. The salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, METHANESULFONIC, ethane disulfonic, oxalic, isethionic, and others known to those of ordinary skill in the art. The pharmaceutically acceptable salts of the present invention can be synthesized from the parent active agent which contains a basic or acidic moiety by conventional chemical methods. Lists of other suitable salts are found in Remington's Pharmaceutical Sciences, 17TH. ed., Mack Publishing Company, Easton, Pa., 1985, the relevant disclosure of which is hereby incorporated by reference.

As used in this disclosure, the term vitamin refers to trace organic substances that are required in the diet. For the purposes of the present invention, the term vitamin(s) include, without limitation, thiamin, riboflavin, nicotinic acid, pantothenic acid, pyridoxine, biotin, folic acid, vitamin B12, lipoic acid, ascorbic acid, vitamin A, vitamin D, vitamin E and vitamin K. Also included within the term vitamin are the coenzymes thereof. Coenzymes are specific chemical forms of vitamins and can include thiamin pyrophosphates (TPP), flavin mononucleotide (FMN), and flavin adenine dinucleotive (FAD). Nicotinamide adenine dinucleotide (NAD), Nicotinamide adenine dinucleotide phosphate (NADP), Coenzyme A (CoA), pyridoxal phosphate, biocytin, tetrahydrofolic acid, coenzyme B12, lipolysine, 11-CIS-RETINAL, and 1,25-dihydroxycholecalciferol. The term vitamin (s) also includes choline, carnitine, and alpha, beta, and gamma carotene.

As used in this disclosure, the term "mineral" refers to inorganic substances, metals, and the like required in the human diet. Thus, the term "mineral" as used herein includes, without limitation, calcium, iron, zinc, selenium, copper, iodine, magnesium, phosphorus, chromium, mixtures thereof and others known to those of ordinary skill in the art.

The term "dietary supplement" as used herein means a substance, which has an appreciable nutritional effect when, administered in small amounts. Dietary supplements include, without limitation, such ingredients as bee pollen, bran, wheat germ, kelp, cod liver oil, ginseng, and fish oils, amino-acids, proteins, plant extracts, plant powder, herbs, herbal extracts and powders, vitamins, minerals, combinations thereof and others known to those of ordinary skill in the art. As will be appreciated, essentially any dietary supplement may be incorporated into the present capsule.

The amount of active agent incorporated in a capsule of the invention will be at least one or more dosage form and can be selected according to known principles of pharmacy. An effective amount of active agent is specifically contemplated. By the term "effective amount", it is understood that, with respect to, for example, pharmaceuticals, a pharmaceutically effective amount is contemplated. A pharmaceutically effective amount is the amount or quantity of a drug or pharmaceutically active substance which is enough for the required or desired therapeutic response, or in other words, the amount, which is sufficient to elicit an appreciable biological response when, administered to a patient. The appreciable biological response may occur as a result of administration of single or multiple unit doses of an active substance. Depending upon the active agents used and upon the amount of active substance present in a particular capsule according to the invention, a unit dose may comprise one or more such capsules. As used with reference to a vitamin or mineral, the term "effective amount" means an amount at least about 10% of the United States Recommended Daily Allowance ("RDA") of that particular ingredient for a patient. For example, if an intended ingredient were vitamin C, then an effective amount of vitamin C would include an amount of vitamin C sufficient to provide 10% or more of the RDA. Typically, where the tablet includes a mineral or vitamin, it will incorporate higher amounts, preferably about 100% or more of the applicable RDA.

When combinations of active agents are used, one or both of the active agents can be present in a sub-therapeutic amount. As used herein, a sub-therapeutic amount is that amount of first drug which provides less than a normal therapeutic response in patient to which the first drug is administered in the absence of the second drug of the combination.

In other words, the first and second drugs may together provide an enhanced, improved, additive or synergistic therapeutic benefit as compared to the administration of each drug alone, i.e., in the absence of the other drug.

As used herein, the term acid-ionizable agent is taken to mean any compound that becomes or is ionized in the presence of an acid. An acid-ionizable agent comprises at least one acid-ionizable functional group that becomes ionized when exposed to acid or when placed in an acidic medium. Exemplary acid-ionizable functional groups include a primary amine, secondary amine, tertiary arnine, quaternary amine, aromatic amine, unsaturated amine, primary thiol, secondary thiol, sulfonium, hydroxyl, enol and others known to those of ordinary skill in the chemical arts.

The degree to which an acid-ionizable agent is bound by non-covalent ionic binding versus inclusion complexation formation can be determined spectrophotometrically using methods such as $^{1}$HNMR, $^{13}$CNMR, or circular dichroism (CD), for example, and by analysis of the phase solubility data for the acid-ionizable agent and SAE-CD. The artisan of ordinary skill in the art will be able to use these conventional methods to approximate the amount of each type of binding that is occurring in solution to determine whether or not binding between the species is occurring predominantly by non-covalent ionic binding or inclusion complex formation.

An acid-ionizable agent that binds to SAE-CD by both means will generally exhibit a bi-phasic phase solubility curve. Under conditions where non-covalent ionic bonding predominates over inclusion complex formation, the amount of inclusion complex formation, measured by NMR or CD, will be reduced even though the phase solubility data indicates significant binding between the species under those conditions; moreover, the intrinsic solubility of the acid-ionizable agent, as determined from the phase solubility data, will generally be higher than expected under those conditions.

As used herein, the term non-covalent ionic bond refers to a bond formed between an anionic species and a cationic species. The bond is non-covalent such that the two species together form a salt or ion pair. The SAE-CD provides the anionic species of the ion pair and the acid-ionizable agent provides the cationic species of the ion pair. Since the SAE-CD is multi-valent, an SAE-CD can form an ion pair with one or more acid-ionizable agents.

As used herein in reference to the active agent, the terms "very soluble", "freely soluble", "soluble", "sparingly soluble", "slightly soluble", "very slightly soluble", and "practically insoluble" or "insoluble" are defined as they are defined in the U.S.P. 23RD Ed. as follows:

| Term | Solubility of component in water (parts of solvent per part of component) |
|---|---|
| Very soluble | <1 |
| Freely soluble | 1-10 |
| Soluble | 10-30 |
| Sparingly soluble | 30-100 |
| Slightly soluble | 100-1,000 |
| Very slightly soluble | 1,000-10,000 |
| Practically insoluble or insoluble | Over 10,000 |

When an active agent is included in a capsule of the invention, it need not necessarily complex with the SAE-CD. A study was conducted to determine whether or not complexation of a drug to the SAE-CD alters the ability of the SAE-CD to stabilize the capsule shell against dissolution, erosion, swelling or degradation caused by water in the fill composition enclosed within the capsule shell. Banner's hydrophilic, HFB, and lipophilic, LFB, air fill size 35 oval gelatin capsules were used in this study, which was performed as described below. The aqueous fill compositions tested in this experiment comprise 60% w/w and 70% w/w SAE-CD in combination with various marketed drugs. The 60% w/w SAE-CD was prepared by weighing a known amount of water and SAE-CD in two separate containers. The SAE-CD was slowly added to the water while it was stirring and on a hot plate. Agitation continued until all the SAE-CD dissolved. The SAE-CD was divided by weighing in equal amounts into nine vials (one for each drug). The solid active drug was then added to the SAE-CD solution. The amount of drug added produced a composition that contained a normal dose of drug in 1 gram. The vials were agitated and heated until a solution was obtained or the active was uniformly suspended. Four grams (3 mL) of the 60% w/w SAE-CD/drug solution or suspension was added to the various capsule halves and the vials were shaken for the duration of the study. The results for the HSIT in 60% w/w SAE-CD with drug are found in the table below. The active ingredients in the table form an inclusion complex with SAE-CD to varying degrees depending on their binding constants.

| Active ingredient | Amount of drug in 1 gram (mg) | Fill composition appearance | HSIT HFB | HSIT LFB |
|---|---|---|---|---|
| Cinnarizine | 25 | suspension | 5 | 5 |
| Indomethacin | 25 | solution | 5 | 5 |
| Hydrocortisone | 5 | clear solution | 5 | 4 |
| Fexofenadine HCl | 60 | solution | 5 | 5 |
| Testosterone | 10 | clear solution | 5 | 5 |
| Methyltestosterone | 10 | clear solution | 5 | 5 |
| Budesonide | 3 | suspension | 5 | 5 |
| Carvedilol | 25 | solution | 5 | 5 |
| Sertraline HCl | 50 | solution | 5 | 4 |

An HSIT study was also conducted with the same amounts of drug as above but with 70% w/w SAE-CD. The results of that evaluation are found in table below.

| Active ingredient | Amount of drug in 1 gram (mg) | Fill composition appearance | HSIT HFB | HSIT LFB |
|---|---|---|---|---|
| Cinnarizine | 25 | suspension | 5 | 5 |
| Indomethacin | 25 | clear solution | 5 | 5 |
| Hydrocortisone | 5 | clear solution | 5 | 5 |
| Fexofenadine HCl | 60 | clear solution | 5 | 5 |
| Testosterone | 10 | clear solution | 5 | 5 |
| Methyltestosterone | 10 | clear solution | 5 | 5 |
| Budesonide | 3 | suspension | 5 | 5 |
| Carvedilol | 25 | clear solution | 5 | 5 |
| Sertraline HCl | 50 | clear solution | 5 | 5 |

The results indicate complexation of the drug with SAE-CD does not significantly reduce the ability of SAE-CD to extend the shelf-life of a capsule containing an aqueous fill composition according to the invention.

Capsules containing sertraline in an aqueous fill composition of the invention were prepared according to Example 9. The table below includes a summary the drug release profiles of two 50 mg capsules of the invention in SGF.

Sertraline HCL Release from Soft Gelatin Capsules

| $Time_{fraction\ released}$ | Time in Minutes t 10% | t 50% | t 90% |
|---|---|---|---|
| Capsule 1 | 7.5 | 11.5 | 16 |
| Capsule 2 | 10 | 12 | 15 |
| Average | 8.8 | 11.8 | 15.5 |

It is thought that the initial drug release may be due to some fill composition on the outside of the gelatin capsule and that the slow release at the end of the profile may be due to some drug trapped in the gelatin that had been heat-sealed.

In view of the above description and the examples below, one of ordinary skill in the art will be able to practice the invention as claimed without undue experimentation. The foregoing will be better understood with reference to the following examples that detail certain procedures for the preparation of formulations according to the present invention. All references made to these examples are for the purposes of illustration. The following examples should not be considered exhaustive, but merely illustrative of only a few of the many embodiments contemplated by the present invention.

EXAMPLE 1

The following general method is used for the preparation of aqueous fill compositions comprising water, a derivatized cyclodextrin and optionally an active agent.

A known amount of derivatized cyclodextrin is placed in a known amount of water while mixing. The water is optionally heated prior to mixing or the mixture is heated during and/or after mixing. The active agent, if present, is added to the water before, along with or after addition of the derivatized cyclodextrin. Alternatively, the active agent is mixed or complexed with the derivatized cyclodextrin prior to addition to water.

Alternatively, a concentrated stock composition comprising the derivatized cyclodextrin and water is added to an aqueous solution optionally comprising an active agent to form a diluted aqueous fill composition.

Alternatively, a diluted stock composition comprising the derivatized cyclodextrin and water, and optionally active agent and optionally excipient(s), is concentrated by removal of water there from. Removal of water can be done by desiccation, evaporation, vacuum drying, oven drying, tray drying or other conventional procedures for removal of water.

Other excipients useful in the fill composition can be added as needed at any point along the above-described process.

EXAMPLE 2

The following general method is used to evaluate the aqueous fill compositions to determine whether or not they are suitable for use according to the invention.

Method A: Half-Shell integrity Test (H.S.I.T.)

In a closed container, a portion of a capsule shell is exposed to an aqueous fill composition comprising a known amount of derivatized cyclodextrin, water and optionally one or more other excipients. Observation of changes, or lack thereof, on the exposed portion's size, appearance, shape, dissolution, erosion, degradation, hardness, and/or translucence are recorded periodically over time. A rating scale is used to quantify the overall performance of the capsule portion during the test. Although many different rating scales can be used, an exemplary rating scale includes the following: 0 rating: capsule portion dissolved within <24 hrs; 1 rating: shape and/or size of capsule changed such that the portion is extremely deformed or enlarged within ≧24 hours and <48 hrs; 2 rating: shape and/or size of capsule changed such that the portion is extremely deformed or enlarged within ≧2 days and <5 days; 3 rating: shape and/or size of capsule changed such that the portion is partially changed, e.g., the capsule is enlarged and may have slight deformities, within ≧5 DAYS and <10 days; 4 rating: shape and/or size of capsule changed slightly such that the portion may be enlarged but not deformed within ≧10 days and <14 days; 5 rating: shape and/or size of capsule changed such that the portion is unchanged or not visibly changed after ≧14 days.

Method B: Filled Capsule Shell Integrity Test

A capsule shell is filled with an aqueous fill composition comprising a known amount of derivatized cyclodextrin, water and optionally one or more other excipients. The filled capsule is placed in a closed container. Observations of changes, or lack thereof, on the exposed portion's size, appearance, shape, dissolution, erosion, degradation, hardness, leaking and/or translucence are recorded periodically over time. A rating scale such as the one described in Method A of this example is used to quantify the overall performance of the filled capsule during the test.

EXAMPLE 3

Water activity was measured by placing a sample solution in a small, sealed container and determining the equilibrium humidity and temperature in the container. Instruments such as the HygroLab 3 from Rotronic Instrument Corp. , Huntington, N.Y. were used to measure the water activity. The humidity is determined using a thin film capacitive sensor in the headspace of the container. The temperature is determined using a Pt RTD 100 sensor. From these measurements the activity of water (Aw) is calculated by the instrument. The instrument has an accuracy of about ±0.015 Aw and a repeatability of about ±0.005 Aw. Carefully prepared salt-containing stock solutions of known concentration and water activity were used to calibrate the instrument prior to use.

EXAMPLE 4

The following general method is used to evaluate aqueous fill compositions comprising water, a derivatized cyclodextrin and a shell-stabilizing material.

Water Activity Approximation

A fill composition is prepared by mixing known amounts of water, derivatized cyclodextrin and shell-stabilizing material optionally in the presence of heat. The water activity of the aqueous fill composition is measured according to Example 3. Depending upon the value of water activity, the fill composition is then evaluated according to Example 2 to determine a performance rating. If the water activity approximates or is less than 0.95±0.025, then the fill composition is optionally evaluated according to Example 2 to determine its suitability for use according to the invention. Depending upon the composition of the shell being used, a different water activity value may be used as the initial screening value. For example, a water activity value of less than about 0.9±0.025 may be used to screen formulations containing water, a derivatized cyclodextrin and a shell-stabilizing material for use in a gelatin capsule shell. Also, a water activity value of less than about 0.95±0.025 may be used to screen formulations containing water and a derivatized cyclodextrin for use in a gelatin capsule shell. In addition, the target water activity value may vary according to the derivatized cyclodextrin being used in the test.

EXAMPLE 5

Clarity of the fill compositions herein can be determined by visual inspection; however, other known methods for determining the clarity of a fill composition can be performed. Exemplary other methods include transmittance spectrophotometry at a wavelength of 800 nm.

EXAMPLE 6

The following example was followed to obtain the dissolution profiles of FIG. 11.

Dissolution studies were performed according to United States PHARMACOPEIA <711>; DISSOLUTION. Apparatus 2, paddles, at 50 rpm, was utilized with 900 mL of various dissolution media. A 60% w/w SAE-CD (Captisol) was prepared by adding a known weight of SAE-CD to a known weight of water and stirring until a clear solution was obtained. A weighed amount of fexofenadine HCL was added to a known volume of this solution. The mixture was stirred to prepare a 60 mg/mL solution of fexofenadine HCL. One gram of this solution was then filled into HFB soft gelatin capsules and the capsules sealed prior to testing. For comparison, commercial 60 mg fexofenadine HCL tablets were tested using the same apparatus. Samples of the dissolution media were withdrawn periodically, filtered, and assayed using high performance chromatography (Radhakrishna, T and Reddy, G. Om; "Simultaneous determination of fexofenadine and its related compounds by HPLC", *Journal of Pharmaceutical and Biomedical Analysis* 29 (2002) 681-690).

EXAMPLE 7

This procedure was used to prepare soft gelatin capsules containing 25 mg of carvedilol per capsule. The capsules, which are enteric coated, provide a delayed release of the carvedilol. After oral administration to a subject, release of the drug does not begin until after the capsule has passed the acidic environment of the stomach. This capsule is a post-gastric release (or enteric release) capsule.

a. Preparation of 25 mg Carvedilol Soft Gelatin Capsules

To a ten-gram sample of a 60% (W/W) Captisol solution was added 250 mg of Carvedilol (received from Ultra-tech, India) and 200 mg of sodium bitartrate. The sample in a 25 cc bottle was rotated overnight to allow dissolution of the drug. From observation under the microscope most if not all of the carvedilol had dissolved; however, not all of the sodium bitartrate was in solution based on the appearance of its characteristic crystal shape. The bottle was centrifuged at low speed to remove the undissolved sodium bitartrate from solution. Nine soft air filled capsules (HFC shells) were filled with Ig (5%) of the solution from above using a syringe and needle. The hole in the capsule was then heat-sealed.

b. Enteric Coating of Soft Gelatin Capsules

The capsule was then coated with ACRYL-EZE™, an aqueous acrylic enteric coating system formulated and available from Colorcon (West Point, Pa.) based on the enteric polymer EUDRAGIT® L100-55 (otherwise known as methacrylic acid copolymer type C). The ACRYL-EZE™ COATING formulation contained:

| | |
|---|---|
| ACRYL-EZE | 200 G |
| Antifoam A Solution | 6 drops |
| Water | 800 g |

A Uni-Glatt fluidized bed coater with Wuster column was used for coating the filled capsules according to the following parameters:

| | |
|---|---|
| Inlet air temperature | 40° C. |
| Outlet air temperature | 36° C. |
| Coating rate | 5 g per minute |

The fluidized bed was loaded with 400 g of high-density polyethylene drops previously coated with ACRYL-EZE™ and the nine filled soft gelatin capsules. An estimate was made of the amount of coating applied by weighing some of the coated capsules and subtracting the approximate weight of the filled capsules. The percent coat weight was estimated to be about 12%.

These capsules provide a delayed release of carvedilol. After oral administration to a subject, release of the drug does not begin until after the capsule has passed the acidic environment of the stomach. Therefore, release of drug does not generally occur in an acidic environment. This capsule is a post-gastric release (or enteric release) capsule.

EXAMPLE 8

This procedure was used to evaluate the dissolution and drug release properties of enteric soft gelatin capsules, for example, those of Example 7 containing 25 mg of carvedilol per capsule.

Three capsules were placed into an acid phase consisting of simulated gastric fluid (SGF) without enzyme (USP pH 1.2) in a USP Apparatus 2 dissolution system with 50-rpm paddle rotation, 37° C., and using flow through spectrophotometer set to monitor the appearance of carvedilol at 332 nm. No release of carvedilol was observed over the 2 hours in SGF. The capsules were transferred to a phosphate buffer (pH 6.8), otherwise known as simulated intestinal fluid (SIF). The enteric coating was observed to dissolve by way of the appearance of talc and titanium dioxide released into the dissolution media.

The appearance of carvedilol was observed to increase in the dissolution media as indicated by the increase in UV absorption at 332 nm. Visual observation showed that the capsules were completely dissolved at 1 hour after the transfer to the SIF. Filtered samples of the dissolution media gave absorption readings of 0.30 to 032 at 332 nm indicating that the drug was all in solution.

EXAMPLE 9

This procedure was used to evaluate the performance of the soft gelatin capsules of Example 7 when exposed to disintegrating conditions.

A USP disintegration test was set up to observe the dissolution of the capsules in just the pH 6.8 SIF. The following observations were made by changing the media every 10 minutes to facilitate viewing by reducing the interference from the coating particulate matter:

| TIME (min) | RESULT |
|---|---|
| 0 to 10 | coating intact |
| 10 to 20 | first observation of soft gelatin capsule surface |
| 20 to 30 | some evidence of drug being released into media |
| 30 to 40 | most capsule contents gone, some coating and capsule pieces visible |
| 40 to 50 | most gelatin dissolved but some coating still visible |

EXAMPLE 10

This procedure was used to prepare a soft gelatin capsule that provides a rapid release of sertraline, wherein the capsule comprises a water-miscible aqueous fill composition. Soft gelatin capsules containing 50 and 100 mg per capsule of sertraline as the HCL salt in 70% CAPTISOL/Water (w/w) are prepared as follows. Then, the drug release profile in simulated gastric fluid (SGF) is determined.

a. Preparation

A stock solution containing 88 mg of sertraline per gram and 70% wt. of SBE-CD was prepared. Two air-filled soft gelatin capsules (HFB shells) were filled with 0.57 g and one air-filled SGC was filled with 1.14 g of a solution of 88 mg of setraline per gram using a pipette and then the holes in the capsules were heat-sealed.

b. Drug Release in Simulated Gastric Fluid (SGF)

Release of sertraline was followed using a spectrophotometer equipped with flow-through cells at a wavelength of 272.2 nm. A USP Apparatus No. 2 with a paddle rpm of 50, temperature 37° C. and 900 mL of simulated gastric fluid (SGF, pH 1.2 HCL with 2 g per liter sodium chloride) was used. The capsules were place in the SGF and release of drug over time measured.

The disclosures of the references cited herein are hereby incorporated in their entirety.

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except by the appended claims. All of the embodiments disclosed and claimed herein can be made and executed without undue experimentation in light of the present disclosure.

We claim:

1. A capsule comprising:

a water soluble, erodible, degradable and/or swellable shell; and an aqueous fill composition comprising one or more active agents, water in an amount of at least 10% to less than 50%, by weight, of the fill composition, and a water soluble cyclodextrin derivative in an amount of at least 50%, by weight, of the fill composition, wherein the capsule has a shelf-life of at least one week;

wherein the fill composition has a water activity of less than 0.95±0.01, and wherein the water soluble cyclodextrin derivative is a sulfoalkyl ether cyclodextrin of formula 1:

Formula I

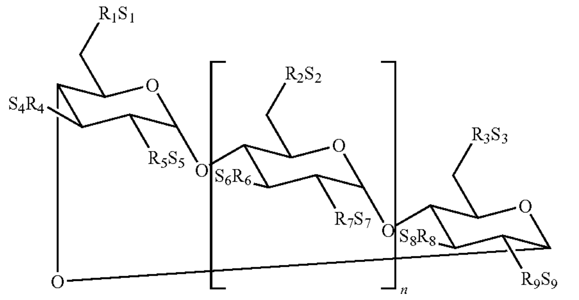

wherein: n is 4, 5 or 6; $R_1$, $R_2$, $R_3$, $R_4$, $R_5$, $R_6$, $R_7$, $R_8$ and $R_9$ are each, independently, —O—or —O—($C_2$-$C_6$ alkylene)—$SO_3^-$, wherein at least one of $R_1$, $R_2$ $R_3$, $R_4$, $R_5$, $R_6$, $R_7$, $R_8$ and $R_9$ is independently —O—($C_2$-$C_6$ alkylene)—$SO_3^-$selected from the group consisting of: —O—$(CH_2)_mSO_3^-$wherein m is 2 to 6, —$OCH_2CH_2CH_2SO_3^-$, and —$OCH_2CH_2CH_2CH_2SO_3^-$; and wherein $S_1$,$S_2$,$S_3$,$S_4$, $S_5$, $S_6$, $S_7$, $S_8$, and $S_9$ are each, independently, a cation.

2. The capsule of claim 1, wherein the aqueous fill composition is water miscible.

3. The capsule of claim 1, wherein the active agent is present in a therapeutically effective amount.

4. The capsule of claim 1, wherein the active agent is present in a sub-therapeutically effective amount.

5. The capsule of claim 1, wherein the active agent is sparingly soluble, slightly soluble, very slightly soluble, practically insoluble or insoluble in water.

6. The capsule of claim 1, wherein the active agent is more soluble in the aqueous fill composition than it is in water.

7. The capsule of claim 1, wherein the water soluble cyclodextrin derivative solubilizes the active agent when it is released into an environment of use.

8. The capsule of claim 1, wherein the active agent complexes with the cyclodextrin derivative to form an inclusion complex and/or a non-covalent ionic complex.

9. The capsule of claim 1, wherein the active agent is soluble, freely soluble or very soluble in water.

10. The capsule of claim 1, wherein the fill composition further comprises alcohol or other water miscible hydroxy moiety-containing material.

11. The capsule of claim 1, wherein the cation is independently selected at each occurrence from the group consisting of: $H^+$, an alkali metal cation, an alkaline earth metal cation, an ammonium cation, and an organic amine cation.

12. The capsule of claim 1, wherein the capsule has a shelf life of at least 7 days.

13. The capsule of claim 12, wherein the active agent is sparingly soluble, slightly soluble, very slightly soluble, practically insoluble or insoluble in water; and the cyclodextrin derivative solubilizes the active agent when it is released into an environment of use.

14. An aqueous fill composition in a water erodible, degradable, swellable and/or soluble shell, the fill composition comprising:

water in an amount of at least 10%, by weight, to less than 50%, by weight, of the fill composition, a water soluble cyclodextrin derivative in an amount of at least 50%, by weight, of the fill composition, one or more active agents, and optionally one or more excipients, wherein the water soluble cyclodextrin derivative is present in an amount sufficient to reduce erosion, degradation, swelling or dissolution of the shell caused by the water in the fill composition, were the water soluble cyclodextrin derivative absent, for a period of at least one week, in the absence of another shell-stabilizing material;

wherein the water activity of the fill composition is less than about 0.95±0.01; and wherein the water soluble cyclodextrin derivative is a sulfoalkyl ether cyclodextrin of formula 1:

Formula I

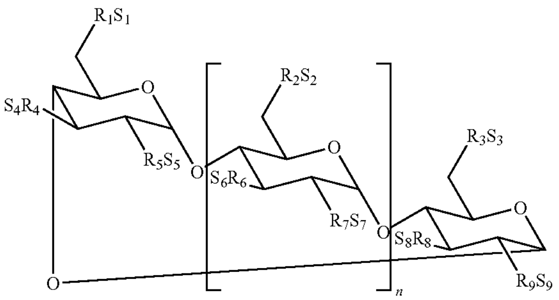

wherein: n is 4, 5 or 6; $R_1$, $R_2$, $R_3$, $R_4$, $R_5$, $R_6$, $R_7$, $R_8$ and $R_9$ are each, independently, —O—or —O—($C_2$-$C_6$ alkylene)—$SO_3^-$, wherein at least one of $R_1$, $R_2$, $R_3$, $R_4$, $R_5$, $R_6$, $R_7$, $R_8$ and $R_9$ is independently —O—($C_2$-$C_6$ alkylene)—$SO_3^-$selected from the group consisting of: —O—$(CH_2)_mSO_3^-$ wherein m is 2 to 6, —$OCH_2CH_2CH_2SO_3^-$, and —$OCH_2CH_2CH_2CH_2SO_3^-$; and wherein $S_1$, $S_2$, $S_3$, $S_4$, $S_5$, $S_6$, $S_7$, $S_8$ and $S_9$ are each, independently, a cation.

15. The capsule of claim 14, wherein the water activity of the aqueous fill composition is less than about 0.9.

16. The capsule of claim 14, wherein the water soluble cyclodextrin is present in an amount of ≧55%, by weight, of the fill composition.

17. The capsule of claim 14, wherein the water soluble cyclodextrin is present in an amount of ≧60%, by weight, of the fill composition.

18. The capsule of claim 14, wherein the water activity of the aqueous fill composition is less than about 0.925.

19. The fill composition of claim 14, wherein the cation is independently selected at each occurrence from the group consisting of $H^+$, an alkali metal cation, an alkaline earth metal cation, an ammonium cation, and an organic amine cation.

* * * * *